US012736520B2

(12) United States Patent
Paik et al.

(10) Patent No.: US 12,736,520 B2
(45) Date of Patent: Sep. 15, 2026

(54) APPARATUSES AND METHODS FOR DETERMINING ANALYTE CHARGE

(71) Applicant: The Board of Trustees of the Leland Stanford Junior University, Stanford, CA (US)

(72) Inventors: Kee-Hyun Paik, Stanford, CA (US); Henrik H.J. Persson, Stanford, CA (US); Billy Tsz Cheong Lau, Stanford, CA (US); Hanlee P. Ji, Stanford, CA (US); Robert W. Dutton, Stanford, CA (US); Yang Liu, Stanford, CA (US); Ronald W. Davis, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 16/838,882

(22) Filed: Apr. 2, 2020

(65) Prior Publication Data

US 2021/0048426 A1 Feb. 18, 2021

Related U.S. Application Data

(63) Continuation of application No. 15/382,364, filed on Dec. 16, 2016, now abandoned, which is a (Continued)

(51) Int. Cl.
*G01N 33/487* (2006.01)
*C12Q 1/6825* (2018.01)

(Continued)

(52) U.S. Cl.
CPC ..... *G01N 33/48721* (2013.01); *C12Q 1/6825* (2013.01); *C12Q 1/6869* (2013.01); *G01N 27/44791* (2013.01)

(58) Field of Classification Search
CPC ....... G01N 33/48721; G01N 27/44791; C12Q 1/68; C12Q 1/6825; C12Q 1/6869; C12Q 2565/607; C12Q 2565/631
See application file for complete search history.

(56) References Cited

U.S. PATENT DOCUMENTS 5,363,697 A 11/1994 Nakagawa
5,445,970 A 8/1995 Rohr (Continued)

FOREIGN PATENT DOCUMENTS

WO WO-93/09250 A1 5/1993
WO WO-03/100012 A2 12/2003

(Continued)

OTHER PUBLICATIONS

Allen, S. et al. (1997) "Detection of Antigen-Antibody Binding Events with the Atomic Force Microscope," Biochemistry 36:7457-7463.

(Continued)

*Primary Examiner* — Shizhi Qian
(74) *Attorney, Agent, or Firm* — Foley & Lardner LLP

(57) ABSTRACT

The present disclosure provides a sensor including a pore and an applied electric field that is capable of detecting analytes such as nucleic acids. In accordance with various embodiments, the sensor comprises a fluidic chamber having electrically opposing portions with a membrane between, the membrane providing a pore suitable for the passage of an electrolyte between the electrically opposing portions of the fluidic chamber, and having at least one charged analyte tethered in proximity to the pore, a first circuit configured to apply an electric field capable of passing the electrolyte through the pore and pulling the at least one charged analyte into the pore, and a second circuit configured to measure a signal indicative of the charge of the at least one charged analyte. Also provided are methods for (Continued)

using the sensor, for example, to sequence a nucleic acid molecule.

20 Claims, 37 Drawing Sheets

Related U.S. Application Data continuation of application No. PCT/US2015/036800, filed on Jun. 19, 2015.

(60) Provisional application No. 62/014,595, filed on Jun. 19, 2014.

(51) Int. Cl.
*C12Q 1/6869* (2018.01)
*G01N 27/447* (2006.01)

(56) References Cited

U.S. PATENT DOCUMENTS

| | | | | |
|---|---|---|---|---|
| 5,445,971 | A | 8/1995 | Rohr | |
| 5,831,070 | A | 11/1998 | Pease et al. | |
| 5,925,525 | A | 7/1999 | Fodor et al. | |
| 5,992,226 | A | 11/1999 | Green et al. | |
| 6,086,821 | A | 7/2000 | Lee | |
| 6,180,418 | B1 | 1/2001 | Lee | |
| 6,428,959 | B1 | 8/2002 | Deamer | |
| 6,780,584 | B1 | 8/2004 | Edman et al. | |
| 7,736,889 | B2 | 6/2010 | Rife et al. | |
| 7,744,737 | B1 | 6/2010 | James et al. | |
| 8,324,914 | B2 | 12/2012 | Chen et al. | |
| 8,592,225 | B2 | 11/2013 | Ronaghi et al. | |
| 8,810,787 | B2 | 8/2014 | Van Dorpe et al. | |
| 9,188,560 | B2 | 11/2015 | Liu et al. | |
| 9,816,988 | B1 | 11/2017 | Paik et al. | |
| 2002/0137089 | A1* | 9/2002 | Deamer | G01N 33/48721 435/6.18 |
| 2003/0064699 | A1 | 4/2003 | Olsen | |
| 2004/0038426 | A1 | 2/2004 | Manalis | |
| 2008/0035180 | A1 | 2/2008 | Mutharasan et al. | |
| 2009/0109441 | A1 | 4/2009 | Hartman | |
| 2009/0205977 | A1 | 8/2009 | Shew et al. | |
| 2010/0152057 | A1 | 6/2010 | Lieber et al. | |
| 2010/0243449 | A1 | 9/2010 | Oliver | |
| 2010/0327874 | A1* | 12/2010 | Liu | G01N 27/44791 324/464 |
| 2011/0031123 | A1 | 2/2011 | Schulze et al. | |
| 2011/0036719 | A1 | 2/2011 | Neyts et al. | |
| 2011/0053284 | A1* | 3/2011 | Meller | G01N 33/48721 506/13 |
| 2012/0097539 | A1* | 4/2012 | Qian | G01N 33/48721 977/773 |
| 2013/0048499 | A1 | 2/2013 | Mayer et al. | |
| 2013/0203608 | A1 | 8/2013 | Shim et al. | |
| 2013/0264207 | A1 | 10/2013 | Ju et al. | |
| 2014/0034497 | A1* | 2/2014 | Davis | G01N 27/44791 204/451 |
| 2014/0090981 | A1 | 4/2014 | Paik et al. | |
| 2014/0102901 | A1 | 4/2014 | Javanmard et al. | |
| 2014/0134618 | A1 | 5/2014 | Kokoris et al. | |
| 2014/0158540 | A1* | 6/2014 | Ohura | G01N 27/44791 204/543 |
| 2014/0360890 | A1 | 12/2014 | Mutharasan et al. | |
| 2015/0246146 | A1 | 9/2015 | Agnew et al. | |
| 2015/0344945 | A1* | 12/2015 | Mandell | G01N 27/44743 204/453 |
| 2016/0003798 | A1 | 1/2016 | Paik et al. | |
| 2017/0356904 | A1 | 12/2017 | Paik et al. | |
| 2018/0045668 | A1 | 2/2018 | Paik et al. | |

FOREIGN PATENT DOCUMENTS

| | | | |
|---|---|---|---|
| WO | WO-2008/102120 | A1 | 8/2008 |
| WO | WO-2010/004273 | A1 | 1/2010 |
| WO | WO-2011/027379 | A1 | 3/2011 |
| WO | WO-2013/154999 | A2 | 10/2013 |
| WO | WO-2013/191793 | A1 | 12/2013 |
| WO | WO-2015/100170 | A1 | 7/2015 |
| WO | WO-2015/110777 | A1 | 7/2015 |
| WO | WO-2015/196148 | A1 | 12/2015 |
| WO | WO-2016/059375 | A1 | 4/2016 |
| WO | WO-2016/160131 | A1 | 10/2016 |

OTHER PUBLICATIONS

Baskin, J.M. et al. (2007) "Copper-free click chemistry for dynamic in vivo imaging," PNAS 104(43):16793-16797.

Branton, D. et al. (2008) "The potential and challenges of nanopore sequencing," Nature Biotechnology 26(10):1146-1153.

Brown, E.D. et al. (2016) "Antibacterial drug discovery in the resistance era," Nature 529:336-343.

Chilkoti, A. et al. (1995) "The Relationship Between Ligand-Binding Thermodynamics and Protein-Ligand Interaction Forces Measured by Atomic Force Microscopy," Biophysical Journal 69(5):2125-2130.

Dammer, U. et al. (1996) "Specific Antigen/Antibody Interactions Measured by Force Microscopy," Biophysical Journal 70:2437-2441.

De Jager, W. et al. (2003) "Simultaneous Detection of 15 Human Cytokines in a Single Sample of Stimulated Peripheral Blood Mononuclear Cells," Clinical and Diagnostic Laboratory Immunology 10(1):133-139.

Drummond, T.G. et al. (2003) "Electrochemical DNA sensors," Nature Biotechnology 21(10):1192-1199.

Dudko, O.K. et al. (2007) "Extracting Kinetics from Single-Molecule Force Spectroscopy: Nanopore Unzipping of DNA Hairpins," Biophysical Journal 92(12):4188-4195.

Dunbar, S.A. (2006) "Applications of Luminex xMAP$2122 technology for rapid, high-throughput multiplexed nucleic acid detection," Clinica Chimica Acta 363:71-82.

Ekins, R. et al. (1989) "Development of microspot multi-analyte ratiometric immunoassay using dual fluorescent-labelled antibodies," Analytica Chimica Acta 227:73-96.

Ekins, R.P. (1989) "Multi-analyte immunoassay," Journal of Pharmaceutical & Biomedical Analysis 7(2): 155-168.

Emaminejad, S. et al. (2014) "Multiplexed actuation using ultra dielectrophoresis for proteomics applications: a comprehensive electrical and electrothermal design methodology," Lab on a Chip 14 (2014):2105-2114.

Evans, E. et al. (1997) "Dynamic Strength of Molecular Adhesion Bonds," Biophysical Journal 72(4):1541-1555.

Extended European Search Report in EP Application No. 15810443.0, mailed Dec. 15, 2017.

Final Office Action on U.S. Appl. No. 15/382,364 DTD Nov. 2, 2017.

Final Office Action on U.S. Appl. No. 15/382,364 DTD Dec. 14, 2018.

Fingerova, H. et al. (2007) "Antioxidant capacity of seminal plasma measured by TAS randox," Biomed Pap Fac Univ Palacky Olomouc Czech Repub. 151(1):37-40.

First Office Action issued in Chinese Application No. 201580043723.2 dated Sep. 28, 2018, 32 pages.

Fletcher, M.A. et al. (2009) "Plasma cytokines in women with chronic fatigue syndrome," Journal of Translational Medicine 7:96.

Florin, E-L. et al. (1994) "Adhesion Forces between Individual Ligand-Receptor Pairs," Science 264(5157):415-417.

Gong, H. et al. (2016) "Simple Method To Prepare Oligonucleotide-Conjugated Antibodies and Its Application in Multiplex Protein Detection in Single Cells," Bioconjugate Chemstry 27:217-225.

Houser, B. (2012) "Bio-Rad's Bio-Plex? suspension array system, xMAP technology overview," Archives of Physiology and Biochemistry 118(4):192-196.

(56) References Cited

OTHER PUBLICATIONS

Howorka, S. et al. (2001) "Sequence-specific detection of individual DNA strands using engineered nanopores," Nature Biotechnology 19(7):636-639.
International Search Report and Written Opinion (ISA/US) for International Application No. PCT/US2015/036800, mailed Sep. 14, 2015.
International Search Report and Written Opinion for International Application No. PCT/US2016/017181, mailed Aug. 8, 2016.
International Search Report and Written Opinion for International Application No. PCT/US2017/044252, mailed Oct. 6, 2017.
Invitrogen User Guide. (2017) "SiteClick$2122 Antibody Azido Modification Kit," Pub. No. MAN0017078.
Iqbal, S.M. et al. (2007) "Solid-state nanopore channels with DNA selectivity," Nature Nanotechnology 2(4):243-248.
Javanmard, M. et al. (2012) "Use of Negative Dielectrophoresis for Selective Elution of Protein-Bound Particles," Analytical Chemistry 84:1432-1438.
Juncker, D. et al. (2014) "Cross-reactivity in antibody microarrays and multiplexed sandwich assays: shedding light on the dark side of multiplexing," Current Opinion in Chemical Biology 18:29-37.
Kahng, A.B. (2013) "The ITRS Design Technology and System Drivers Roadmap: Process and Status," DAC'13: 1-6.
Katsanis, S.H. et al. (2013) "Molecular genetic testing and the future of clinical genomics," Nature Reviews, Genetics 14:415-426.
Kazane, S.A. et al. (2012) "Site-specific DNA-antibody conjugates for specific and sensitive immune-PCR," PNAS 109(10):3731-3736.
Lee, G.U. et al. (1994) "Sensing Discrete Streptavidin-Biotin Interactions with Atomic-Force Microscopy," Langmuir 10(2):354-357.
Lee, G.U. et al. (2000) "Implementation of Force Differentiation in the Immunoassay," Analytical Biochemistry 287:261-271.
Ligler, F.S. (2009) "Perspective on Optical Biosensors and Integrated Sensor Systems," Analytical Chemistry 81:519-526.
Liu, H. et al. (2017) "Targeting Alpha-Fetoprotein (AFP)-MHC Complex with CAR T-Cell Therapy for Liver Cancer," Clinical Cancer Research 23(2):478-488.
Liu, Y. et al. (2008) "Effect of electrodiffusion current flow on electrostatic screening in aqueous pores," Journal of Applied Physics 103:084701.
Liu, Y. et al. (2008) "Overcoming the screening-induced performance limits of nanowire biosensors: a simulation study on the effect of electro-diffusion flow," IEDM: 491-494.
Neuman, K.C. et al. (2008) "Single-molecule force spectroscopy: optical tweezers, magnetic tweezers and atomic force microscopy," Nature Methods 5(6):491-505.
Nguyen, G. et al. (2010) "DNA Strands Attached Inside Single Conical Nanopores: Ionic Pore Characteristics and Insight into DNA Biophysics," J Membrane Biol. 239(1-2):105-113.
Non-Final Office Action on U.S. Appl. No. 15/382,364 DTD Oct. 3, 2019.
Notice of Allowability for U.S. Appl. No. 15/451,133, mailed Oct. 19, 2017.
Notice of Allowance for U.S. Appl. No. 15/451,133, mailed Aug. 3, 2017.
Paik, K-H. et al. (2012) "Control of DNA Capture by Nanofluidic Transistors," ACS Nano 6(8):6767-6775.
Relling, M.V. et al. (2015) "Pharmacogenomics in the clinic," Nature 526:343-350.
Rothberg, J.M. et al. (2011) "An integrated semiconductor device enabling non-optical genome sequencing," Nature 475:348-352.
Sano, T. et al. (1992) "Immuno-PCR: Very Sensitive Antigen Detection by Means of Specific Antibody-DNA Conjugates," Science 258:120-122.
Schwenk, J.M. et al. (2010) "Toward Next Generation Plasma Profiling via Heat-induced Epitope Retrieval and Array-based Assays," Molecular & Cellular Proteomics 9.11:2497-2507.
Schwesinger, F. et al. (2000) "Unbinding forces of single antibody-antigen complexes correlate with their thermal dissociation rates," PNAS 97(18):9972-9977.
Sheth, H. et al. (2014) "Point of care testing for improving risk-benefit ratio of aspirin and warfarin," Molecular Cytogenetics 7(Suppl 1):154.
Smith, P.K. et al. (1985) "Measurement of Protein Using Bicinchoninic Acid," Anal. Biochem. 150:76-85.
Spindel, S. et al. (2014) "Evaluation of Optical Detection Platforms for Multiplexed Detection of Proteins and the Need for Point-of-Care Biosensors for Clinical Use," Sensors 14:22313-22341.
Tabard-Cossa, V. et al. (2009) "Single-Molecule Bonds Characterized by Solid-State Nanopore Force Spectroscopy," ACS Nano 3(10):3009-3014.
ThermoFisher Scientific. "IL-8 Human Matched Antibody Pair," retrieved Mar. 6, 2018 (https://www.thermofisher.com/order/catalog/product/CHC1303).
ThermoFisher Scientific. "SiteClick$2122 Antibody Labeling System," retrieved Mar. 6, 2018 (https://www.thermofisher.com/us/en/home/life-science/cell-analysis/labeling-chemistry/protein-and-antibody-chemical-labeling/antibody-protein-labeling-kits/siteclick-labeling.html).
Tighe, P.J. et al. (2015) "ELISA in the multiplex era: Potentials and pitfalls," Proteomics—Clinical Applications. 9:406-422.
Tropini, C. et al. (2007) "Multi-Nanopore Force Spectroscopy for DNA Analysis," Biophysical Journal 92:1632-1637.
US Office Action on 102354-0358 DTD May 24, 2017.
US Office Action on U.S. Appl. No. 15/382,364 DTD Mar. 14, 2017.
US Office Action on U.S. Appl. No. 15/382,364 DTD Apr. 30, 2018.
Van Buggenum, J.A.G.L. et al. (2016) "A covalent and cleavable antibody-DNA conjugation strategy for sensitive protein detection via immune-PCR," Scientific Reports 6:22675.
Wong, J. et al. (1999) "Direct force measurements of the streptavidin-biotin interaction," Biomolecular Engineering. 16:45-55.
Yan, J. et al. (2014) "A Universal Approach to Prepare Reagents for DNA-Assisted Protein Analysis," Plos One 9(9):e108061, 1-8.
You, W.W. et al. (1997) "3-(4-Carboxybenzoyl)quinoline-2-carboxaldehyde, a Reagent with Broad Dynamic Range for the Assay of Proteins and Lipoproteins in Solution," Anal Biochem. 244:277-282.
Zuker, M. (2003) "Mfold web server for nucleic acid folding and hybridization prediction," Nucleic Acids Research 31(13):3406-3415.
Office Action on Canadian Application No. 2951945 dated Jun. 3, 2021.

* cited by examiner

1205

1206

1400

1401

1511 $$V_C = V_D\left(\frac{R_{GS}}{R_{GS}+R_{GD}}\right), V_S = 0$$

1512 $$V_G = \frac{C_{GS}V_S + C_{GD}V_D + C_C V_C}{C_{GS}+C_{GD}+C_C}$$

APPARATUSES AND METHODS FOR DETERMINING ANALYTE CHARGE

CROSS-REFERENCE TO RELATED APPLICATIONS

This application is a Continuation Application of U.S. application Ser. No. 15/382,364, filed Dec. 16, 2016, which claims priority to Continuation Application of International Application No. PCT/US2015/036800, filed Jun. 19, 2015, which claims priority to U.S. Provisional Application No. 62/014,595, filed Jun. 19, 2014, and with Appendices A-C; the content of each of which is incorporated herein by reference in its entirety.

STATEMENT AS TO FEDERALLY SPONSORED RESEARCH

This invention was made with the support of the United States government under Contract number NIH P01 HG000205 by the National Institutes of Health (NIH).

BACKGROUND

There is a great deal of interest in the field of biotechnology on nucleic acid sensors that can replace the currently popular optics-based biosensors. While there has been numerous theoretical advances in nucleic acids research, the cost of performing the methods developed (whether for diagnosis of a patient's ailment or investigation of a pathogenic trait) frequently hamper their adoption into clinical settings. For example, while the cost of human genome sequencing has been dramatically reduced from $3 billion to $20 thousand, it is still far too expensive to be used in a routine clinical environment. The optics-based sensing (that tends to be time consuming to operate, needs modified fluorescing reagents, requires bulky optical sources and needs costly imaging equipment) is seen as a major bottleneck in lowering the cost of genomics. While the integrated electrical sensors seem to provide many advantages over the optical ones, recent approaches either have limitations in manufacturability or have shown poor robustness.

SUMMARY

Recognized herein is the need for improved sensors for detecting analytes such as nucleic acids (e.g., that are more sensitive, more robust, and/or more easily manufactured). In various aspects, the present disclosure provides such sensors and methods for using the sensors, for example, to sequence a nucleic acid molecule.

Various aspects of the present disclosure are directed toward a sensor for detecting a charged analyte and methods of using the sensor. The sensor includes a fluidic chamber having electrically opposing portions (e.g., a top portion and a bottom portion) with a membrane between. The membrane provides a pore suitable for the passage of an electrolyte between the electrically opposing portions (e.g., from the top portion to the bottom portion) of the fluidic chamber and having at least one charged analyte tethered in proximity to the pore; a first circuit configured to apply an electric field capable of passing the electrolyte through the pore and pulling the at least one charged analyte into the pore. The sensor further includes a second circuit configured to measure a signal indicative of the charge of the at least one charged analyte upon the at least one charged analyte being pulled into the pore.

The second circuit optionally includes a sensing electrode for measuring the signal, wherein the sensing electrode is located at a distance away from the at least one charged analyte. The distance may be at least 2-times a Debye length associated with the at least one charged analyte. The Debye length is calculated using the Debye-Hückel equation: $\Lambda_D \sim \sqrt{\varepsilon kT/C_0}$, wherein $\Lambda_D$=Debye length, ε=electric constant, k=Boltzman constant, T=temperature, and $C_0$=ionic concentration. In various embodiments, respective sizes or diameters (and/or shapes) of the pore can vary as needed to pass certain types (having corresponding sizes) of charged analytes. As one example, certain charged analytes may be appropriate for pores sized between 25 nm and 2000 nm in diameter as used with a membrane having a thickness between 50 nm and 3 μm. For other analytes such as smaller-sized analytes, the pore has a diameter of at least about 10 nanometers (nm). The electric field may have a strength of at least about $10^5$ Volts per meter (V/m). The at least one charged analyte may have an electrical double layer (EDL) surrounding it and the electric field may be capable of de-screening the EDL. Further, the membrane and walls of the pore may have an EDL surrounding them and the electric field may be capable of de-screening the EDL. The electric field may be capable of generating a non-equilibrium transport condition. The membrane may be electrically insulating. Further, the membrane may be comprised of graphene, alumina ($Al_2O_3$), silicon dioxide ($SiO_2$) or silicon nitride ($Si_3N_4$) (e.g., which are and/or can be electrically insulating material). The first circuit may include a first electrode in a first electrically opposing portion (e.g., the top portion) of the fluidic chamber and a second electrode in a second electrically opposing portions (e.g., the bottom portion) of the fluidic chamber. The second circuit may include an electrode embedded in the membrane in proximity to the pore. The second circuit may include an amplifier capable of amplifying the signal. The amplifier may be within about 5000 μm from the pore. The signal may be linearly proportional to the charge of the at least one charged analyte. The at least one charged analyte may be a nucleic acid molecule. Further, the at least one charged analyte may have a net charge of at least about 40 $e^-$. However, the at least one charged analyte may have a net charge lower or higher than about 40 $e^-$. The electrolyte may have an ionic strength of about 100 μM to about 1M. Further, the at least one charged analyte can be tethered in proximity to the pore by a molecular structure and/or be being immobilized. Further, the sensor may have a plurality of pores into which the plurality of charged analytes are pulled. Further, the plurality of charged analytes may be clonal. In another aspect, a device is disclosed in which the device has a plurality of the sensors detailed herein.

Other related embodiments are directed to a kit for detecting a charged analyte. The kit includes at least one charged analyte, and a sensor. The sensor includes a fluidic chamber having electrically opposing portions (e.g., a top portion and a bottom portion) with a membrane between, the membrane providing (or defining) a pore suitable for the passage of an electrolyte between the electrically opposing portions (e.g., from the top portion to the bottom portion) of the fluidic chamber and having the at least one charged analyte tethered in proximity to the pore (e.g., sufficiently proximal to the pore for the electrical field interactions described herein). The sensor also includes a first circuit configured to apply an electric field capable of passing the electrolyte through the pore and pulling the at least one charged analyte into the pore. The sensor also includes a second circuit configured to measure a signal indicative of the charge of the at least one charged analyte upon the at least one charged analyte being pulled into the pore. The membrane may be electrically insulating. Further, the membrane may be comprised of graphene, alumina ($Al_2O_3$), silicon dioxide ($SiO_2$) or silicon nitride ($Si_3N_4$). The first circuit may include a first electrode in a first electrically opposing portion (e.g., the top portion) of the fluidic chamber and a second electrode in the second electrically opposing portion (e.g., the bottom portion) of the fluidic chamber. The second circuit may include an electrode embedded in the membrane in proximity to the pore. The second circuit may include an amplifier capable of amplifying the signal. The amplifier may be within about 5000 μm from the pore. The signal may be linearly proportional to the charge of the at least one charged analyte. The at least one charged analyte may be a nucleic acid molecule. Further, the at least one charged analyte may have a net charge of at least about 40 $e^-$. However, the at least one charged analyte may have a net charge lower or higher than about 40 $e^-$. The electrolyte may have an ionic strength of about 100 μM to about 1M. Further, the sensor may have a plurality of pores into which the plurality of charged analytes are pulled. Further, the plurality of charged analytes may be clonal.

In accordance with other related embodiments, aspects of the present disclosure are directed to a method for detecting a charged analyte. The method includes providing a fluidic chamber having electrically opposing portions (e.g., a top portion and a bottom portion) between a membrane, one of the electrical opposing portions (e.g., the top portion) having an electrolyte, the membrane providing a pore suitable for the passage of an electrolyte between the electrically opposing portions (e.g., from the top portion to the bottom portion) of the fluidic chamber, and having at least one charged analyte tethered in proximity to the pore. The method further includes applying an electric field to pass the electrolyte through the pore and pull the at least one charged analyte into the pore; and measuring a signal indicative of the charge of the at least one charged analyte upon the at least one charged analyte being pulled into the pore. The method optionally includes the at least one charged analyte being pulled to a position in proximity to a periphery of the pore. In this method, the first circuit may apply the electric field. The second circuit may measure the signal.

Another related aspect of the disclosure is directed to a method that includes providing a fluidic chamber having electrically opposing portions (e.g., a top portion and a bottom portion) between a membrane (e.g., separated by a membrane), where one of the electrically opposing portions (e.g., the top portion) includes an electrolyte, the membrane providing a pore suitable for the passage of an electrolyte between the electrically opposing portions (e.g., from the top portion to the bottom portion) of the fluidic chamber, tethering the at least one nucleic acid molecule in proximity to the pore; hybridizing a nucleic acid primer to the at least one nucleic acid molecule adjacent to a first position of the at least one nucleic acid molecule; applying an electric field to pass the electrolyte through the pore and pull the at least one nucleic acid molecule into the pore; measuring a signal indicative of the charge of the at least one nucleic acid molecule and the nucleic acid primer, and extending the nucleic acid primer with a nucleotide complimentary to the next position of the at least one nucleic acid molecule, thereby increasing the magnitude of the charge of the nucleic acid primer. The foregoing steps related to applying, measuring, and extending may be repeated to sequence the nucleic acid molecule. The first circuit may apply the above-mentioned electric field. The second circuit may measure the above-mentioned signal.

Another related aspect is directed to a method for detecting a nucleic acid molecule. The method includes providing a fluidic chamber having a top portion and a bottom portion separated by a membrane, the top portion including an electrolyte, the membrane providing a pore suitable for the passage of the electrolyte from the top portion to the bottom portion of the fluidic chamber, tethering at least one charged analyte in proximity to the pore; applying an electric field to pass the electrolyte through the pore and pull the at least one charged analyte into the pore; and measuring a signal indicative of the charge of the at least one charged analyte upon the at least one charged analyte being pulled into the pore. The first circuit may apply the above-mentioned electric field. The second circuit may measure the above-mentioned signal.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forthwith particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1A:
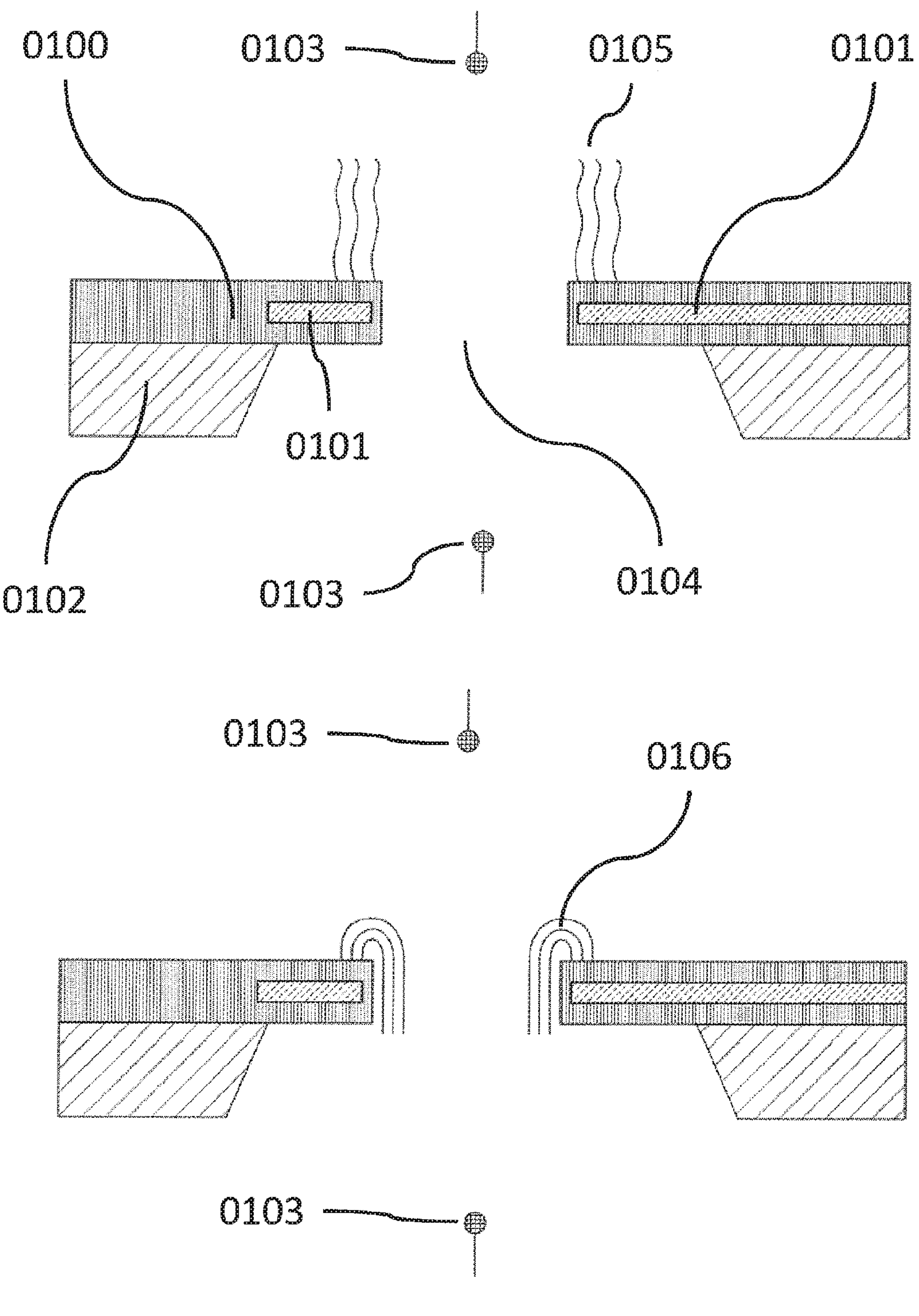
FIG. 1A shows an example of a cross-sectional profile view of a sensor of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The example sensing method of the present disclosure is based on delivery of charged analytes to the charge sensor via an applied electric field which also suppresses the electrical charge-shielding in the confined geometry of a pore through a thin (ca. 100 nm) membrane. Because the electrostatic potential drop across the device is dominated by the pore, high electric fields (ca. $10^6$~$10^7$ V/m) can be easily generated inside it. The resulting ionic current through the pore can disrupt the electrostatic screening of the molecules in the sensing region, making it possible to detect their charge hundreds of nanometers away. This is a surprising effect since under equilibrium conditions the Debye-Hückel screening model predicts that charge sensing is only possible within a distance of a few Debye lengths from the target analytes (Debye length, $\lambda_D$, is ~1 nm at physiological conditions).

In the presence of ionic current flow in nano-confined geometries, the effective ionic screening length can dramatically increase. By applying electrical biasing across aqueous pores, electro-diffusion current flow is present, particularly along the radial direction due to the presence of the charged analytes. This current significantly suppresses the charge-screening effect. This finding serves as the operation principle of our proposed devices, which can sense the charge of an analyte (e.g., biomolecule) at distances of about 10 to about 100 times the Debye length, $\lambda_D$.

Two major challenges to charge sensing via electronic charge sensors in an aqueous environment include excessive confinement requirements due to the electric double layer's (EDL) shielding of the analyte charge and difficulty of capturing the analyte for sensing. Aspects of the present disclosure are directed to a non-equilibrium transport phenomenon along with a strategic immobilization of analytes to circumvent the challenges for charge-based sensors in aqueous environments. Novel physics enable utilization of devices for various applications. Because charge is an inherent characteristic of nucleic acids, various aspects of the present disclosure enable fast, label-free detection of nucleic acids for cost-effective analysis. Aspects of the present disclosure which are directed toward optics-based methods of sensing can dramatically reduce the entry barrier to perform nucleic acids and protein research as compared with radioisotope labeled analyte sensing. The regulatory simplification from not using radiation sources has provided a plethora of commercial analysis tools (e.g., next generation sequencing, DNA microarray, real-time PCR, etc.). Aspects of the present disclosure which are directed toward electronic methods of sensing can reduce the entry barrier to perform nucleic acids and protein research, in a manner similar to the effect of the transition from radioisotope sensing to optics-based sensing.

Various aspects of the present disclosure are directed toward an integrated charge sensor chip that can include a source follower (SF) amplifier and a sense electrode in close proximity resting on a thin $Si_xN_y$ membrane. Such an integrated charge sensor can be a passive (non-active sensor). In some cases, the sensor is an active sensor (e.g., having an integrated signal amplifier).

One aspect is directed to a sensor for detecting a charged analyte. The term "analyte" includes, but is not limited to, a nucleic acid as understood by those persons skilled in the art. The sensor includes a fluidic chamber having electrically opposing portions (e.g., a top portion and a bottom portion) separated by a membrane. The membrane includes a pore suitable for the passage of an electrolyte, such as from the top portion to the bottom portion of the fluidic chamber. The sensor further includes a first circuit configured to apply an electric field capable of passing the electrolyte through the pore and pulling the at least one charged analyte into the pore. The sensor further includes a second circuit configured to measure a signal indicative of the charge of the at least one charged analyte when the at least one charged analyte is pulled into the pore. In a number of embodiments, the at least one charged analyte is tethered, in proximity to the pore, concurrently with the pulling of the at least one charged analyte into the pore.

The second circuit may include a sensing electrode for measuring the signal, wherein the sensing electrode is located at a distance away from the at least one charged analyte. The distance may be at least 2-times a Debye length associated with the at least one charged analyte. The Debye length is calculated using the Debye-Hückel equation: $\Lambda_D \sim \sqrt{\varepsilon kT/C_0}$, wherein $\Lambda_D$=Debye length, ε=electric constant, k=Boltzman constant, T=temperature, and $C_0$=ionic concentration. The pore, in some embodiments, has a diameter of at least about 10 nanometers (nm). The electric field may have a strength of at least about $10^5$ Volts per meter (V/m). The at least one charged analyte may have an electrical double layer (EDL) surrounding it and the electric field may be capable of de-screening the EDL. Further, the membrane and walls of the pore may have an EDL surrounding them and the electric field may be capable of de-screening the EDL. The electric field may be capable of generating a non-equilibrium transport condition. The membrane may be electrically insulating. Further, the membrane may include graphene, alumina ($Al_2O_3$), silicon dioxide ($SiO_2$) or silicon nitride ($Si_3N_4$). The first circuit may include a first electrode in the top portion of the fluidic chamber and a second electrode in the bottom portion of the fluidic chamber. The second circuit may include an electrode embedded in the membrane in proximity to the pore. The second circuit may include an amplifier capable of amplifying the signal. The amplifier may be within about 5000 μm from the pore. The signal may be linearly proportional to the charge of the at least one charged analyte. The at least one charged analyte may be a nucleic acid molecule. Further, the at least one charged analyte may have a net charge of at least about 40 $e^-$. However, the at least one charged analyte may have a net charge lower or higher than about 40 $e^-$. The electrolyte may have an ionic strength of about 100 μM to about 1M. Further, the sensor may include a plurality of charged analytes that are tethered in proximity to the pore. Further, the sensor may have a plurality of pores into which the plurality of charged analytes are pulled. Further, the plurality of charged analytes may be clonal. In another aspect, a device is disclosed in which the device has a plurality of the sensors detailed herein.

Another related aspect is directed to a kit for detecting a charged analyte. The kit includes at least one charged analyte, and a sensor. The sensor includes a fluidic chamber having a top portion and a bottom portion separated by a membrane, the membrane includes a pore suitable for the passage of an electrolyte from the top portion to the bottom portion of the fluidic chamber. The sensor also includes a first circuit configured to apply an electric field capable of passing the electrolyte through the pore and pulling the at least one charged analyte into the pore (e.g., when the at least one charged analyte is tethered in proximity to the pore). The sensor also includes a second circuit configured to measure a signal indicative of the charge of the at least one charged analyte upon the at least one charged analyte being pulled into the pore. The membrane may be electrically insulating. Further, the membrane may be comprised of graphene, alumina ($Al_2O_3$), silicon dioxide ($SiO_2$) or silicon nitride ($Si_3N_4$). The first circuit may include a first electrode in the top portion of the fluidic chamber and a second electrode in the bottom portion of the fluidic chamber. The second circuit may include an electrode embedded in the membrane in proximity to the pore. The second circuit may include an amplifier capable of amplifying the signal. The amplifier may be within about 5000 μm from the pore. The signal may be linearly proportional to the charge of the at least one charged analyte. The at least one charged analyte may be a nucleic acid molecule. Further, the at least one charged analyte may have a net charge of at least about 40 $e^-$. However, the at least one charged analyte may have a net charge lower or higher than about 40 $e^-$. The electrolyte may have an ionic strength of about 100M to about 1M. Further, the sensor may include a plurality of charged analytes that are tethered in proximity to the pore. Further, the sensor may have a plurality of pores into which the plurality of charged analytes are pulled. Further, the plurality of charged analytes may be clonal.

Another related aspect is directed to a method for detecting a charged analyte. The method involves providing a fluidic chamber having a top portion and a bottom portion separated by a membrane, the top portion includes an electrolyte, the membrane includes a pore suitable for the passage of an electrolyte from the top portion to the bottom portion of the fluidic chamber. The method further involves tethering at least one charged analyte in proximity to the pore; applying an electric field to pass the electrolyte through the pore and pull the at least one charged analyte into the pore; and measuring a signal indicative of the charge of the at least one charged analyte upon the at least one charged analyte being pulled into the pore. The method may involve the at least one charged analyte being pulled to a position in proximity to a periphery of the pore. In this method, the first circuit may apply the electric field. The second circuit may measure the signal.

The pore can have any suitable thickness, including a thickness (e.g., a thickness of the membrane and sensing electrode) of about 10 nanometers (nm), about 20 nm, about 40 nm, about 60 nm, about 80 nm, about 100 nm, about 125 nm, about 150 nm, about 200 nm, about 250 nm, about 300 nm, about 350 nm, about 400 nm, about 500 nm, about 600 nm, about 800 nm, about 1 micrometer (μm), about 2 μm, about 4 μm, about 6 μm, about 8 μm, about 10 μm, about 20 μm, about 40 μm, about 60 μm, about 80 μm, about 100 μm, about 200 μm, about 400 μm, about 600 μm, about 800 μm, about 1000 μm, or more. In some embodiments, the pore has a thickness (which can also be referred to as a depth) of at least about 10 nanometers (nm), at least about 20 nm, at least about 40 nm, at least about 60 nm, at least about 80 nm, at least about 100 nm, at least about 125 nm, at least about 150 nm, at least about 200 nm, at least about 250 nm, at least about 300 nm, at least about 350 nm, at least about 400 nm, at least about 500 nm, at least about 600 nm, at least about 800 nm, at least about 1 micrometer (μm), at least about 2 μm, at least about 4 μm, at least about 6 μm, at least about 8 μm, at least about 10 μm, at least about 20 μm, at least about 40 μm, at least about 60 μm, at least about 80 μm, at least about 100 μm, at least about 200 μm, at least about 400 μm, at least about 600 μm, at least about 800 μm, or at least about 1000 μm. In some embodiments, the pore has a thickness of at most about 10 nanometers (nm), at most about 20 nm, at most about 40 nm, at most about 60 nm, at most about 80 nm, at most about 100 nm, at most about 125 nm, at most about 150 nm, at most about 200 nm, at most about 250 nm, at most about 300 nm, at most about 350 nm, at most about 400 nm, at most about 500 nm, at most about 600 nm, at most about 800 nm, at most about 1 micrometer (μm), at most about 2 μm, at most about 4 μm, at most about 6 μm, at most about 8 μm, at most about 10 μm, at most about 20 μm, at most about 40 μm, at most about 60 μm, at most about 80 μm, at most about 100 μm, at most about 200

μm, at most about 400 μm, at most about 600 μm, at most about 800 μm, or at most about 1000 μm.

As discussed above, the pore can have any diameter suitable for passing and acting on the charged analyte, for example, with a larger/smaller pore being suitable for a larger/smaller charged analyte (similarly, a 10 nm pore diameter can suitable for a charged DNA/RNA analyte, 25 nm pore diameter for a charged peptide analyte, 50 nm for a charged protein/virus analyte, 1 um for a charged bacteria analyte, 10 um for a charged blood cell analyte, etc.).

Various aspects of the present disclosure are directed toward integrated, manufacturable, solid-state charge sensors for example, sequencing and DNA microarray applications. For instance, aspects of the present disclosure are directed toward apparatuses, methods and systems that include a fluidic chamber having a top portion and a bottom portion that hold charged analytes, for example, biological molecules. Further, the apparatuses, methods and systems can include a membrane separating the top portion and the bottom portion of the fluidic chamber. The membrane includes an opening to provide a pathway between the top portion and the bottom portion of the fluidic chamber. Additionally, the apparatuses, methods and systems can include a first circuit that applies an electric field to tether a cluster of the biological molecules. Further, the apparatuses, methods and systems can include a sensor and an integrated circuit that determine a charge of the biological molecules while the cluster of the biological molecules are tethered.

In certain embodiments, the charged analytes are one or more of DNA molecules and RNA molecules. Additionally, in certain embodiments, the charged analytes are one or more of inorganic toxins (e.g., cadmium, fluorides, mercury, lead, arsenic, toxic element salts), drugs, peptides, proteins, other toxins, including organic toxins, fungal spores, bacteria, viruses, heavy metals, and other similar charged analytes. Other embodiments of the present disclosure are further characterized as having an exterior portion of the membrane that includes a plurality of adapters which provide immobilization to be used alone or in conjunction with other methods such as solid-phase amplification of the charge analyte sensed by the sensor and the integrated circuit. Additionally, in certain embodiments, an exterior portion of the membrane includes a plurality of adapters that provide solid-phase amplification to create a clonal DNA cluster. Further, a polymerase chain reaction (PCR) primer can be attached to the tail end of the DNA.

Certain embodiments of the present disclosure include a membrane and walls of the opening that form an electric double layer (EDL). In such embodiments, the first circuit generates a non-equilibrium transport condition for descreening of the EDL. In other embodiments, the first circuit pivots the anchored charged analyte, for example a DNA molecule, into the pore in response to the electric field. Additionally, the sensor and an integrated circuit can determine the charge of the charged analytes to sense base incorporations of the charged analytes. Further, the first circuit can also include a cathode and an anode in the fluidic chamber to apply the electric field. One of the anode and the cathode is in the top portion of the fluidic chamber, and the other of the anode and the cathode is in the bottom portion of the fluidic chamber. In other embodiments, the first circuit immobilizes the cluster of the charged analytes such that the charged analytes are separated away from the walls of the pore, and the sensor and an integrated circuit are configured and arranged to determine the charge of the charged analytes. Additionally, certain embodiments can include an array of biological sensing devices. Aspects of the present disclosure can replace any sensing that is currently done optically, chemically or radiologically. Additionally, applications include but are not limited to DNA, RNA or protein sequencing, DNA microarray, peptide microarray and immunoassay.

Example applications for the sensors of the present disclosure include nucleic acid sequencing and nucleic acid microarrays.

Many of the sequencing technologies are based on sequencing-by-synthesis (SBS). The majority of the methods are based on polony sequencing. The SBS reaction appears as follows:

(Eq. 1)

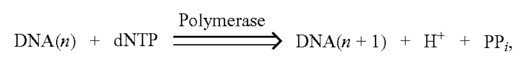

$$DNA(n) + dNTP \xrightarrow{\text{Polymerase}} DNA(n+1) + H^+ + PP_i,$$

where DNA(n) is a DNA molecule with n bases, dNTP is the deoxynucleotide triphosphate and $PP_i$ is the pyrophosphate. Thus, there are three items that can be detected by varieties of sensors for SBS. The addition of the base itself, the proton released during synthesis, and the pyrophosphate released during synthesis. A polony can comprise 100 or more identical copies of a DNA molecule to be sequenced. The multiplexed signal given off by the identical individual DNA molecules being synthesized in a polony in parallel can enhance the integrity of calling (reading) a base.

Based on the solid-phase PCR amplification (bridge amplification), a sequencing platform can use optics to detect the addition of a fluorescently modified base (the increase of DNA(n) to DNA(n+1)). While the modification is necessary for DNA that does not naturally fluoresce, such modification can disrupt the polymerase enzyme's natural functioning and result in increased erroneous incorporation, which statistically occurs in parts of the polony. Once such erroneous incorporations occur, the molecule no longer produces the right signal and contributes to read error of that entire polony. When a sufficient number of DNA molecules in a polony have been corrupted (i.e., is "off phase"), the polony loses the ability to accurately call a base. This can limit the read length to between about 100 and about 300 bases. Further, the optical sources are bulky and the cameras acquiring the images of sequencing results can be slow and produce large data files. The recent developments in optical detection have been limited by incremental improvements in performance, signifying its mature developmental status.

Pyrosequencing detects the release of the pyrophosphate, a byproduct of the synthesis reaction (see: Eq. 1 herein). It is an optics-based technology where a series of reactions are done in microfluidically-confined reaction chambers to observe via bioluminescence from the presence of the pyrophosphate. Challenges can arise from difficulty scaling the signal transduction from the reaction wells to the sensor, for which bundles of fiber-optic cables can be used. However, the pyrosequencing synthesis reaction does not require modified reagents. The result is a resilience to phasing error with read length being 1000 bases or more, which is an order of magnitude larger than the techniques that have surpassed pyrosequencing in popularity.

Solid state pH sensors have also been used to detect the proton, $H^+$ ion, released from polonies after base incorporation. Because the sensor is based on solid-state devices sequencing technology, it is dramatically faster than that of the optical sensors. However, since it is the pH that is sensed, each reagent's pH must be carefully calibrated and the reaction chamber cannot be strongly buffered. This can result in a delicate initialization process, which is time consuming and prone to failure. The local pH change in and around a sensor can also be transient as protons diffuse away and the synthesis result cannot typically be accessed multiple times, resulting in a fixed window upon which data must be gathered. Further, since pH-based sensors detect a byproduct of a specific molecular biological event in DNA synthesis, SBS can be accomplished.

By definition, pH sensors operate on the logarithmic nature of pH. Solid state sensors used for pH detection can be based on the Ion Sensitive Field-Effect Transistor (ISFET) technology. The ISFETs have a linear output response to change in pH (ca. 50 mV/pH). The pH depends logarithmically on the synthesis of a nucleotide. Miniaturization of device dimensions is a frequently used method of cost reduction and performance increase in semiconductor microfabrication. The pH-based method of sequencing has a very visible disadvantage in its poor accuracy determining the lengths of homopolymers which occur randomly in DNA sequences. To ensure that homopolymers of various lengths are distinguishable, the pH sequencing method can require a high number of clonal DNA molecules in the sensors, which interfere with the ability to miniaturize them. Thus, it is difficult to use the traditional method of miniaturization to gain performance increase and cost-effectiveness in pH-based sequencing.

Long-ranged interaction (e.g., greater than about 100 nm) can be exploited for both sensing and actuating charged biomolecules including nucleic acids. Various sensors, in accordance with the present disclosure, detect the charge in the phosphate backbone. In some embodiments, electrical solid-state sensors enable a fast read operation for nucleic acid sequencing and/or microarray. For nucleic acid sequencing, unlike sensing pH, sensing the charge in the phosphate backbone can result in a linear response to the number of bases incorporated, thus not suffering from reduced accuracy in determining homopolymer sequence. The signal is also permanently fixed and can be accessed multiple times for error reduction (e.g., 2, 3, 4, 5, 6, 7, 8, 9, 10, or more times).

Since nucleic acids have a net one electron ($1e^-$) charge in their phosphate backbone, the net charge on a nucleic acid molecule is directly proportional to the number of bases in it. Thus, the ability to monitor the amount of charge on a nucleic acid molecule can enable monitoring of the number of bases in a molecule. The knowledge about the number of bases in a DNA or RNA molecule, in turn, enables the detection of synthesis events for sequencing or hybridization events for microarrays.

Reading charges in the phosphate backbone that is inherent in the nucleic acid molecules themselves can greatly simplify the sequencing chemistry. Accordingly, charge sensors, consistent with various aspects of the present disclosure, may not require modified reagents (e.g., nucleotide, polymerase) or additional reagents for detection (e.g., ATP sulfurylase, luciferase). Thus, the charge sensors described herein can offer simple replacement of current sensing methods while maintaining various advantages. Additionally, the sequencing platform based on the sensor described herein can have the long read length of pyrosequencing, the speed of solid-state sequencing, and the robustness traditionally associated with optical sensing. Thus, by using a manufacturable solid state sensor that is capable of directly detecting changes in the inherent charge of a DNA molecule many of the issues that plague current and emerging next-generation sequencing platforms can be circumvented. The solid state integrated charge sensor can function independent of pH, can read the base incorporation events quickly, have efficient data storage, and also have a less expensive scaling cost with better homopolymer resolution.

A number of embodiments are directed to a method. The method includes providing a fluidic chamber having a top portion and a bottom portion separated by a membrane, the top portion includes an electrolyte, the membrane includes a pore suitable for the passage of an electrolyte from the top portion to the bottom portion of the fluidic chamber; tethering at least one nucleic acid molecule in proximity to the pore; hybridizing a nucleic acid primer to the at least one nucleic acid molecule adjacent to a first position of the at least one nucleic acid molecule; applying an electric field to pass the electrolyte through the pore and pull the at least one nucleic acid molecule into the pore; measuring a signal indicative of the charge of the at least one nucleic acid molecule and the nucleic acid primer, and extending the nucleic acid primer with a nucleotide complimentary to the next position of the at least one nucleic acid molecule, thereby increasing the magnitude of the charge of the nucleic acid primer. The foregoing steps related to applying, measuring, and extending may be repeated to sequence the nucleic acid molecule. The first circuit may apply the above-mentioned electric field. The second circuit may measure the above-mentioned signal.

In other related embodiments, a method includes detecting a nucleic acid molecule. The method includes providing a fluidic chamber having a top portion and a bottom portion separated by a membrane, the top portion includes an electrolyte, the membrane includes a pore suitable for the passage of the electrolyte from the top portion to the bottom portion of the fluidic chamber, tethering at least one charged analyte in proximity to the pore; applying an electric field to pass the electrolyte through the pore and pull the at least one charged analyte into the pore; and measuring a signal indicative of the charge of the at least one charged analyte when the at least one charged analyte is pulled into the pore. The first circuit may apply the above-mentioned electric field. The second circuit may measure the above-mentioned signal.

Figure 1B:
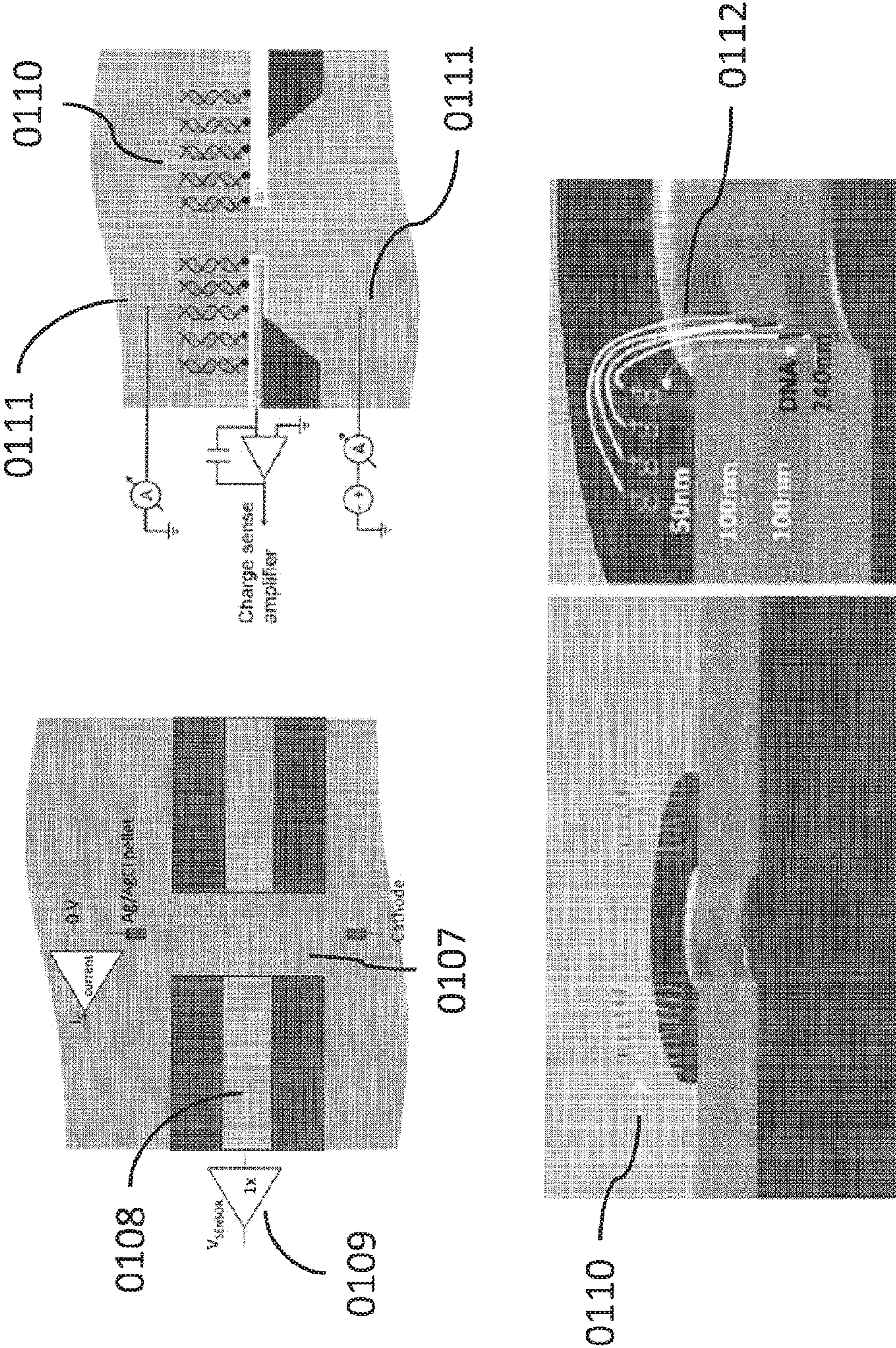
FIG. 1B shows additional examples of the sensor of the present disclosure.

Turning now to the figures, FIG. 1A shows an example schematic of a sensor in profile view consistent with various aspects of the present disclosure. The sensor can be used for detection of nucleic acids 0105. The sensor comprises an electrode 0101 embedded in a pore 0104 disposed on a substrate 0102, which can be made by photolithography. In some cases, the pore has a diameter of between about 100 and about 300 nm. The signal from the electrode can be read through a thin-film unity gain source follower (SF) amplifier integrated in close proximity to the sensor (not shown, see FIG. 7, FIG. 11 and FIG. 13 for examples). The nucleic acid molecules to be detected can be immobilized on the sensor such that by applying the appropriate bias on the bias electrodes 0103, the negatively charged nucleic acid can be drawn into the pore for sensing 0106. The bias electrodes can be Ag/AgCl, Pt or Au electrodes. In some cases, the membrane 0100 (e.g., about 100 to about 400 nm thick) provides the electrical confinement to generate the non-equilibrium transport condition necessary for de-screening of the electrical double layer (EDL). FIG. 1B shows additional drawings of the sensor of the present disclosure. The pore 0107 has an embedded electrode 0108 connected to an amplifier 0109. The nucleic acid molecules 0110 to be detected can be immobilized on the sensor such that by applying the appropriate bias on the bias electrodes 0111, the negatively charged nucleic acid can be drawn into the pore for sensing 0112.

Figure 2:
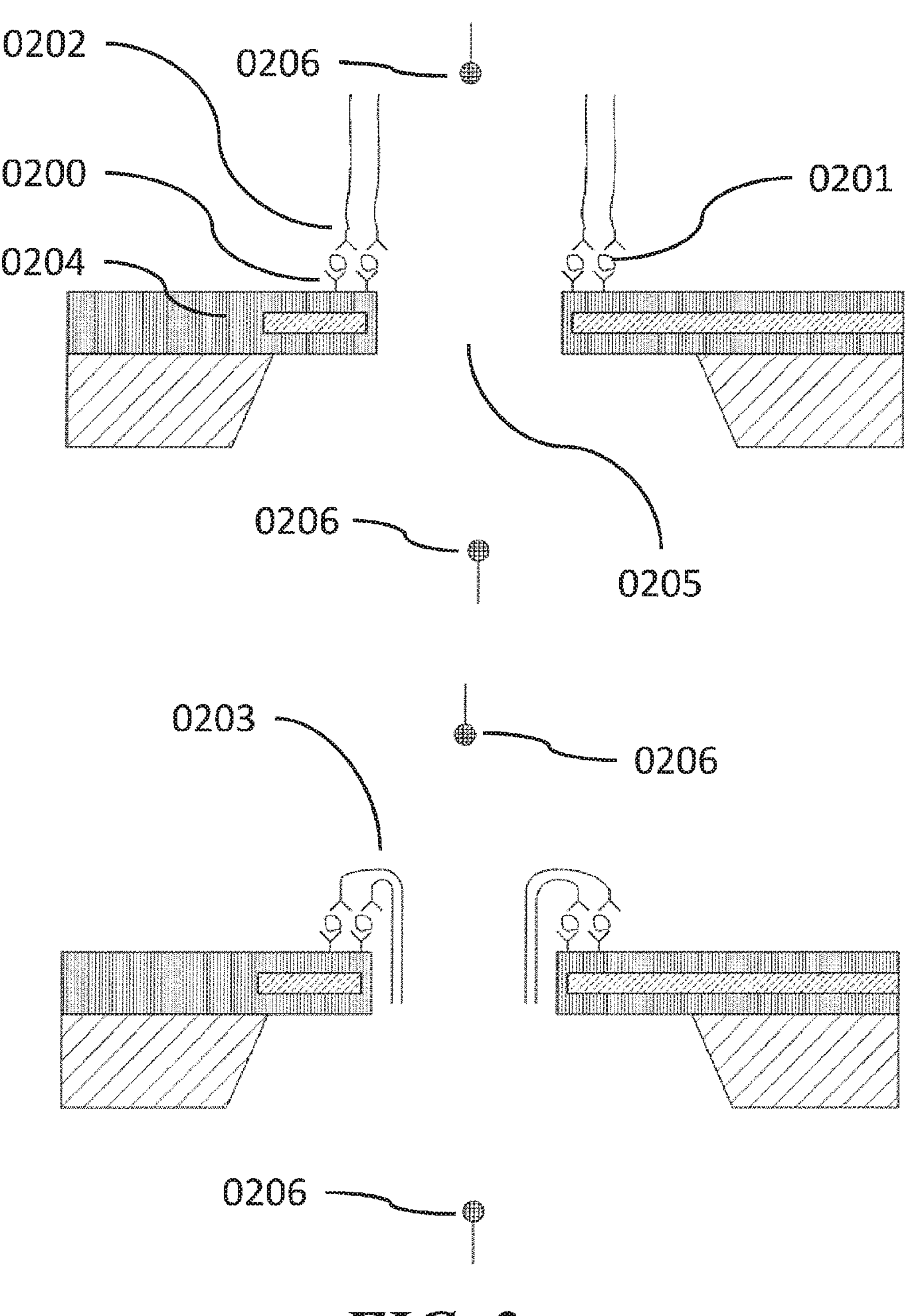
FIG. 2 shows an example of using the sensor of the present disclosure to perform a sandwich immunoassay.

The sensor of the present disclosure can be used to detect any analyte such as nucleic acids, proteins, carbohydrates, metabolites, cells, organic or inorganic molecules, drugs, and/or drug candidates. The analyte itself need not have a charge. For example, FIG. 2 shows an example of using the sensor for a sandwich immunoassay. A probe antibody 0200 can be immobilized on the surface of the membrane 0204, near the pore 0205 entrance. The analyte (target antigen) 0201 can bind to the probe antibody, which is also bound to the secondary antibody 0202. The secondary antibody 202 can include an antibody conjugated with a charged tag that can be pulled into the pore 0203 for sensing when a trans-membrane bias is applied by the bias electrodes 0206. In some cases, the charged tag is a nucleic acid molecule.

Figure 3:
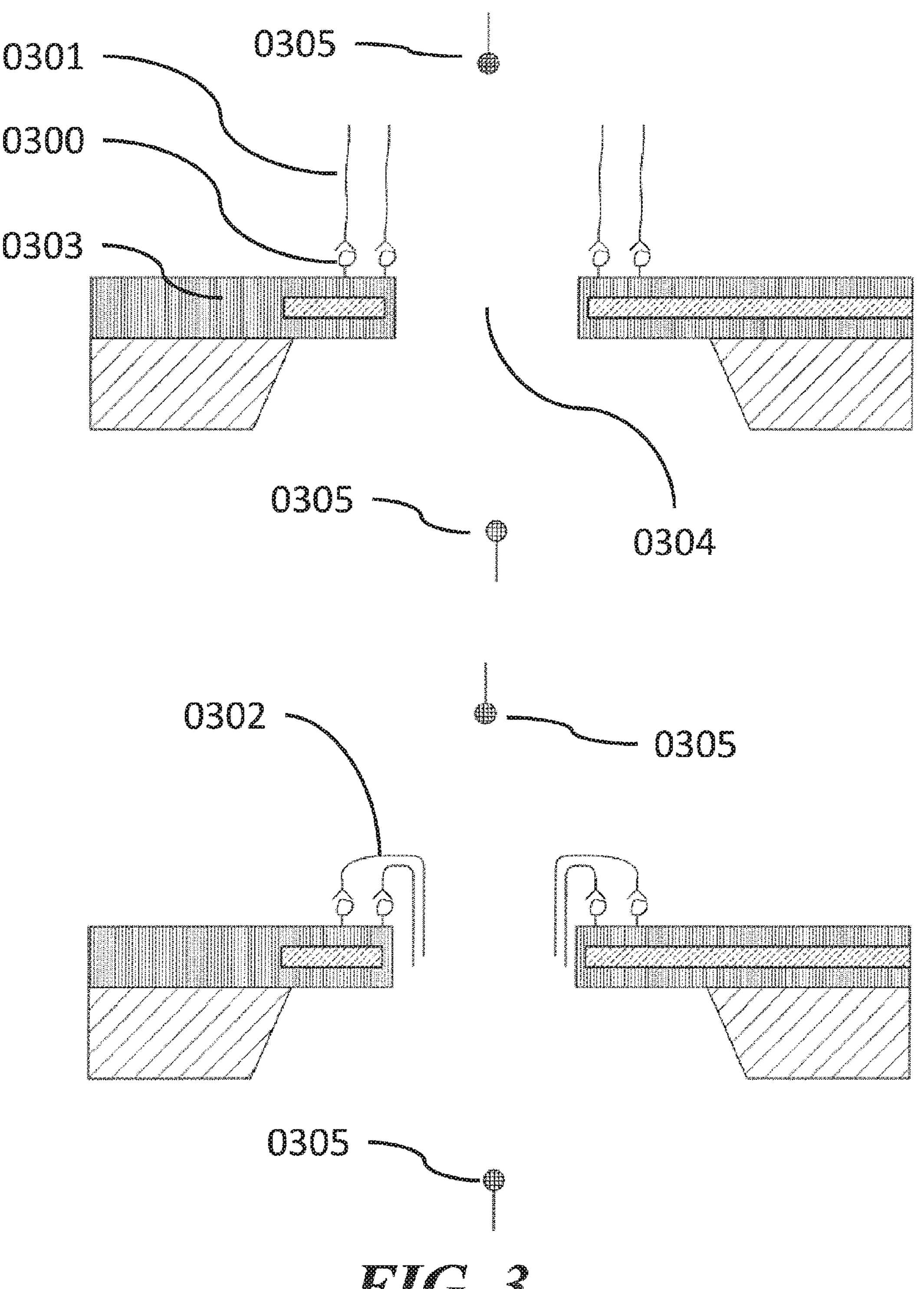
FIG. 3 shows an example of using the sensor of the present disclosure to perform an analyte-antibody or a peptide-antibody binding measurement.

In another embodiment, FIG. 3 shows a chip architecture for analysis of an analyte-antibody interaction. The analyte molecule 0300 (e.g., a protein) is attached to the membrane 0303 near the pore 0304. An antibody having a conjugated charged tag 0301 can bind to the analyte and be pulled into the pore 0302 for detection when a bias is applied by the bias electrodes 0305.

Figure 4:
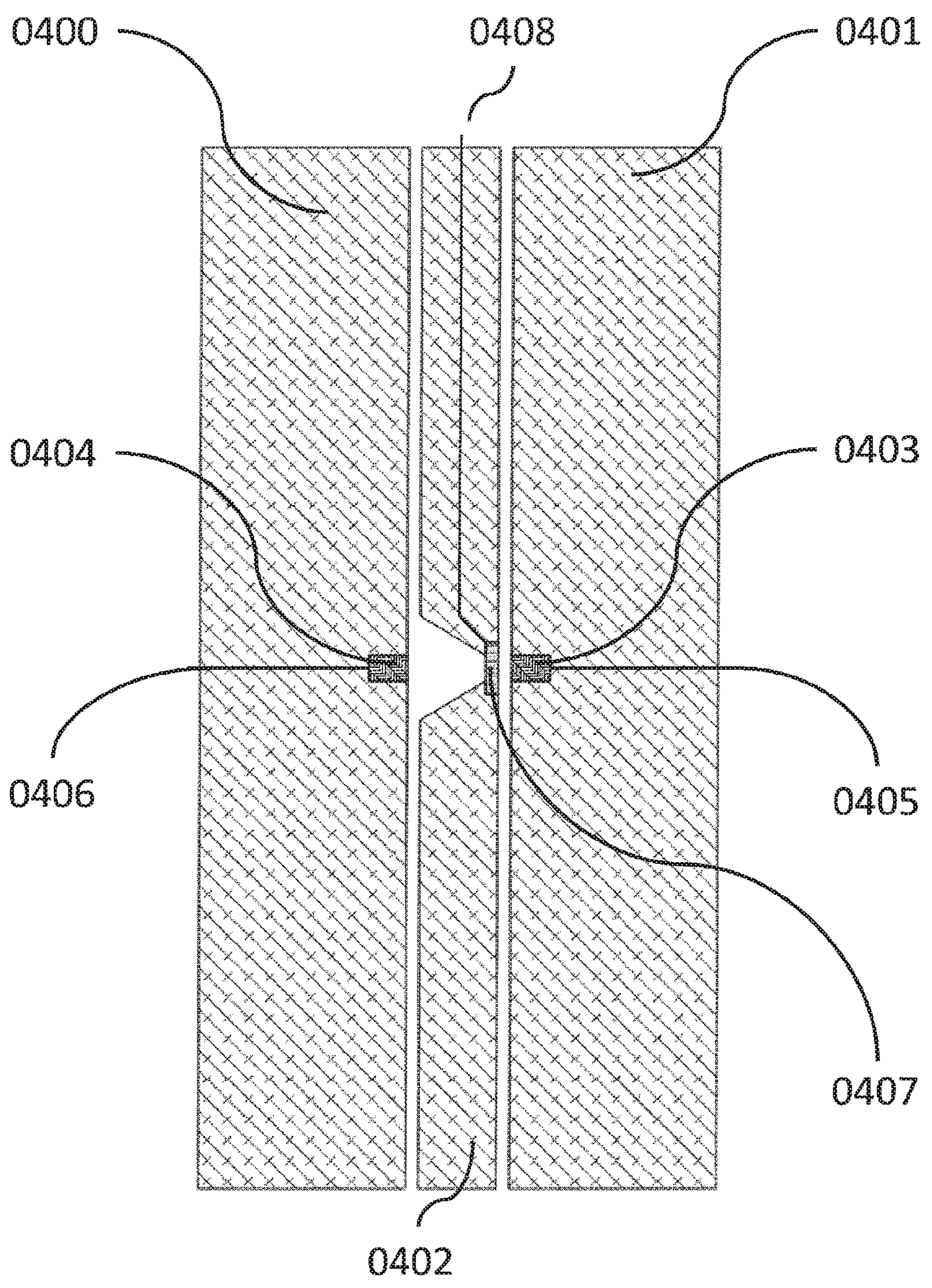
FIG. 4 shows an example of a cross-sectional profile view of a packaged sensor of the present disclosure.

The sensor can be packaged and integrated with electronic and/or fluidic connections (e.g., for operation in a device). FIG. 4 shows an example of a cross-sectional schematic drawing of a packaged chip. The packaged chip has a bottom fluidic cell 0400, a top fluidic cell 0401, and a middle fluidic cell 0402. A top external electrode 0403 and a bottom external electrode 0404 can be attached to external electrode leads (0405 and 0406, respectively). The sensor chip 0407 can be electrically addressed by a sensor chip input/output 0408.

The sensor can be an active sensor (i.e., having an integrated signal amplifier) or a passive sensor (i.e., not having an integrated signal amplifier). In some cases, a passive sensor is integrated with an external signal amplifier (i.e., an amplifier not structurally embedded in the pore sensor itself). In some instances, an active sensor consumes power and requires a power supply. The sensor of the present disclosure can be designed to have any suitably high signal-to-noise ratio (SNR) when operated as a passive or active sensor. In some embodiments, the SNR can be within a range of 1-100 (e.g., is about 1.1, about 1.2, about 1.5, about 2, about 3, about 4, about 5, about 6, about 7, about 8, about 9, about 10, about 15, about 20, about 25, about 30, about 40, about 50, about 100; at least about 1.1, at least about 1.2, at least about 1.5, at least about 2, at least about 3, at least about 4, at least about 5, at least about 6, at least about 7, at least about 8, at least about 9, at least about 10, at least about 15, at least about 20, at least about 25, at least about 30, at least about 40, at least about 50, or at least about 100).

Figure 5A:
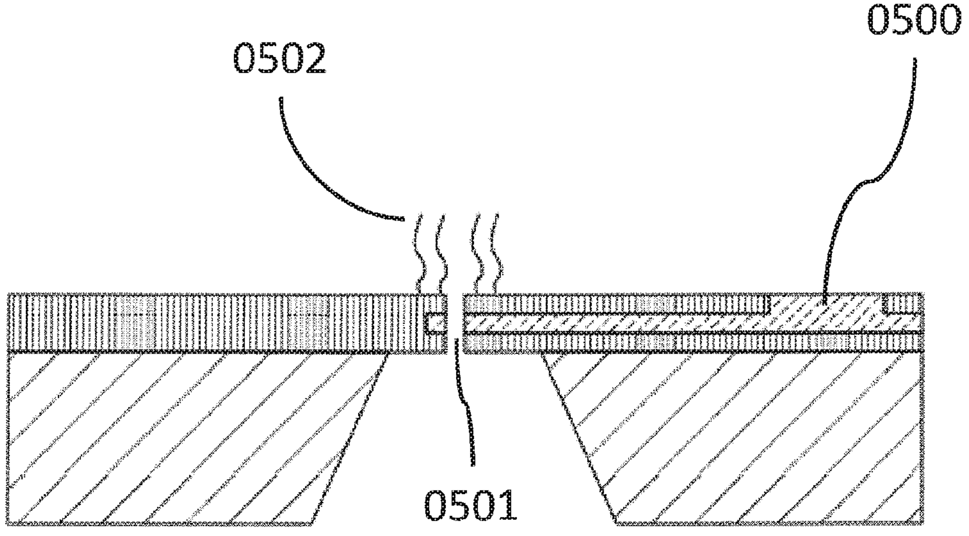
FIG. 5A shows examples of passive sensors of the present disclosure.
Figure 5A:
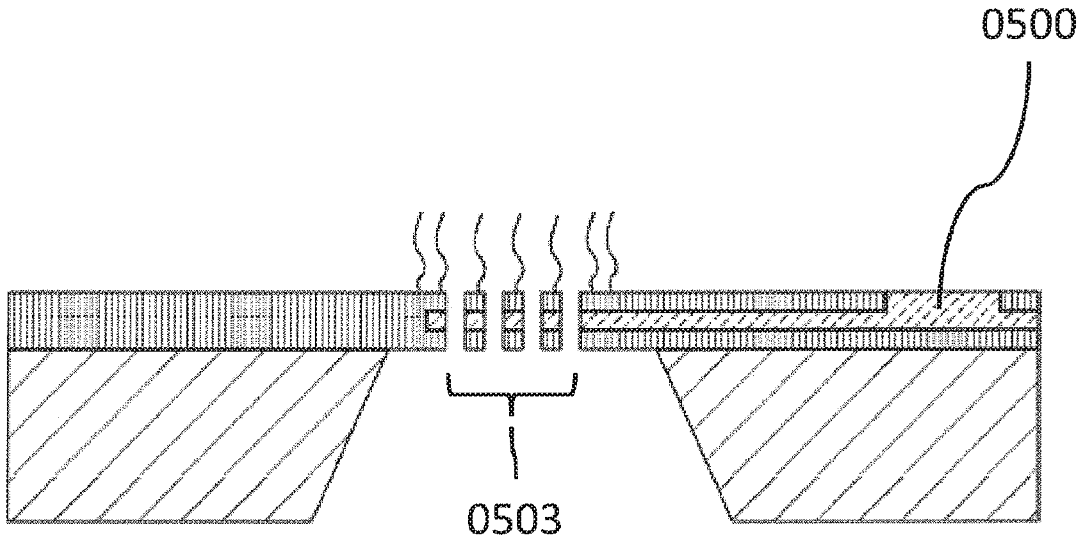
Figure 5B:
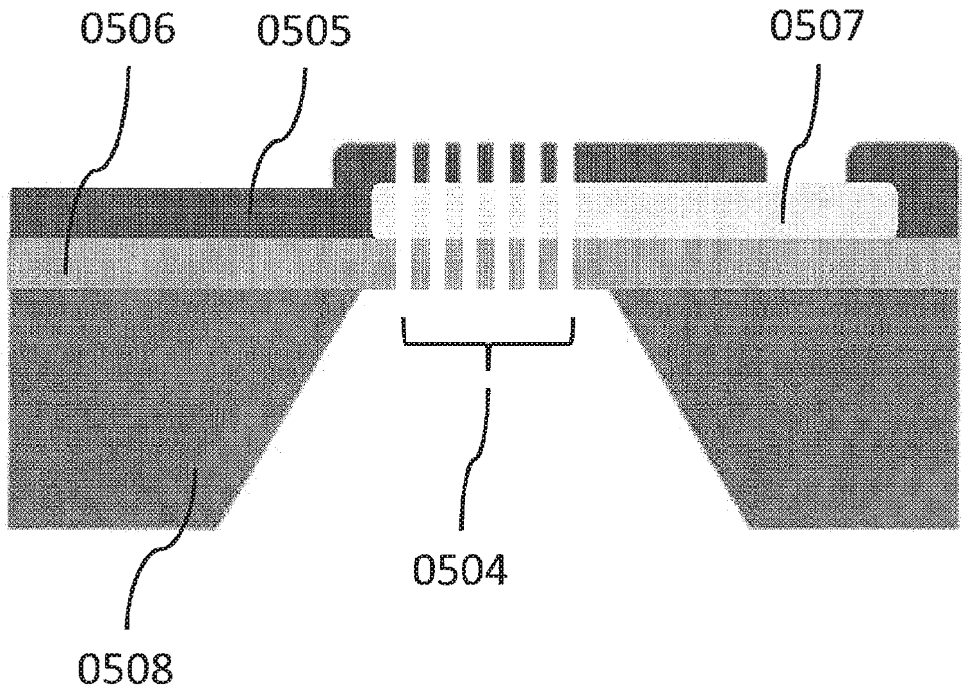
FIG. 5B shows an additional example of a sensor of the present disclosure having a plurality of pores.

FIG. 5A shows one strategy for enhancing the SNR of the sensor. The sensor can have a passive embedded sensing electrode 0500, a pore 0501, and charged analytes immobilized in proximity to the pore 0502. In some cases, there are a plurality of charged analytes that are clonal, but this is not required. A group of different charged analytes can be sensed with a single pore, however, without the ability to differentiate between the charged analytes, in some implementations. In some cases, there is only one pore in the sensor for each colony of charged analytes. However, the sensor of the present disclosure can have a plurality of pores 0503 per colony of charged analytes. Compared to a single pore, a plurality of pores can enhance the SNR by increasing the signal and/or decreasing the noise. In some embodiments, there are 2, 3, 4, 5, 6, 7, 8, 9, 10, 12, 15, 20, 25, 30, 50, 100, 500 or 1000 pores per unique charged analyte. In some embodiments, there are at least 2, at least 3, at least 4, at least 5, at least 6, at least 7, at least 8, at least 9, at least 10, at least 12, at least 15, at least 20, at least 25, at least 30, at least 50, at least 100, at least 500 or at least 1000 pores per unique charged analyte. In some cases, the sensor employs a plurality of pore/analyte repeats that are not necessarily arranged in proximity to each other on the sensor. However, the plurality of pores can also be arranged in proximity to a colony of the unique charged analyte and/or share a common sensing electrode 0500. Having a plurality of pores be addressed by a common sensing electrode can simplify the design of the sensor and/or facilitate miniaturization of the sensor array. FIG. 5B shows an embodiment of the sensor of the present disclosure having a plurality of pores 0504. The sensor has a top insulator including silicon dioxide ($SiO_2$) 0505, a bottom insulator including silicon nitride ($Si_3N_4$) 0506 and a platinum (Pt) electrode 0507 disposed on a silicon (Si) substrate 0508. In some embodiments, the electrode has a thickness of about 75 nanometers (nm) (e.g., 70 nm Pt and 5 nm titanium (Ti)), the membrane has a thickness of 80 nm silicon nitride ($Si_3N_4$) and 70 nm $SiO_2$. The plurality of pores can be defined by photolithography. The plurality of pores can be used to enhance the net charge delivered to the sensor (e.g., in absence of a dedicated integrated amplifier).

Figure 6:
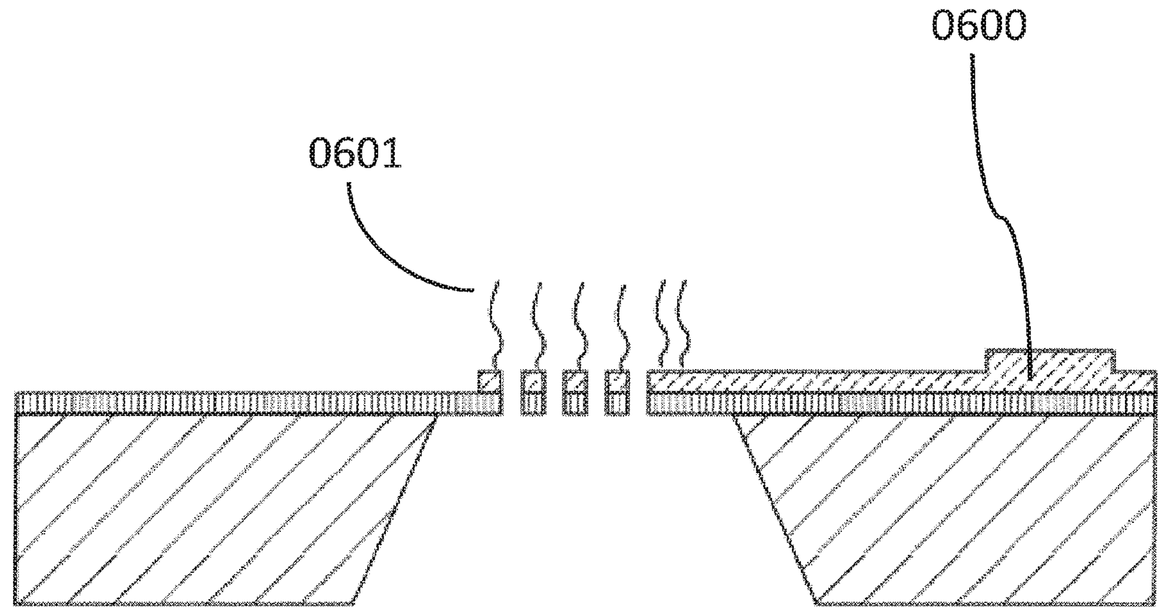
FIG. 6 shows an example of a sensor of the present disclosure having an exposed sensing electrode.

In some embodiments, the sensor has an exposed electrode. As shown in FIG. 6, the exposed electrode 0600 can function as both the sensing electrode and as a substrate onto which the charged analyte 0601 can be immobilized.

Figure 7A:
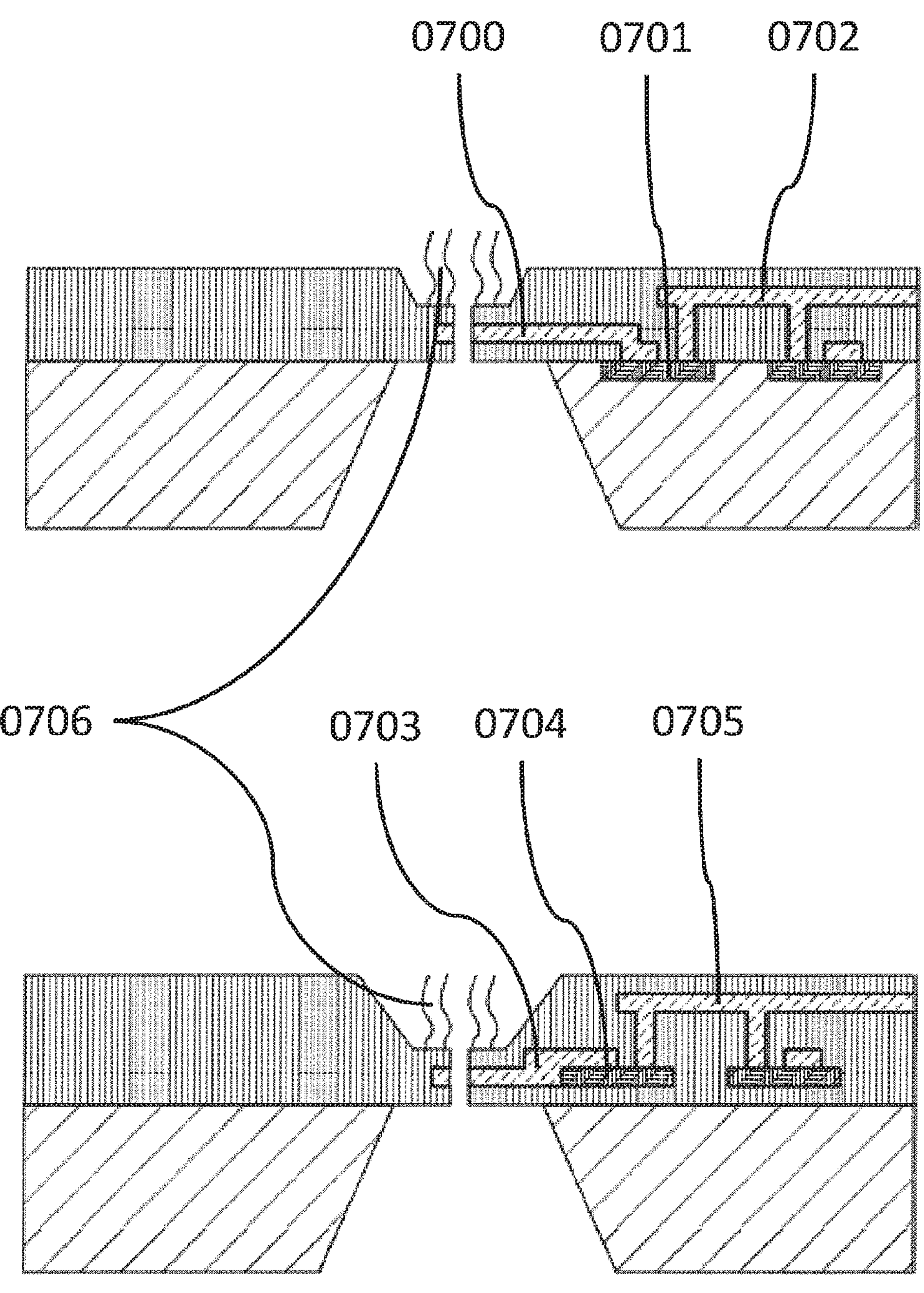
FIG. 7A shows examples of active sensors of the present disclosure.

FIG. 7A shows a profile drawing of two active sensors. The design includes an embedded sensing electrode 0700 for the active sensor, active transistors 0701 including the dedicated amplifier, and interconnects 0702 for the active device. In another embodiment, the embedded sensing electrode 0703 can interface with a thin film transistor (IFT) active amplifier 0704 and have interconnects 0705 for the active device. Both embodiments shown here are capable of detecting the charged analyte 0706.

Figure 7B:
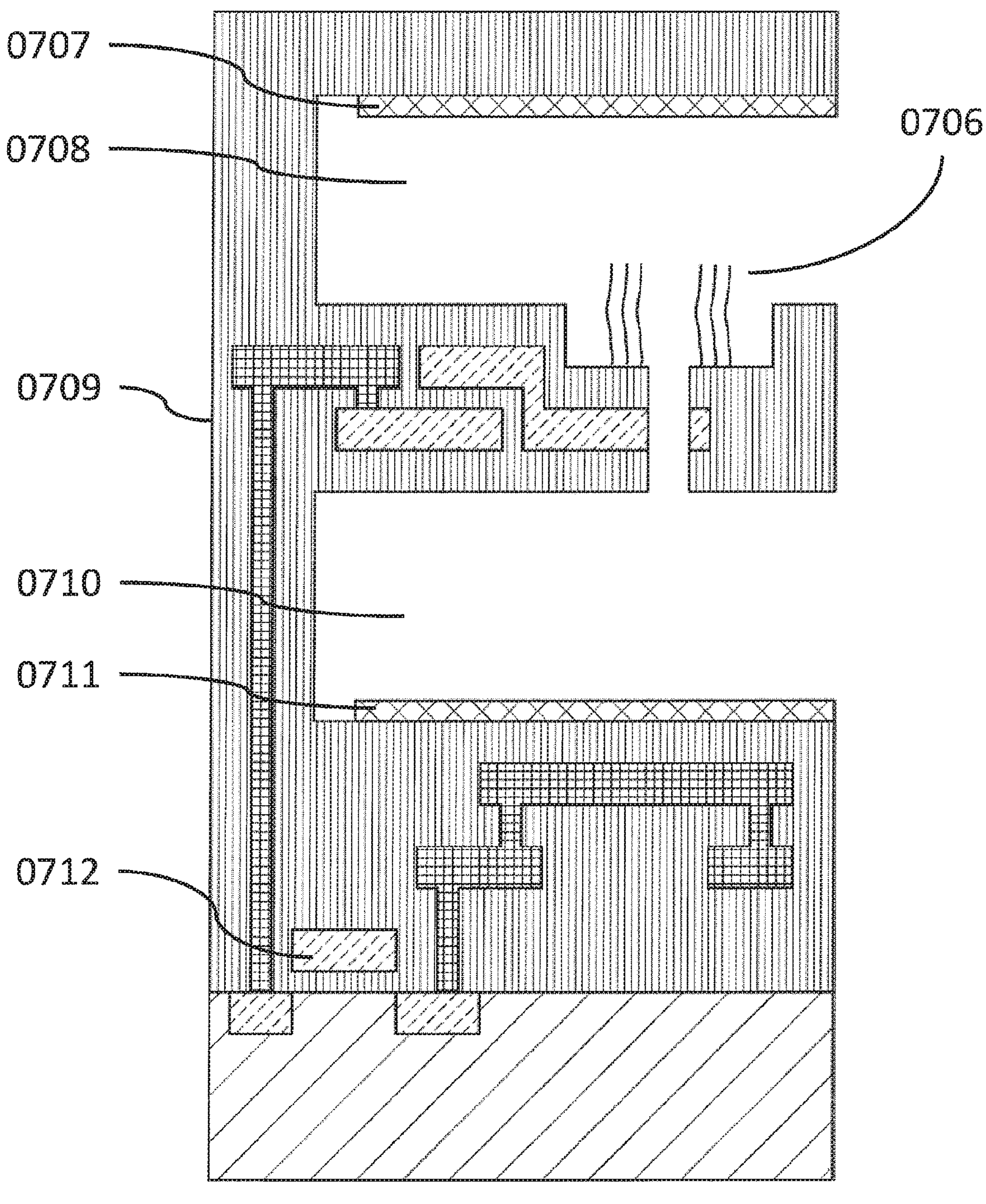
FIGS. 7B-E show various examples of active sensors of the present disclosure.

FIG. 7B shows additional details of an active sensor of the present disclosure having enclosed top and bottom fluidic channels and their respective electrode integrated into the device. The sense electrode is sandwiched in the membrane with an integrated amplifier in close proximity. Such an architecture can reduce the noise arising from the sense electrode. The rest of the input/output (I/O) circuit can be located on a silicon wafer. The sensor can have an integrated top electrode 0707, a top fluidic cavity 0708, an integrated sensing amplifier 0709 as described in FIG. 7A, a bottom fluidic cavity 0710, a bottom electrode 0711 and peripheral circuitry 0712 on the substrate. In some cases, the substrate is silicon. As used generally herein, any reference to "top" or "bottom" are illustrative only, as the sensor can be oriented in any way with respect to gravity.

Figure 7C:
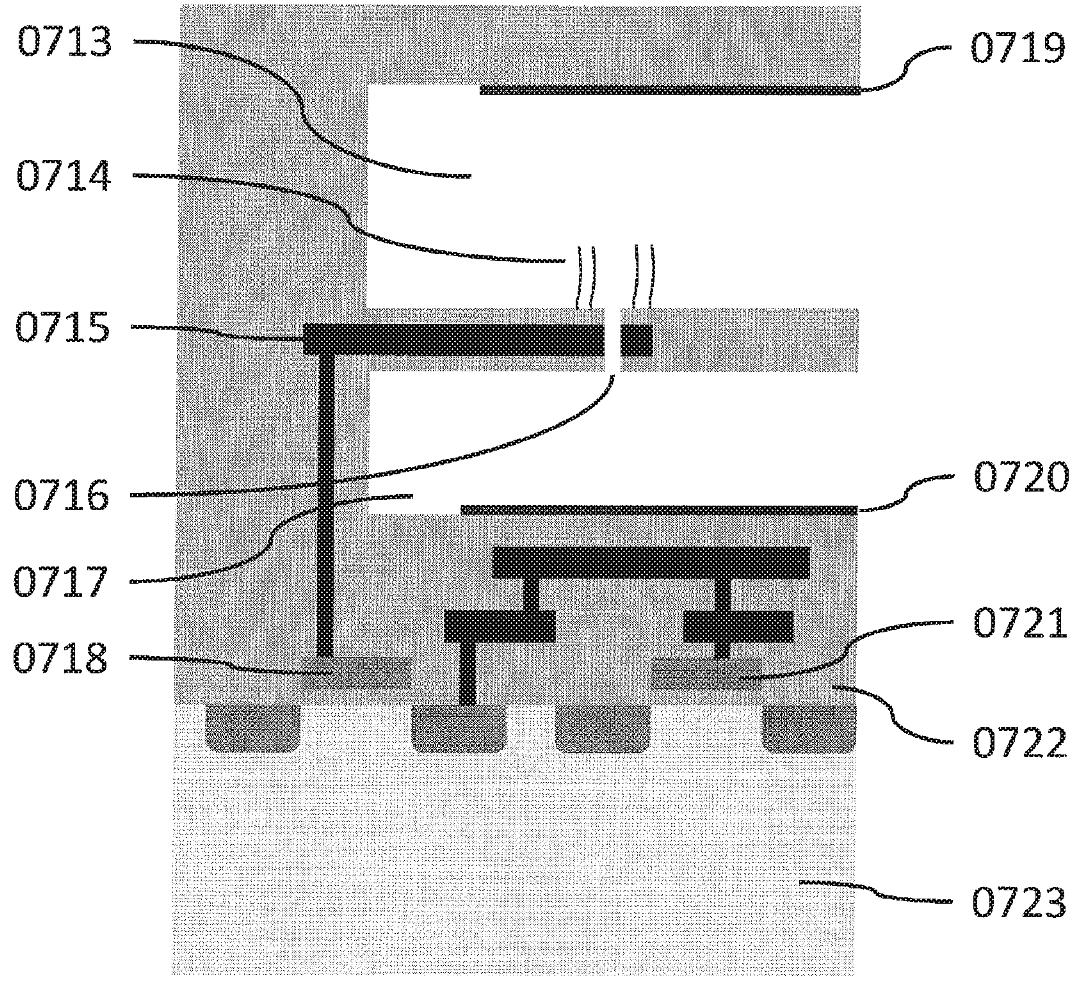
Figure 7D:
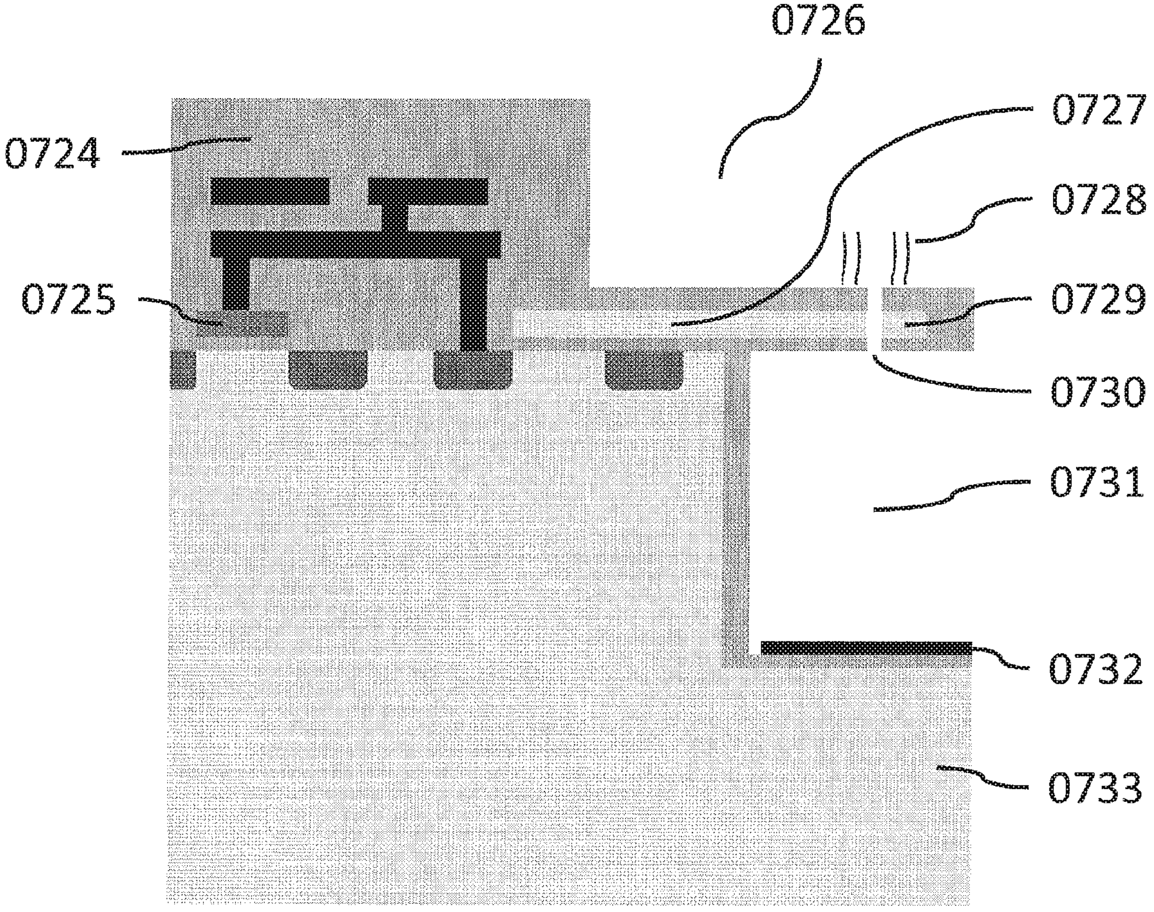
Figure 7E:
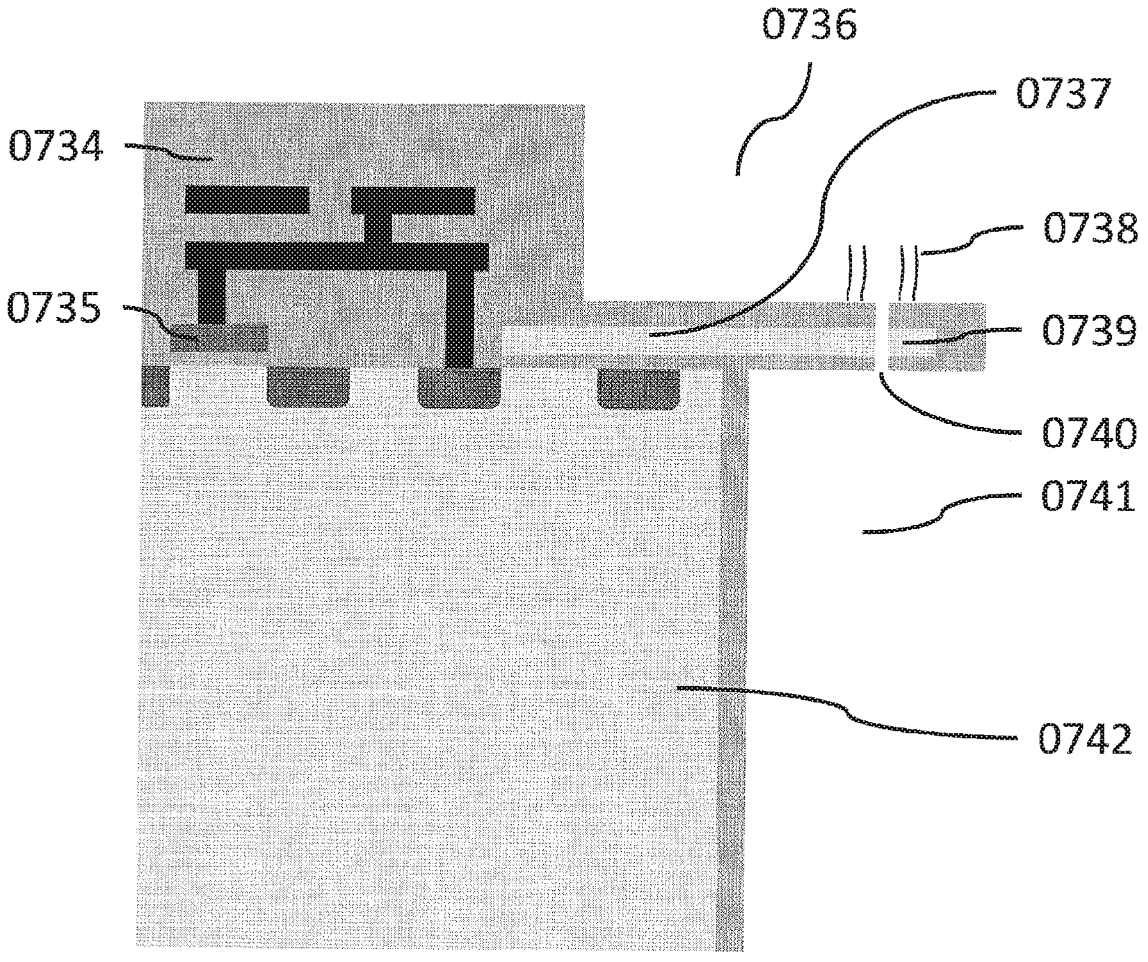

FIGS. 7C-7E show additional embodiments of an active sensor of the present disclosure. FIG. 7C has the amplifier away from the sense electrode in the silicon substrate, which can reduce the noise arising from the amplifier. This embodiment includes a top fluidic channel 0713, an analyte 0714, a sense electrode 0715, a pore sense area 0716, a bottom fluidic channel 0717, a cell amplifier 0718, a top fluidic electrode 0719, a bottom fluidic electrode 0720, an I/O circuit 0721, an insulator 0722 and silicon 0723.

FIG. 7D has an open top fluidic channel and an enclosed bottom fluidic channel, which can negate the need to perform a complex bonding process. All of the active components are on the main silicon substrate, which can allow for robust operation but can require a larger chip area to implement. This embodiment can include an insulator 0724, an I/O circuit 0725, a top fluidic channel 0726, a cell amplifier 0727, an analyte 0728, a sense electrode 0729, a pore sensing area 0730, a bottom fluidic channel 0731, a bottom fluidic electrode 0732 and a silicon substrate 0733.

FIG. 7E shows open top and bottom fluidic channels, which can enable the use of external channel electrodes. All of the active components are on the main silicon substrate, which can allow for robust operation but can require a larger chip area to implement. This embodiment can include an insulator 0734, an I/O circuit 0735, a top fluidic channel 0736, a cell amplifier 0737, an analyte 0738, a sense electrode 0739, a pore sensing area 0740, a bottom fluidic channel 0741 and a silicon substrate 0742.

Figure 8:
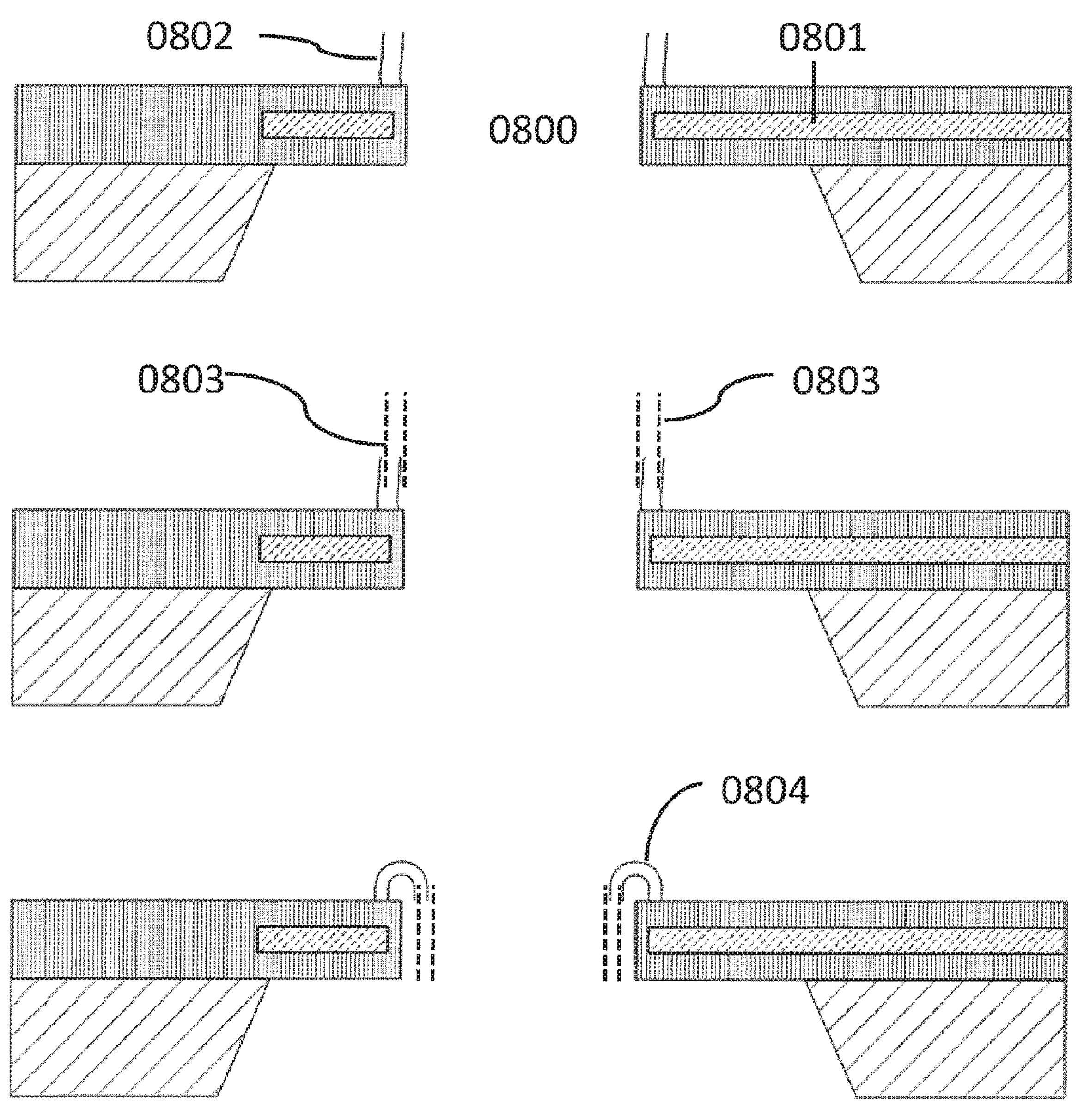
FIG. 8 shows an example of using the sensor of the present disclosure to perform a hybridization measurement.

The sensor can be used to perform a number of analyses or measurements generally known in the art. In some cases, the sensor of the present disclosure enables improved methods or performance thereof compared with the current state of the art. For example, described herein is a hybridization assay (i.e., microarray) that can be used to detect single nucleotide polymorphisms (SNPs). As shown in FIG. 8, the sensor has a charge sensing pore 0800 with an integrated charge sensing electrode 0801 in proximity to immobilized hybridization probes 0802. In some cases, the hybridization probes are nucleic acid molecules that hybridize with an analyte 0803. The analyte can be a second nucleic acid molecule having a sequence that is complimentary to the hybridization probe. Application of a bias across the pore can pull the hybridization probes and analytes (probe-analyte conjugate) into the pore for detection 0804 according to the methods described herein. In some cases, a device of the present disclosure includes an array of sensors, each having a pore with a unique hybridization probe attached in proximity to the pore. Each pore-sensor pair can therefore detect a different analyte. However, in some cases, the hybridization probes immobilized near any given pore are not necessarily the same (i.e., clonal). A given pore can have 2, 3, 4, 5, 6, 7, 8, 9, 10, or more different types of hybridization probes associated with it. In some cases, each of the different hybridization probes has a different analyte that binds to it, with each analyte having a different charge. In this way, a given pore can detect and/or distinguish between 2, 3, 4, 5, 6, 7, 8, 9, 10, or more different analytes.

Figure 9A:
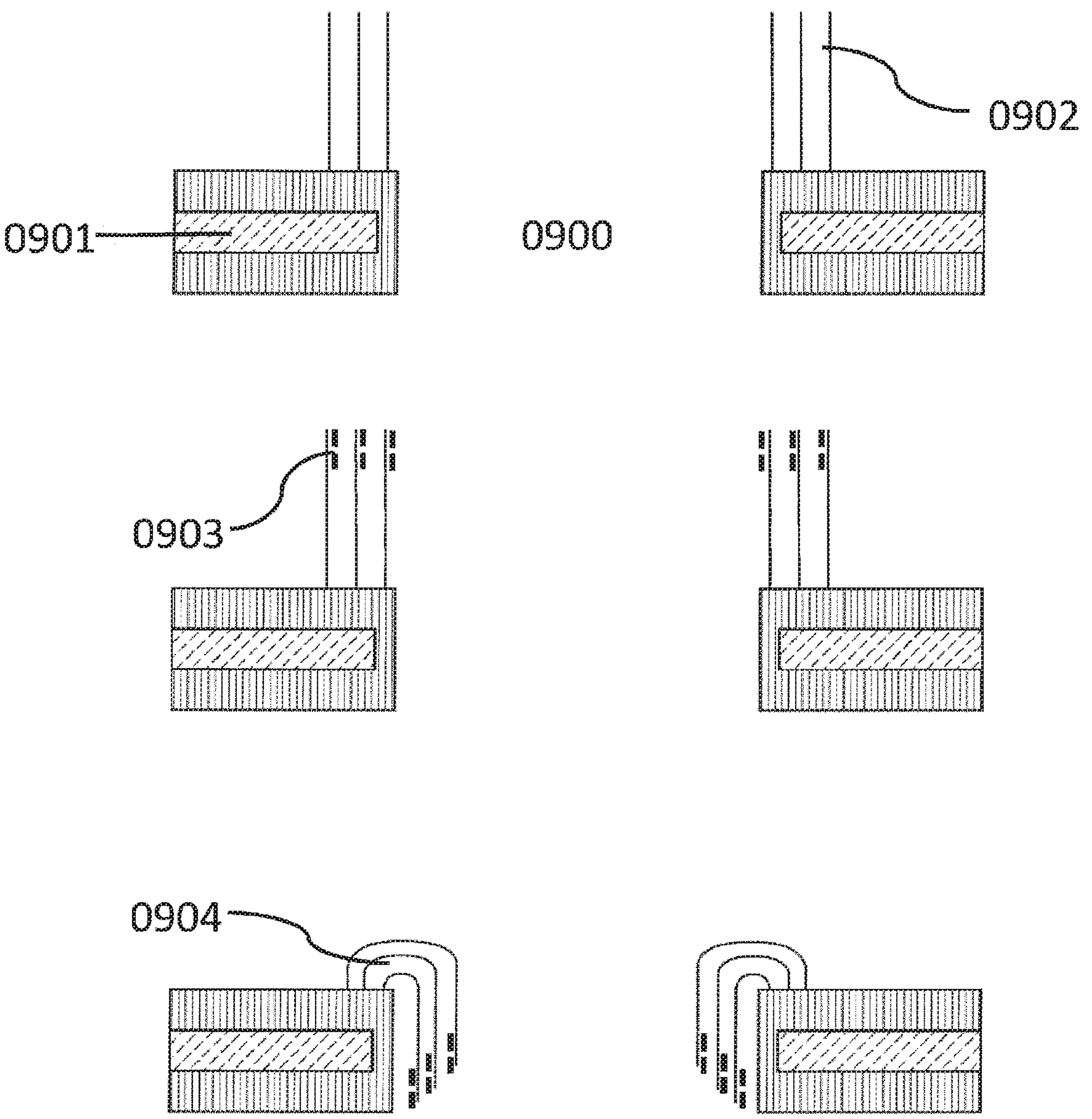
FIG. 9A shows an example of initial steps in performing a sequencing-by-synthesis (SBS) method using a sensor of the present disclosure.
Figure 9B:
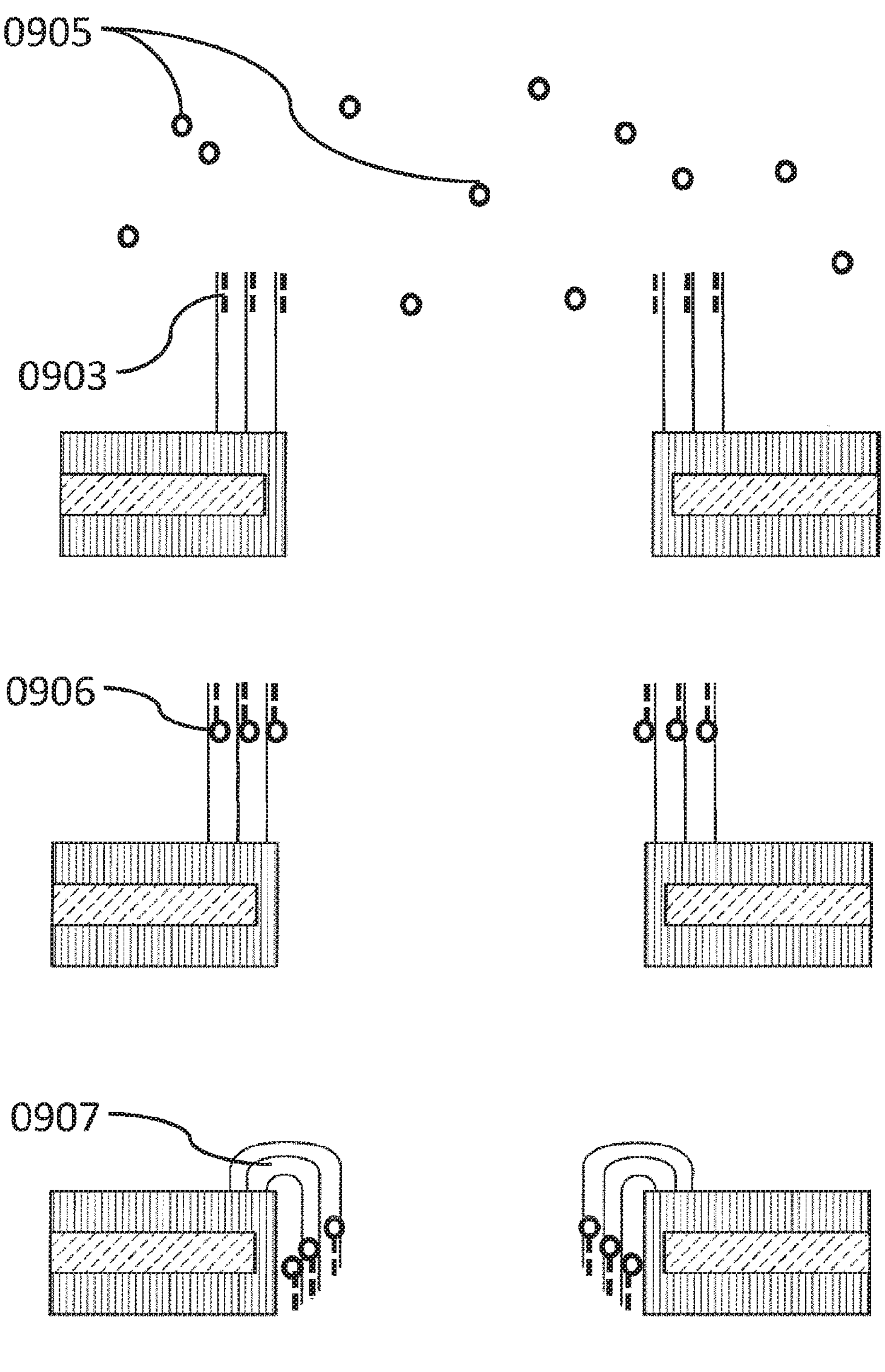
FIG. 9B shows an example of subsequent steps in performing an SBS method using a sensor of the present disclosure.
Figure 10:
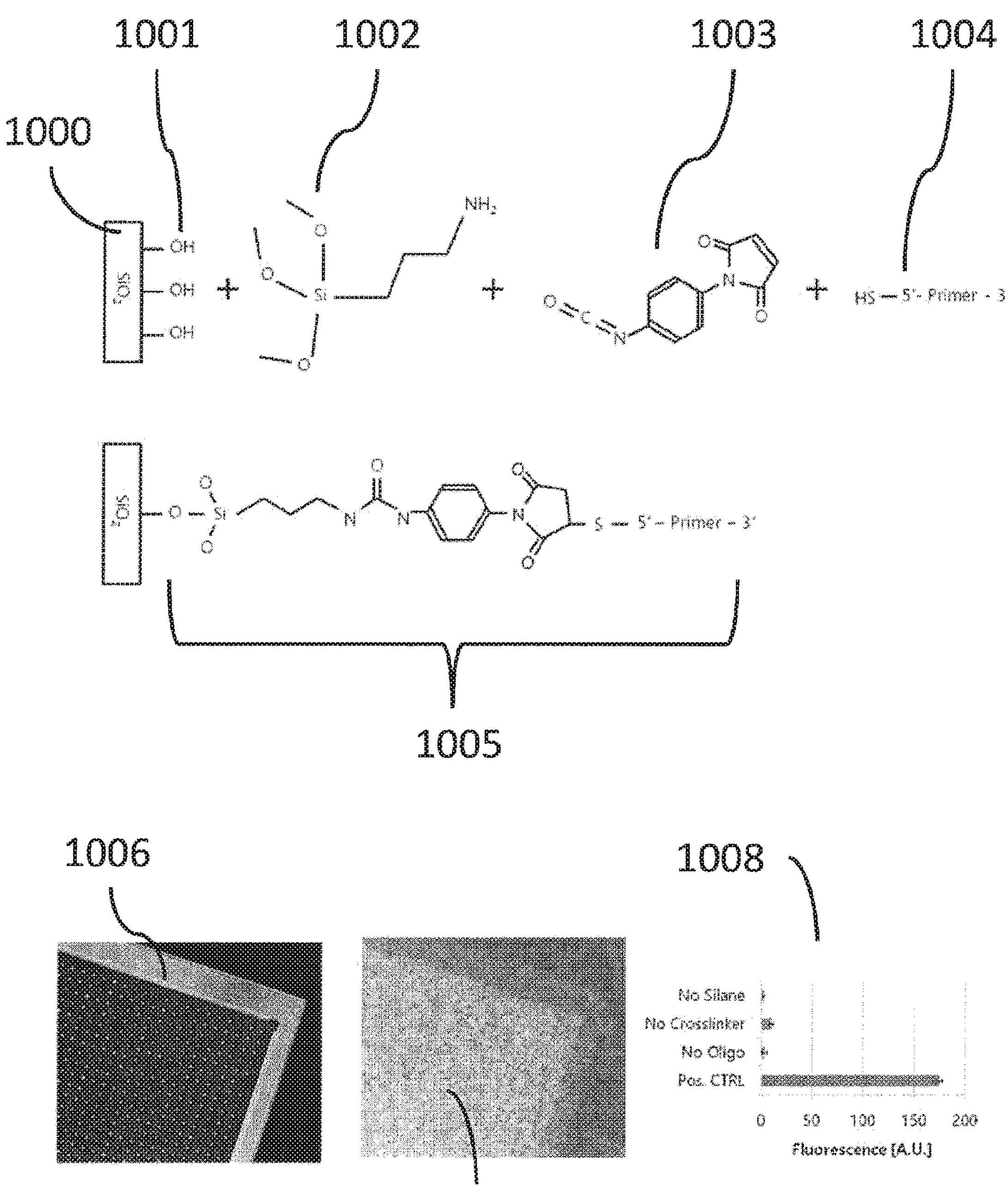
FIG. 10 shows an example of attachment of nucleic acid molecules to the surface of a sensor of the present disclosure.

The sensors described herein can be used to determine the sequence of an analyte (e.g., a nucleic acid molecule). FIG. 9A and FIG. 9B depict the operations that can be used to perform sequencing by synthesis (SBS), with the operations of FIG. 9B following those of FIG. 9A in an iterative fashion. As shown, the method uses a charge sensing pore 0900 and a charge sensing electrode 0901. A nucleic acid to be sequenced 0902 is immobilized in proximity to the pore, for example to adaptors coated on the perimeter of the pore suitable for solid-phase amplification, as shown in FIG. 10. The nucleic acid can be one of a library of nucleic acids, each attached to a separate adaptor in proximity to a separate sensor. The nucleic acid molecule can be amplified using solid-phase polymerase chain reaction (PCR) to form a colony of clonal nucleic acid molecules, also attached to the sensor in proximity to the pore, for example, as described in the International Patent Application Number PCT/AU1992/000587, which disclosure is incorporated herein by reference specifically for this related disclosure. An oligonucleotide primer 0903 can hybridize with the nucleic acids to be sequenced, followed by washing away of non-hybridized primers. Application of an electrical field can draw the nucleic acid-primer complex into the pore 0904 for measurement of a reference charge (i.e., prior to sequencing). The reference charge can be stored. This high electrical field can both pull the immobilized nucleic acid into the sensor and help de-screen the EDL.

Continuing with FIG. 9B, SBS can be performed by extending the primer 0903 by incorporation of a nucleotide 0905 that is complimentary to the nucleic acid molecule to be sequenced at the subsequent base position 0906 (i.e., guanine (G) with cytosine (C) and adenine (A) with thymine (T) or uracil (U)). Excess or non-incorporated nucleotides can be washed away and/or degraded (e.g., with apyrase). Incorporation of the nucleotide increases the negative charge on the nucleic acid—primer complex by one electron (relative to the reference charge and/or charge measured at the previous iteration), which can be sensed by applying a voltage across the pore suitable for pulling the nucleic acid-primer complexes into the pore 0907. The sensed charge can be compared with the reference and/or previous charge (which is optionally stored in the sensor) to make a base call. The SBS procedure described herein can continue by iteratively challenging the system with each of the four bases A, G, C, T (or U in the case of RNA) in succession, in any order. Instances in which the system was challenged with a base that is not complimentary to the subsequent base position will not result in a change in charge. In some cases, the change in charge is attributable to the increased length of the phosphate backbone of the growing primer strand, with one negative charge per base position. Those skilled in the art will appreciate that the incorporation of a nucleotide can be performed with a polymerase enzyme in the presence of a suitable buffer, including magnesium and/or manganese ions.

Figure 9C:
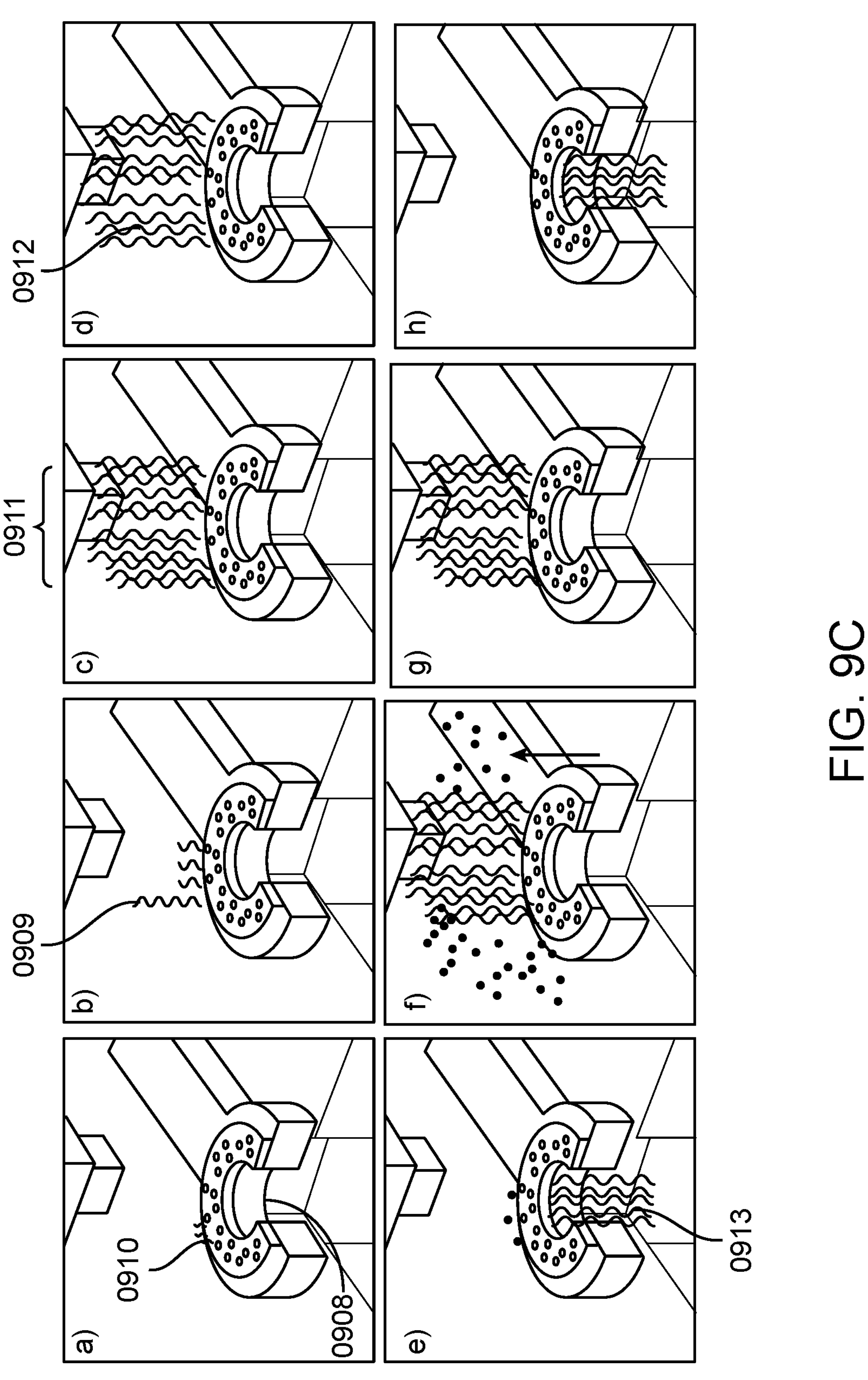
FIG. 9C shows an additional example of a method for performing an SBS reaction using a sensor of the present disclosure.

FIG. 9C shows another depiction of a method for SBS using the sensor of the present disclosure and is similar to the steps described with reference to FIG. 9A and FIG. 9B. As shown, the method uses a charge sensing pore 0908. A nucleic acid to be sequenced 0909 is immobilized in proximity to the pore, for example to adaptors coated 0910 on the perimeter of the pore suitable for solid-phase amplification. The nucleic acid can be one of a library of nucleic acids, each attached to a separate adaptor in proximity to a separate sensor. The nucleic acid molecule can be amplified using solid-phase polymerase chain reaction (PCR) to form a colony of clonal nucleic acid molecules 0911. An oligonucleotide primer 0912 can hybridize with the nucleic acids to be sequenced, followed by washing away of non-hybridized primers. Application of an electrical field can draw the nucleic acid-primer complex into the pore 0913 for measurement of a reference charge (i.e., prior to sequencing). SBS can be performed by extending the primer by incorporation of a nucleotide 0914 that is complimentary to the nucleic acid molecule to be sequenced at the subsequent base position. Excess or non-incorporated nucleotides can be washed away and/or degraded (e.g., with apyrase). Incorporation of the nucleotide increases the negative charge on the nucleic acid-primer complex by one electron (relative to the reference charge and/or charge measured at the previous iteration), which can be sensed by applying a voltage across the pore suitable for pulling the nucleic acid-primer complexes into the pore 0915.

Densely populated immobilized DNA can be provided to a sensor and solid-phase PCR amplification or bridge amplification can be performed. A gas phase silanization of the chip surface can be performed with molecular vapor deposition of (3-aminopropyl)-trimethoxysilane (APTMS). Using the crosslinker N-(p-maleimidophenyl)isocyanate (PMPI), a thiol-modified oligonucleotide that acts as the PCR primer can be attached to the chip surface. There are a variety of other crosslinkers that can be used.

FIG. 10 shows an example of a process of covalently attaching nucleic acids to the charge sensor surface, consistent with various aspects of the present disclosure. A $SiO_2$ surface 1000 including hydroxide moieties 1001 (and/or that is hydroxylated) can be silanized (e.g., using aminosilane 1002). Silanization can be performed in gas phase. A crosslinker (e.g., PMPI 1003) can be used to connect the amine group on the silane and the sulfhydryl group of the 5' thiol-modified primer 1004. The resulting product of the surface chemistry described herein is shown at 1005.

In practice, sensing chips were plasma cleaned, rehydrated and functionalized with (3-aminopropyl)-trimethoxysilane (APTMS) using a chemical vapor deposition system. The amino-functionalized surfaces were subsequently transformed into a thiol-reactive moiety by exposure to a 2.3 mM solution of N-(p-maleimidophenyl) isocyanate (PMPI) in anhydrous toluene at 40° C. for 2 hours under an argon atmosphere. The surfaces were subsequently washed with anhydrous toluene and dried in a stream of argon followed by DNA immobilization using thiolated oligonucleotides. Prior to immobilization the thiolated oligos were reduced using tris(2-carboxyethyl)phosphine (TCEP) as a reducing agent and desalted using a spin column (MWCO=3000). Thiolated oligos can be spotted directly onto sensing chips for 6 hours at 10 μM concentration in a 1 M NaCl buffer solution under a controlled atmosphere, followed by extensive washing. The various surface modification steps were followed by x-ray photoelectron spectroscopy and the presence of the expected elements and peak shifts confirmed the transformation of the sensing surface. The bridge PCR amplification itself is done by thermal cycling the sensor chip in a standard PCR tube along with the appropriate reagents and a 900 base pair (bp) template previously prepared. The result of the attachment chemistry is a chain of covalent bonds securely immobilizing 900 bp DNA molecules to the chip surface. The length of the 900 bp template was selected since its length is a close match to the fabricated pore length. The solid-phase amplified DNA molecules are linearized by a restriction enzyme. The dense presence of immobilized nucleic acid from solid-phase amplification is verified by fluorescence microscopy with appropriately excited SYBR Gold nucleic acids dye. FIG. 10 shows microscopy images of the charge sensor chip with and without the immobilized DNA molecules.

In order to verify that the result of fluorescence response is from successful bridge amplification and not from nonspecific binding, several control experiments were carried out. In each experiment, a component in the surface chemistry (aminosilane, crosslinker and thiolated oligo) was omitted prior to thermal cycling that nominally would result in PCR amplification. FIG. 10 shows the result. The absence of any of the components resulted in a low level of fluorescence signifying that the solid-phase PCR amplification is only successful when all of three surface chemistry components are in place as shown in 1008. Slightly elevated fluorescence brightness in the case where aminosilane was deposited and thiolated oligonucleotide primers were incubated without the presence of the crosslinker is speculated to be low levels of nonspecific adhesion of negatively charged oligos to the positively charged amine group of the silanes.

FIG. 10 shows an example of an optical microscopy study of solid-phase PCR amplified DNA on the sensor surface, consistent with various aspects of the present disclosure. A bright field microscopy image 1006 of a sensor with solid-phase PCR amplified DNA of ca. 900 bases (the light gray area is the $SiN_x/SiO_2$ membrane) is shown. The dark porous area is the Pt sense electrode with the pore array. The 1 μm pores are defined by photolithography. Also shown is a fluorescence microscopy image 1007 of the chip at the location shown in 1006. SYBR Gold-stained DNA fluorescence signifies an abundance of DNA molecules and successful solid-phase PCR amplification. A series of control experiments, where a component in the surface chemistry has been omitted to enhance fluorescent brightness of the chip with various missing surface chemistry is shown at 1008.

With nucleic acids immobilized, a passive or active sensor chip, consistent with various aspects of the present disclosure, can be operated in the following fashion: i) a positive potential can be applied to the cathode, ii) application of the potential can create an electric field near the pore in such a way that the immobilized analyte (e.g., nucleic acid) molecules are drawn into the pore and iii) the analyte molecules' presence in the pore under an external electric field leaves an electrical signal onto the (e.g., platinum) sense electrode whose potential can be recorded for analysis. With the analyte covalently immobilized on the top surface, the sensor's ability to distinguish charge can be tested by observing the signal difference between a negative control experiment where there is no surface chemistry done to the sensor chips, chips with single-stranded (SS) DNA attached with 900 electrons (e−) per molecule, and chips with double-stranded (DS) DNA attached with 1800e− per molecule of charge.

Figure 11:
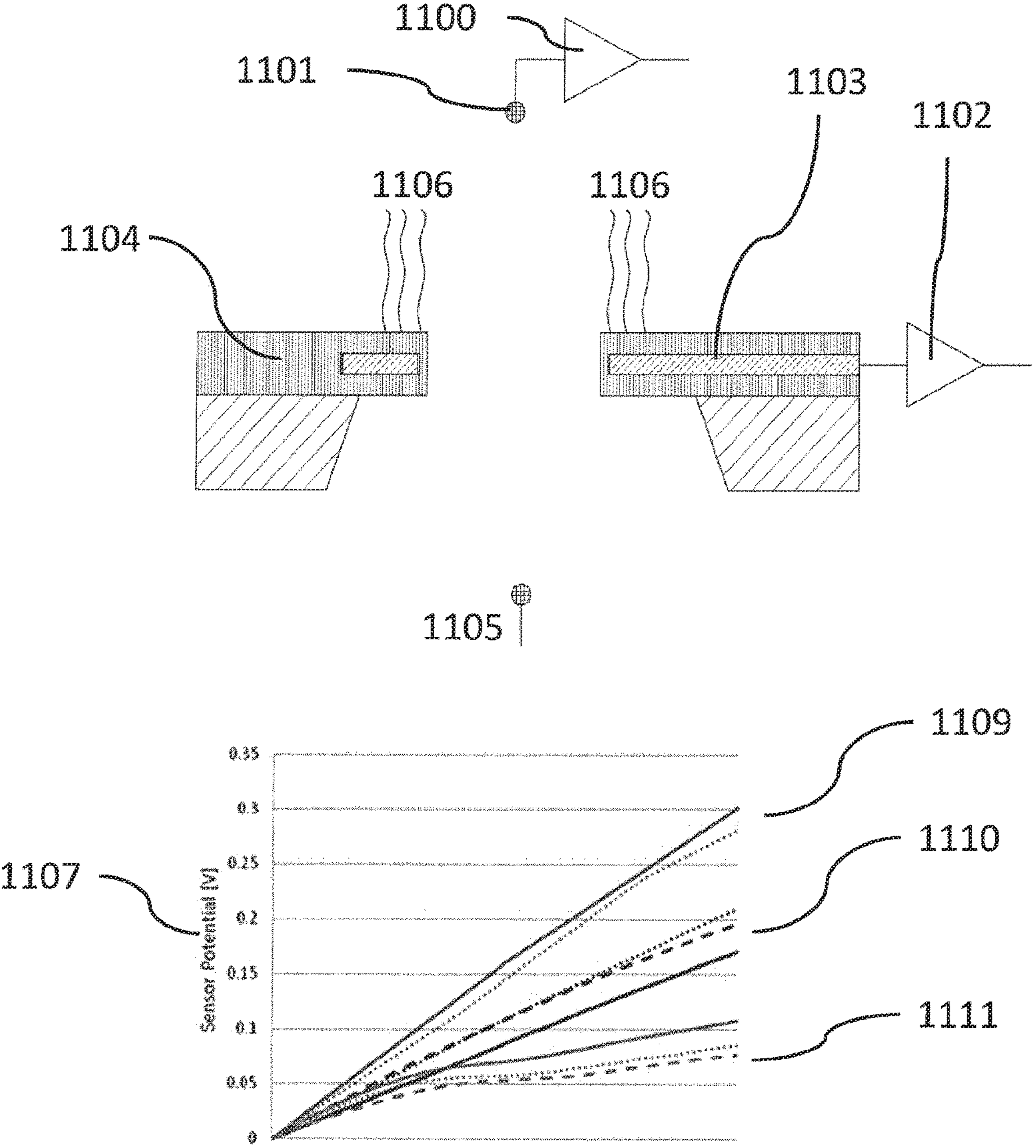
FIG. 11 shows an example of a sensor of the present disclosure and operation thereof.

FIG. 11 shows an example of a demonstration of a charge sensor, consistent with various aspects of the present disclosure. The schematic of the charge sensor setup includes a current amplifier 1100 connected to a top electrode 1101, a unity gain voltage amplifier 1102 off the chip, a sensing electrode 1103 (75 nm platinum electrode), an insulating membrane 1104, a bottom electrode 1105, and immobilized (linearized) nucleic acid molecules 1106 on the $SiO_2$ surface. When positive potential is applied to the cathode, the nucleic acid molecules are pulled into the pore, altering the potential of the sense electrode 1103. The measurements can be done in low concentration salt (e.g., 100 μM KCl) to enhance the electrical detection. As shown in the bottom most part of FIG. 11, the sensor potential (output of 1102), can be measured in units of volts (V) and monitored 1107 while the applied cathode potential is increased and shown in units of milli-volts (mV) 1108. Each curve represents a measurement with a different sensor chip (i.e., solid lines, short dashed lines and long dashed lines). The upper-most group of lines 1109 represents a negative control where there was no nucleic acid attached. The intermediate group of lines 1110 represents those chips that have had 900 bases of SS DNA attached to them. The lower-most group of lines 1111 represents those chips that have had 900 base pairs of DS DNA attached. While some chip-to-chip variation is observed, overall the sensor is able to differentiate the net charge difference between the three cases. With a 100 mV difference observed between ca 900 bases, we see a 110 μV/base.

Figure 12A:
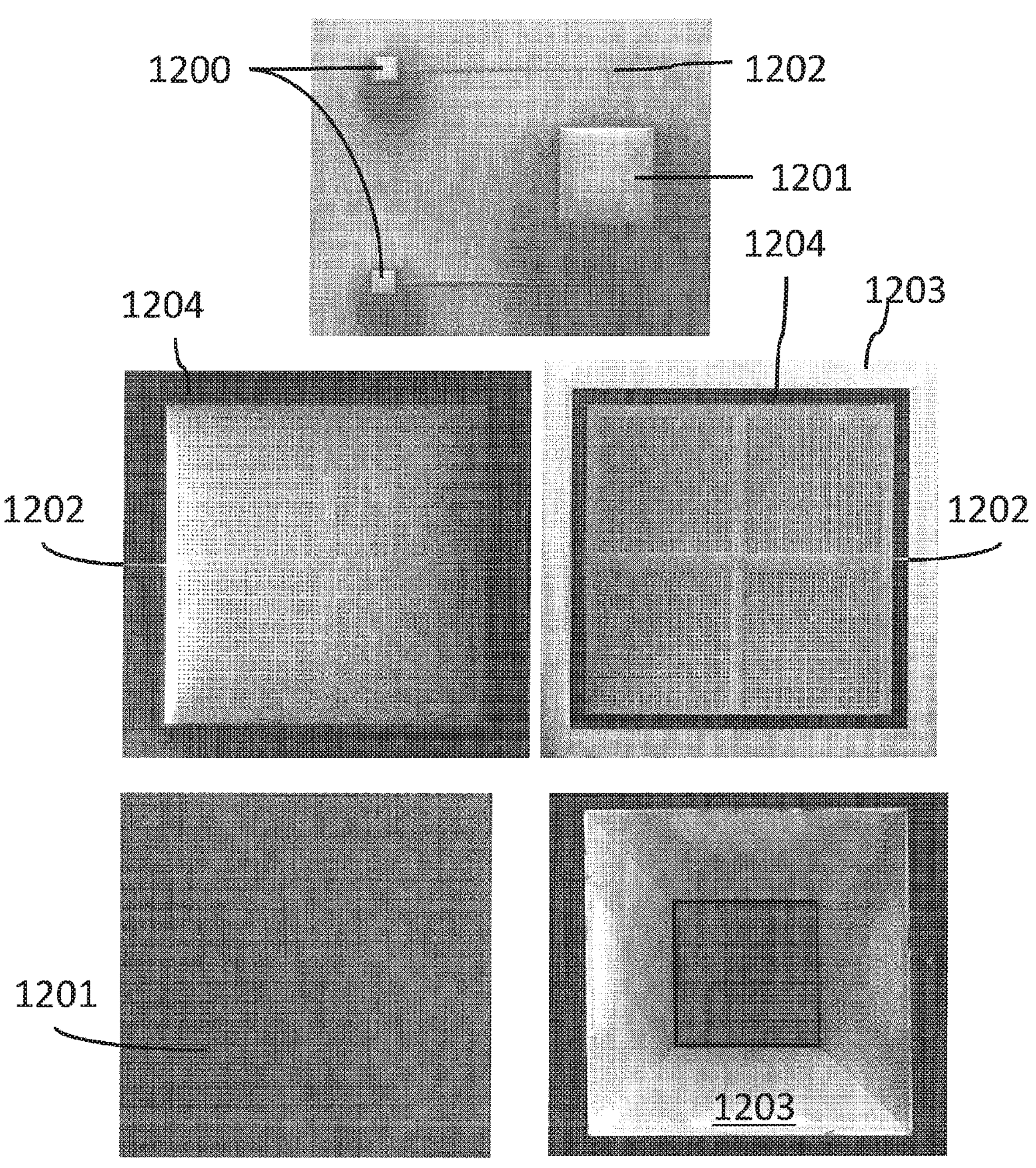
FIG. 12A shows examples of electron microscopy images of a device of the present disclosure.
Figure 12B:
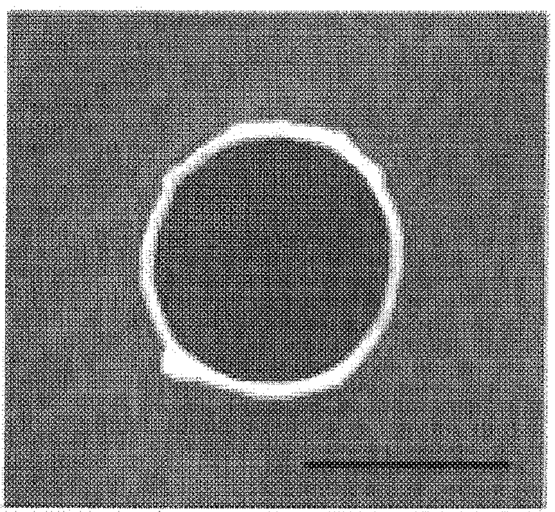
FIG. 12B shows examples of electron microscopy images of a pore of the present disclosure.
Figure 12B:
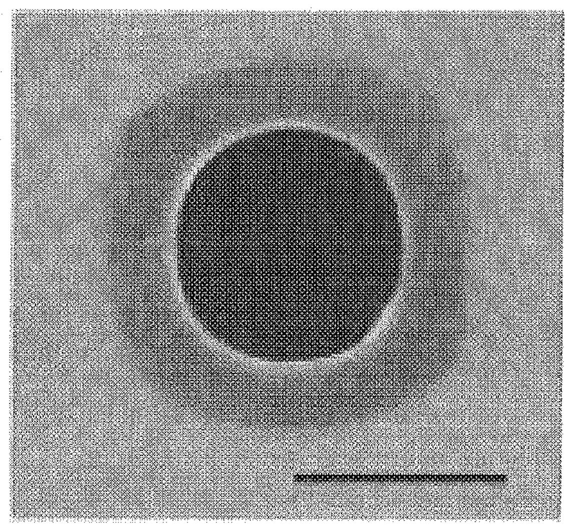

FIG. 12A shows electron microscopy images of the device described in FIG. 11. Bond pads 1200 are shown with 2× redundancy. The microporous sensor pore area 1201 can be attached by a signal wire 1202. The sensor area can be served by a single platinum electrode. The micrographs also show the silicon substrate 1203 and a $SiO_2/SiN_x$ membrane 1204. FIG. 12B shows two examples of electron micrographs of the pore of the sensor of the present disclosure, including a top view 1205 ($SiO_2$ side) and a bottom view 1206 ($Si_3N_4$ side). The scale bars are 1 μm and the measured pore diameters are ca 1.15 μm.

Figure 13:
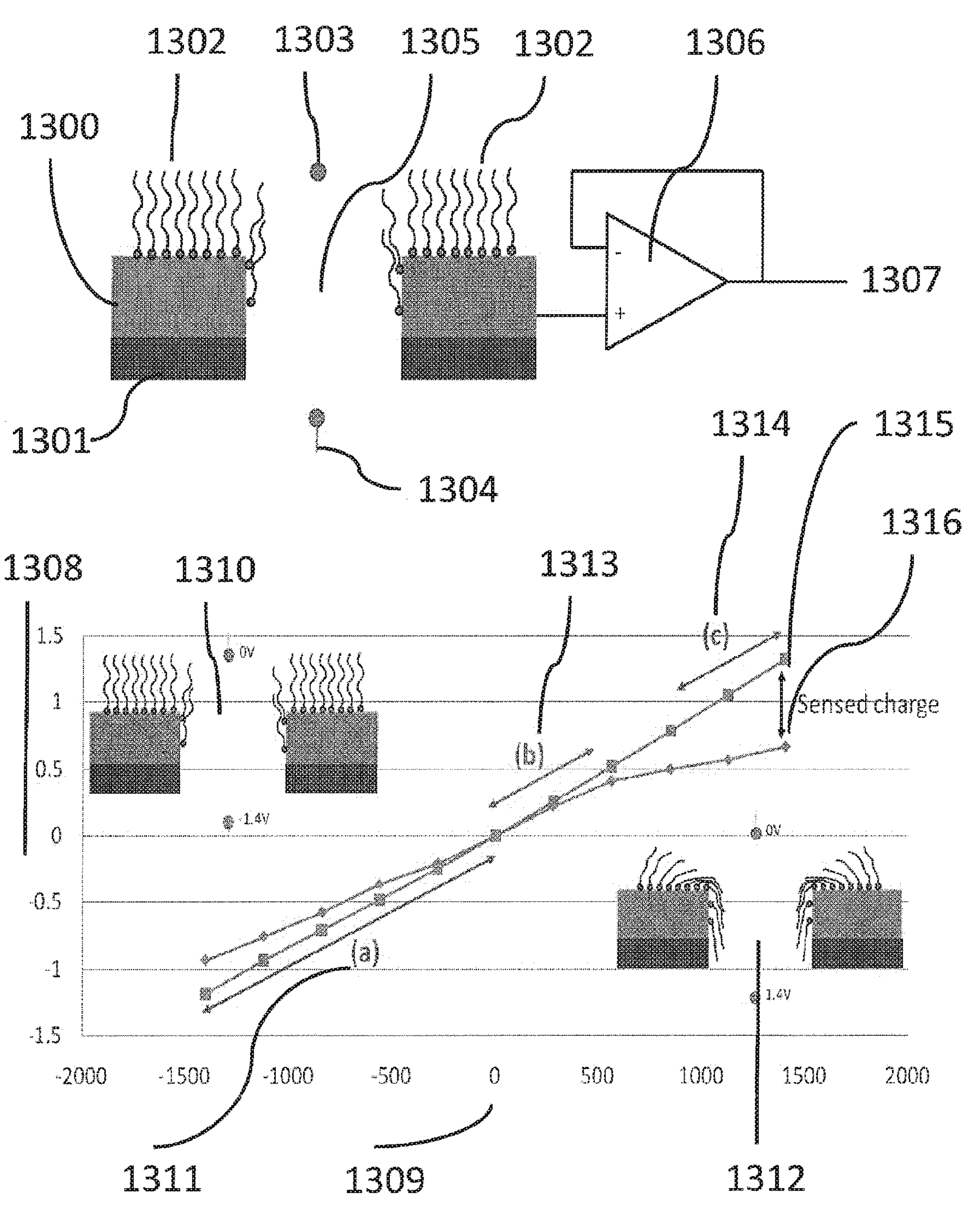
FIG. 13 shows an example of a sensor of the present disclosure and operation thereof.

FIG. 13 shows an example of a charge sensor and result of operation of the charge sensor. The sensor has an exposed gold sense electrode 1300 as described in FIG. 6. The sensor further includes a $SiN_x$ membrane 1301, 450 bp of DS DNA immobilized at one thiolated 5' end 1302, a top electrode 1303, a bottom electrode 1304, a pore (2 μm in diameter) 1305, and a unity gain amplifier 1306 providing a sensor signal output 1307. The sensor potential (at 1307) is plotted on the vertical axis in units of volts (V) 1308 as a function of applied bias 1309 in units of milli-volts (mV)(applied at 1304). Application of a negative bias to the bottom electrode 1304 results in the nucleic acid molecules being pulled out of the pore 1310, and no meaningful difference in sensor potential being measured when nucleic acids are attached to the sensor (smaller diamond markers) versus a control without nucleic acid molecules (larger square markers), as shown in the left-most section of the plot 1311. Application of a positive bias to the bottom electrode 1304 results in the molecules pulled into the pore 1312. No difference is observed at low positive bias, as shown in the middle section of the plot 1313. However, at high positive bias, the sensor potential is significantly reduced relative to the control, as shown in the right-most section of the plot 1314. At high positive bias, the control case where no DNA were attached to the chip 1315 shows the sensor output which mirrors the result of negative bias application, resulting in a symmetrical operation. At high positive bias, the instance where DNA molecules were attached to the chip 1316 results in successful detection of nucleic acids charge.

Figure 14A:
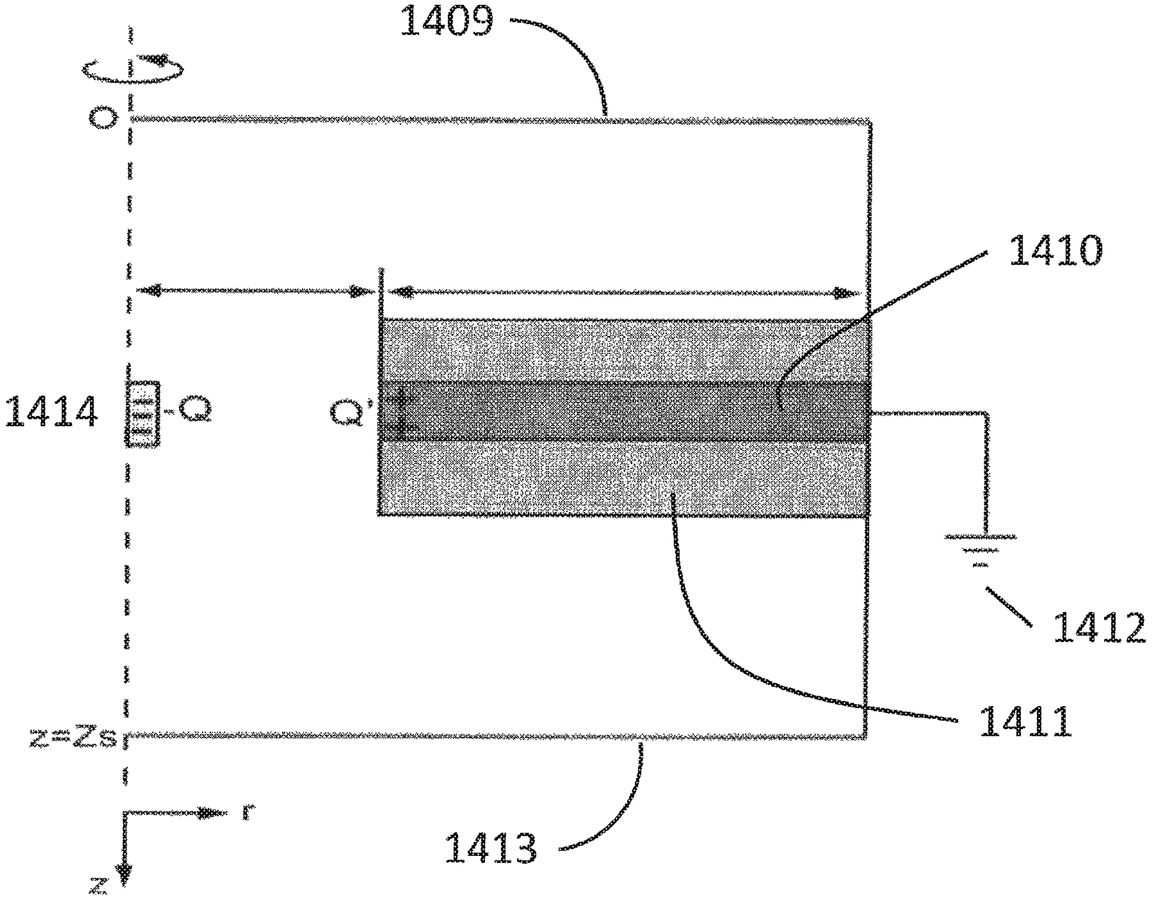
FIG. 14A shows an example of the device of the present disclosure for simulation of operation thereof.

To demonstrate the operating principle, a cylindrically symmetric model system was simulated where a fragment of 60 bp double-stranded (DS) DNA is located at the center (the most challenging detection scenario) of an aqueous nanopore, as schematically shown in FIG. 14A. The system includes a cathode 1409, a metal electrode 1410, a solid dielectric 1411, a virtual ground 1412, an anode 1413, and a charged molecule 1414. The Poisson-Nernst-Planck (PNP) equations along with the Stokes equations were solved to model the ionic and fluidic transport across the pores using the general partial differential equation solver Prophet, to solve the nonlinear, coupled model equations. The PNP equations are $$\nabla\cdot(\varepsilon_w\nabla\psi)+q(C_+-C_-)=0;$$

$$q\nabla\cdot(-D_+\nabla C_+-\mu_+C_+\nabla\psi+C_+\vec{u})=0;$$

$$-q\nabla\cdot(-D_-\nabla C_-+\mu_-C_-\nabla\psi+C_-\vec{u})=0 \quad \text{(Eq. 2)},$$

where $\varepsilon_w$ is the dielectric constant of the solution, q the elementary charge, $D_\pm$ and $\mu_\pm$ the diffusion coefficients and mobilities of cations and anions, respectively. The fluid transport is modeled by the Stokes-divergence equations $$-\nabla p+\gamma\Delta\vec{u}-q(C_+-C_-)\nabla\psi=0$$

$$\nabla\cdot\vec{u}=0 \quad \text{(Eq. 3)},$$

where p is the solvent pressure and γ is the solvent viscosity. Table 1, presented below, shows values of important simulation parameters.

TABLE 1

Simulation Parameters and Values

| Parameter | Value |
|---|---|
| Solution dielectric constant ($\varepsilon_W$) | 80 $\varepsilon_0$ |
| Insulator dielectric constant ($\varepsilon_i$) | 8 $\varepsilon_0$ |
| Cation/anion mobility ($\mu_\pm$) | $7.62\times10^{-8}$ $m^2/Vs$ |
| Cation/anion diffusivity ($D_\pm$) | $2\times10^{-9}$ $m^2/s$ |
| Bulk ion concentration ($C_0$) | 10 mM |
| Solvent viscosity (γ) | 0.001 $Ns/m^2$ |
| DNA mobility (μ) | $3.5\times10^{-8}$ $m^2/Vs$ |
| DNA diffusivity (D) | $1.8\times10^{-11}$ $m^2/s$ |
| DNA source-end bulk concentration | 2.7 nM |

Figure 14B:
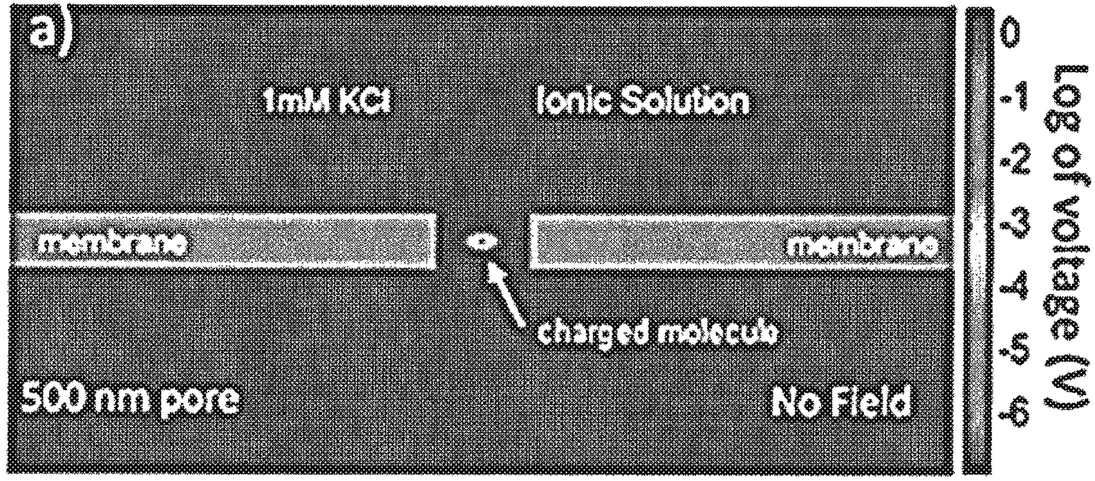
FIGS. 14B-D show simulations of operation of the device of FIG. 14A.
Figure 14B:
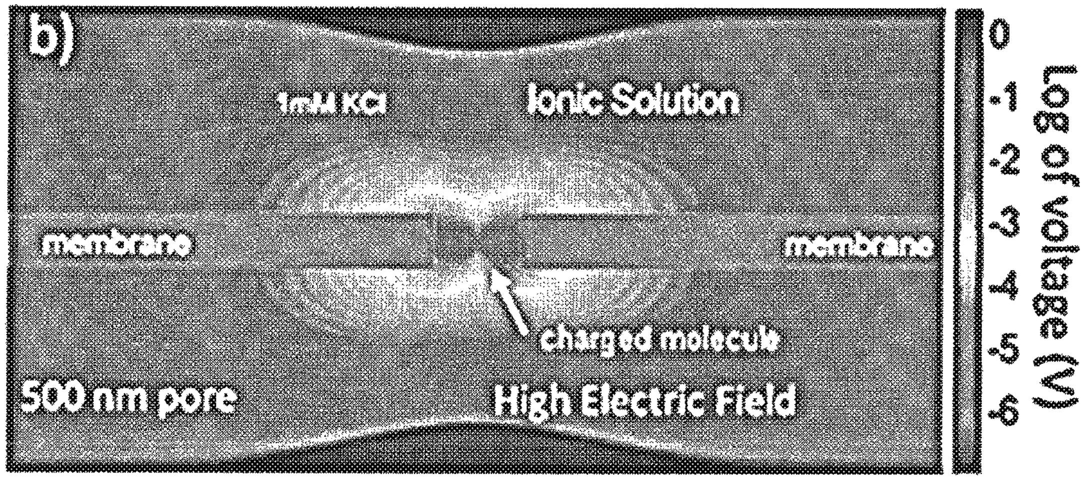
Figure 14C:
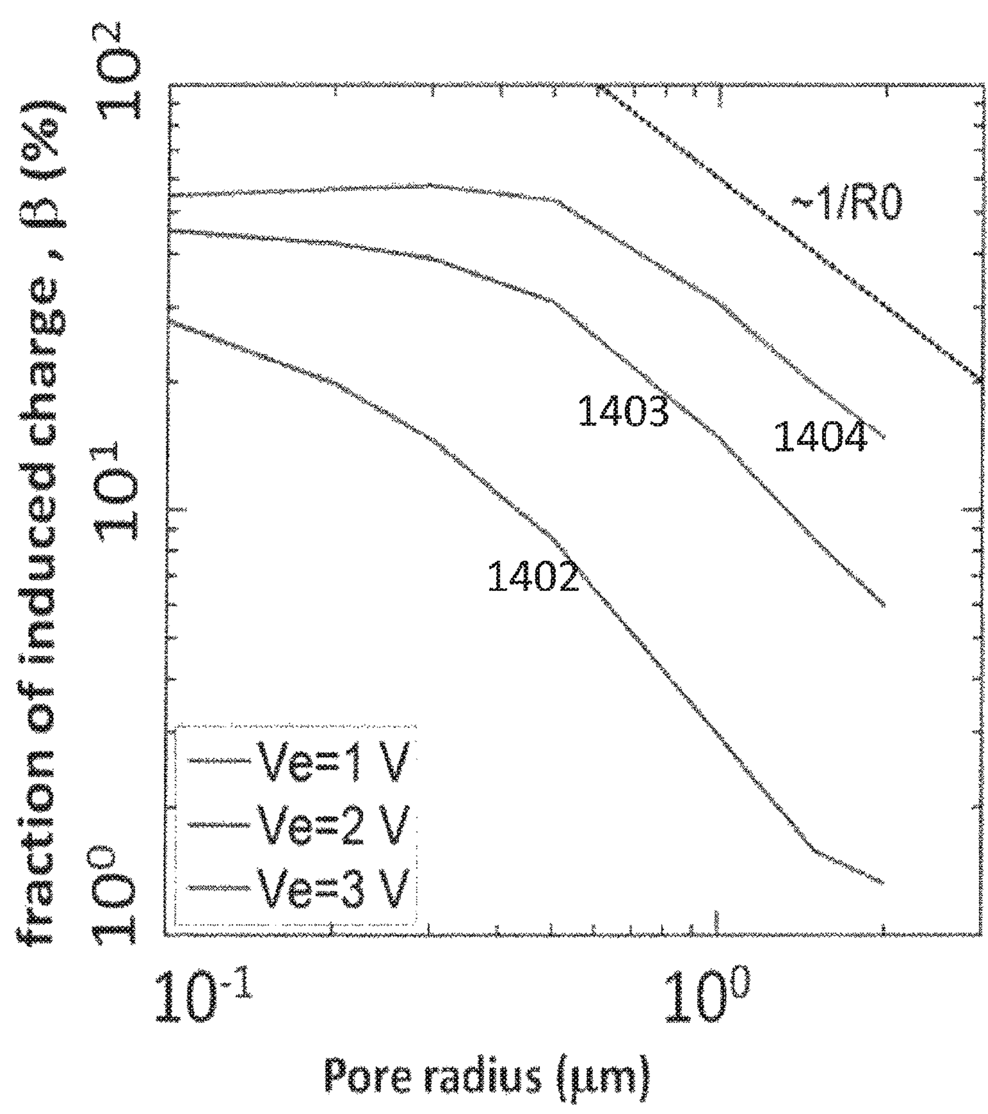
Figure 14D:
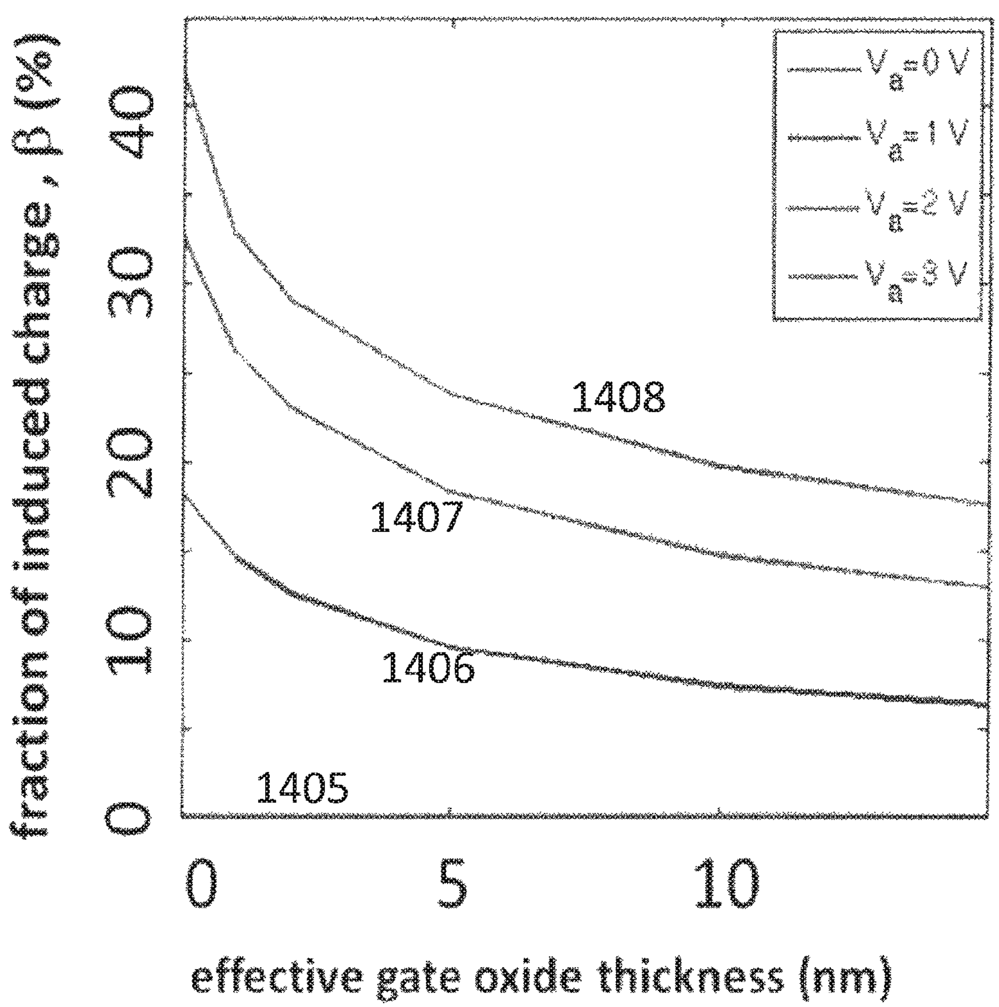

Example simulation results are presented in FIGS. 14B-D. The validity of the simulator has been shown by its ability to accurately simulate DNA translocation behavior through gated pores of similar dimensions for actuation application.

FIG. 14B shows example contour plots of simulated electrostatic potential change due to the presence of the charged molecule with 0 V and 7 V external electrical biases applied, consistent with various aspects of the present disclosure. At zero external electrical bias 1400, the Debye-Hückel screening behavior is observed. In contrast, for an electrical bias of 7 V applied across the pore 1401, significant long-range electrostatic interaction is observed (as indicated by lighter color and field lines). The membrane is modeled as a solid dielectric layer of 500 nm thickness. The ionic solution is 1 mM KCl. The pore radius is set to 300 nm, corresponding to about 30 Debye lengths at this molar concentration.

Further simulations were performed with the device structure of FIG. 14A, which is consistent with various aspects of the present disclosure. The sensing efficiency, or the fraction of induced charge, β, has been calculated for different pore radii (as shown in FIG. 14C) and biasing conditions such as effective gate oxide thickness (a dielectric insulator)(as shown in FIG. 14D).

With reference to FIG. 14C, the fraction of charge in the sensing electrode induced by the biomolecule at 1V 1402, 2V 1403 and 3V 1404 is shown when no oxide is between the electrode and solution. An example plot of the effect of dielectric formation on the sense electrode on sensing efficiency is shown in FIG. 14D at 0V 1405, 1V 1406, 2V 1407 and 3V 1408. The schematic plot shows the effect of dielectric formation on the sense electrode on sensing efficiency. This models the sensing metal electrode sandwiched between two insulating layers. Assuming the biomolecule charge is −Q, the induced charge in the metal electrode is Q'=βQ, which is essentially the amount of charge sensed by the amplifier circuitry. One conclusion of this modeling can be that, with modest DC electrical bias across the pore, the charge that can be sensed is between about 20% and about 40% of the biomolecule charge for a 500 nm pore when the biomolecule is at the center of the pore. In practice, the charge can be delivered much closer to the sense electrode due to the way in which the analyte (e.g., DNA) is immobilized near the periphery of the pore, rather than at the center.

Figure 15:
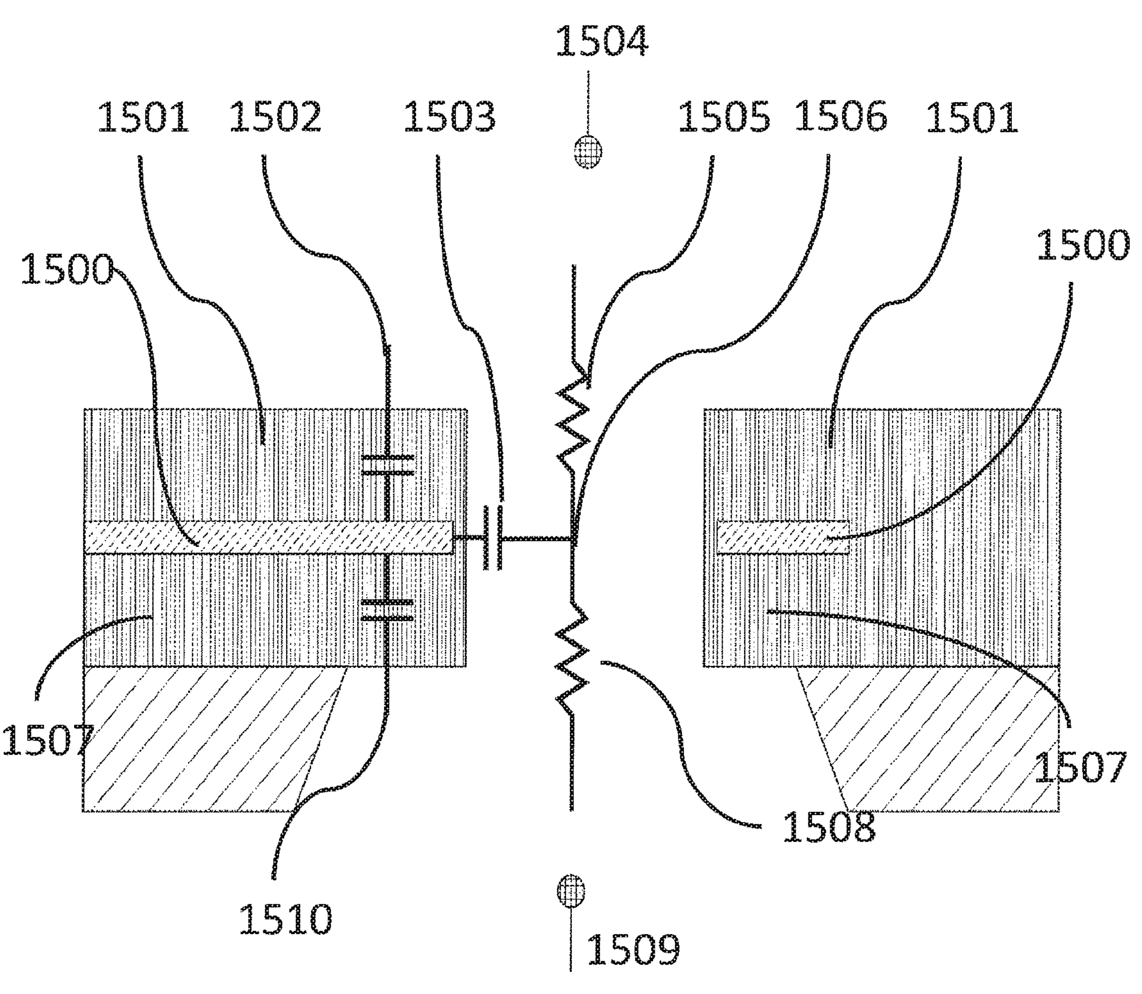
FIG. 15 shows an example of an equivalent circuit model of a sensor of the present disclosure.

FIG. 15 shows a circuit diagram for an individual sensor of the present disclosure. The sensor includes a sensing electrode 1500, which for convenience in making a transistor analogy can be referred to as a “gate”. The sensor also has a top insulator 1501, a top (or source) electrode 1504, a bottom insulator 1507, a bottom (or drain) electrode 1509, and a channel position 1506 at which the sensing is modeled to occur. The top insulator 1501 and bottom insulator 1507 can be the same or optionally can be comprised of different materials. The circuit model includes various components including a capacitance $C_{GS}$ from the gate to the top electrolyte body (or source) 1502, a capacitance $C_C$ from the gate to the channel 1503, a channel to source resistance $R_{GS}$ 1505, a channel to drain resistance $R_{GD}$ 1508, and a gate to drain capacitance $C_{GD}$ 1510. Equations are presented at 1511 and 1512 relating these elements with the voltage at the source ($V_S$), at the drain ($V_D$), in the channel ($V_C$) and at the gate ($V_G$).

Figure 16:
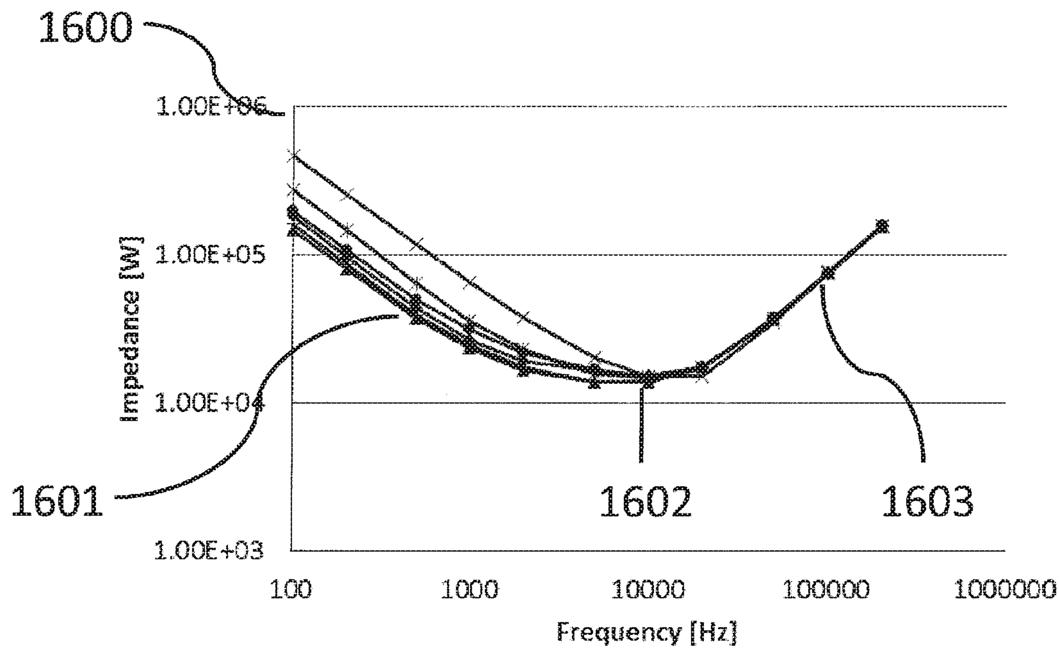
FIG. 16 shows an example of data obtained from operation of a sensor of the present disclosure and used to determine circuit elements of the equivalent circuit model of FIG. 15.
Figure 16:
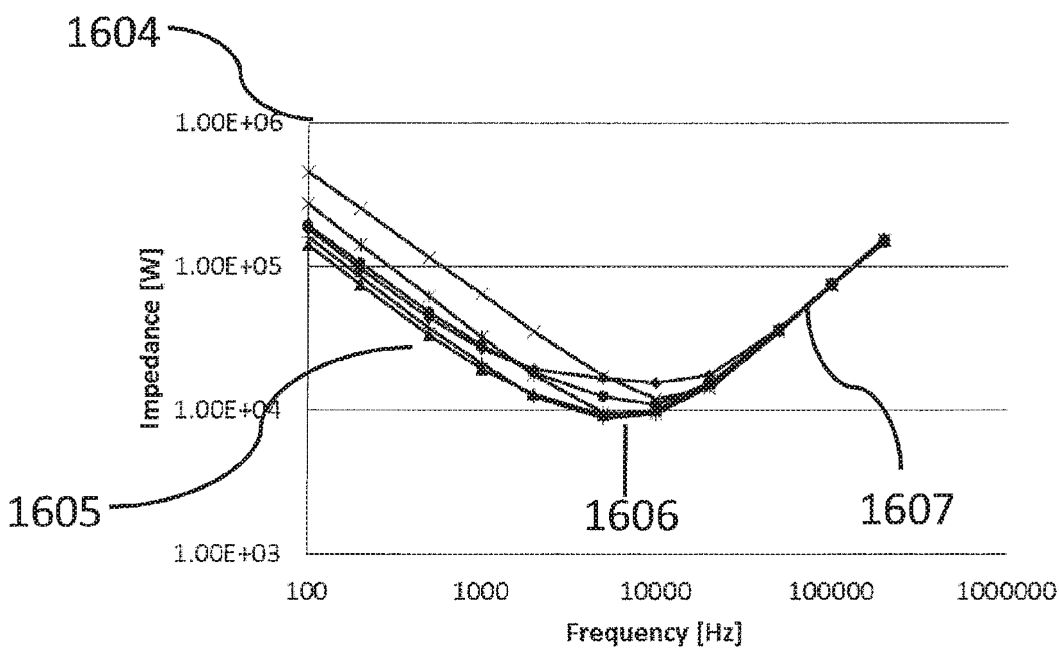

FIG. 16 shows experimentally measured results corresponding to some of the circuit diagram elements described in FIG. 15, with the various graph lines representing measurements of various sensors. The impedance between the gate and drain 1600 is shown as a function of frequency. The declining slope of this plot 1601 represents $C_{GD}$ (at 1510), the minimum of the plot 1602 represents $R_{GD}$ (at 1508), and the increasing slope of this plot 1603 represents the instrument's inductance. The impedance between the gate and source 1604 is also shown as a function of frequency. The declining slope of this plot 1605 represents $C_{GS}$ (at 1502), the minimum of the plot 1606 represents $R_{GS}$ (at 1505), and the increasing slope of this plot 1607 represents the instrument's inductance.

The pore can be any suitable size or shape. The pore can be circular, an oval, square, rectangular, triangular, an elongated slit, or a polygon of 5, 6, 7, 8, 9, 10, or more sides. The sensors and methods of the disclosure can use a "nanopore", but do not require that the pore be a nanopore, which is generally defined to be a pore having a diameter at least about 1 nanometer (nm) and at most about 5 nm or 10 nm. Without being held to any particular theory, this is because the present methods do not rely on blockage of ion flow through the pore by the analyte being sensed, such as described in U.S. Pat. No. 6,428,959, which disclosure is incorporated herein by reference specifically for this related disclosure. Thus, the pore can be larger than a nanopore, which enables a more easily manufacturable and operable device. The pore of the present disclosure can be made from any suitable material (i.e., the pore can be a hole in the material), including $SiO_2$, SiN, aluminum oxide ($Al_2O_3$), gold or mica. In some cases, the pore is a biological pore, such as a protein channel within a lipid membrane.

Figure 17:
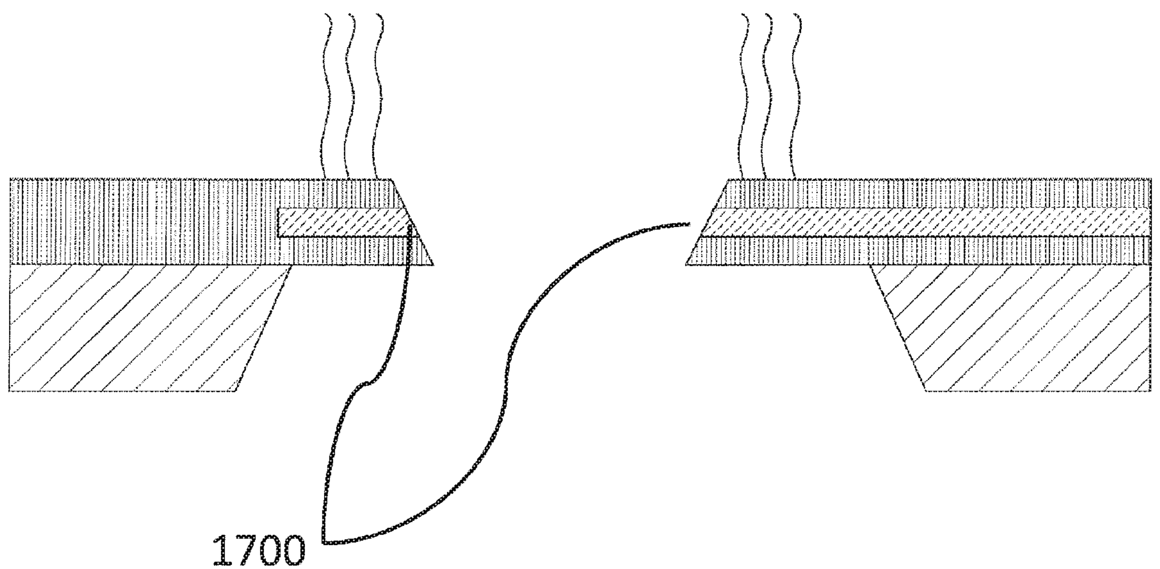
FIG. 17 shows an example of a sensor of the present disclosure having an engineered sensing area.
Figure 17:
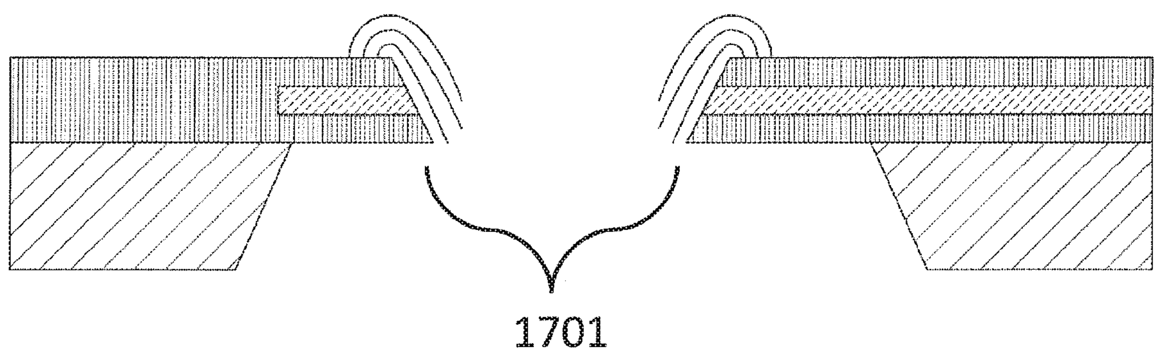

The side wall of the pore can have any suitable shape. In some instances, the side wall is straight and at a right angle to the surface of the membrane (e.g., as shown in FIG. 1). In some cases, the side wall is not at a right angle to the surface of the membrane. The side wall can be slanted. As shown in FIG. 17, the pore can be wider on the cis side (side of the membrane where the analyte is attached) than on the trans side of the membrane. The pore can also be wider on the trans side than on the cis side in some embodiments. In some cases, the pore is hourglass shaped or inverse hourglass shaped. The shape of the pore can be varied to manipulate the properties of the sense area 1700, for example in order to optimize any particular sensing characteristic, such as SNR. In some cases, a tapered pore geometry can result in more secure and/or repeatable placement of the analyte on the sensing electrode surface 1701.

Figure 18:
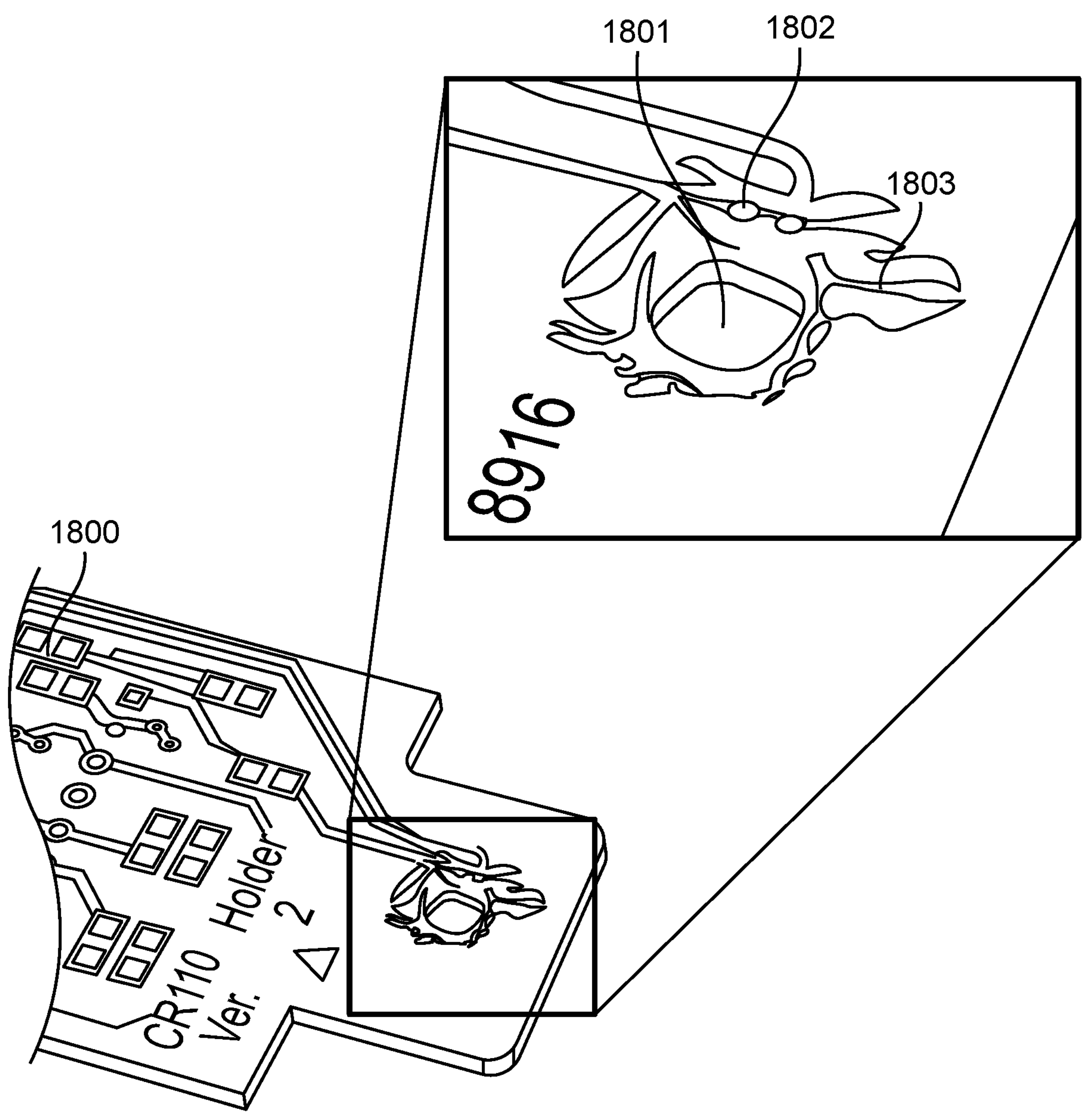
FIG. 18 shows an example of a sensor of the present disclosure interfaced with a printed circuit board.

FIG. 18 shows an example of the sensor chip interfacing with a printed circuit board (PCB). The PCB 1800 holds the sensor chip 1801 in a socket. Electrical connections 1802, in this instance, are made with wire bonding from the PCB to the sensor chip. The chip and the wire bond can be fluidically and electrically insulated with polydimethylsiloxane (PDMS) 1803.

Figure 19:
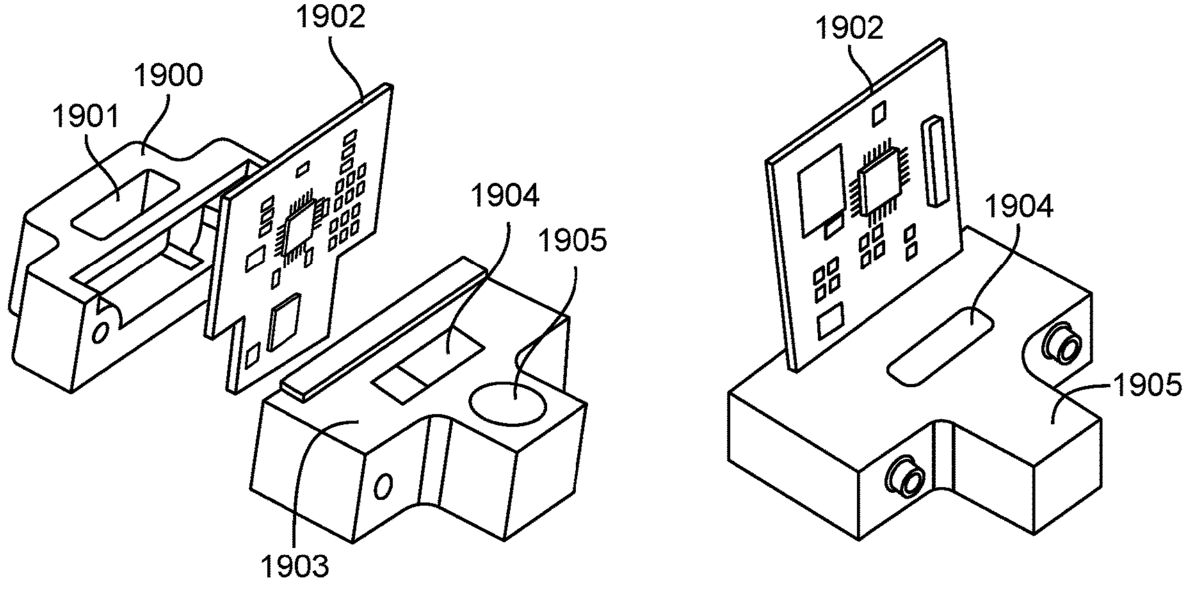
FIG. 19 shows an example of a fluidic cell integrated with the sensor of the present disclosure.

FIG. 19 shows an example of a fluidic cell that can be integrated with the sensor. The left portion of FIG. 19 depicts an exploded view drawing of the fluidic cells to show inner structure, while the right portion of FIG. 19 shows a photograph of the fluidic cell when assembled. The bottom fluidic cell 1900 can be made from polytetrafluoroethylene (PTFE) and can form a fluidic seal for the bottom fluidic reservoir 1901. The reservoir can hold the electrolyte and has an opening for the bottom electrode to make contact with the electrolyte. The fluidic cell can be designed to mount the sensor integrated with the PCB 1902 as described in FIG. 18. The top fluidic cell 1903 can also be made from PTFE and can form a fluidic seal for the top fluidic reservoir 1904. The top fluidic reservoir can hold electrolyte and have an opening for the top electrode to make contact with the electrolyte. The fluidic cell can also have a reservoir for de-ionized water 1905, which can help to humidify the environment in which the device operates.

Figure 20:
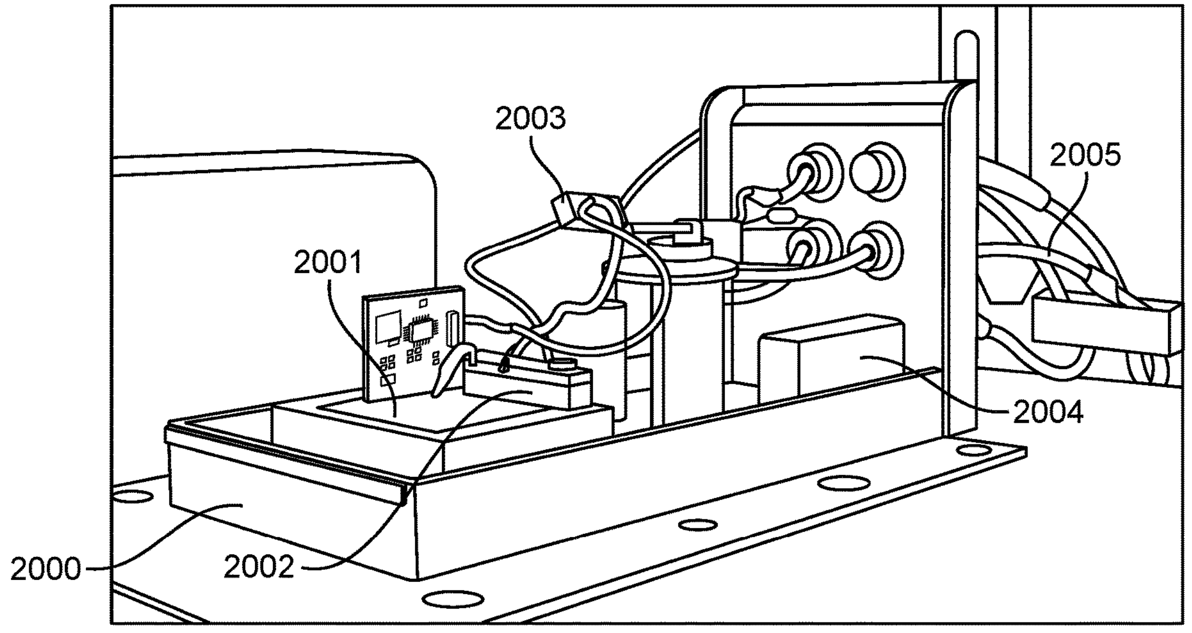
FIG. 20 shows an example of a device for operation of the sensor of the present disclosure.

FIG. 20 shows an instrument capable of operating the sensor of the present disclosure. The instrument can be housed inside a faraday cage (e.g., made of solid copper) 2000. The sensor and fluidic cell described in FIG. 19 is shown 2001. The instrument can have electrodes 2002, an external amplifier circuit 2003, a battery 2004 for the amplifier circuit and application of the electrostatic potential and cables to control the instrument 2005.

Figure 21A:
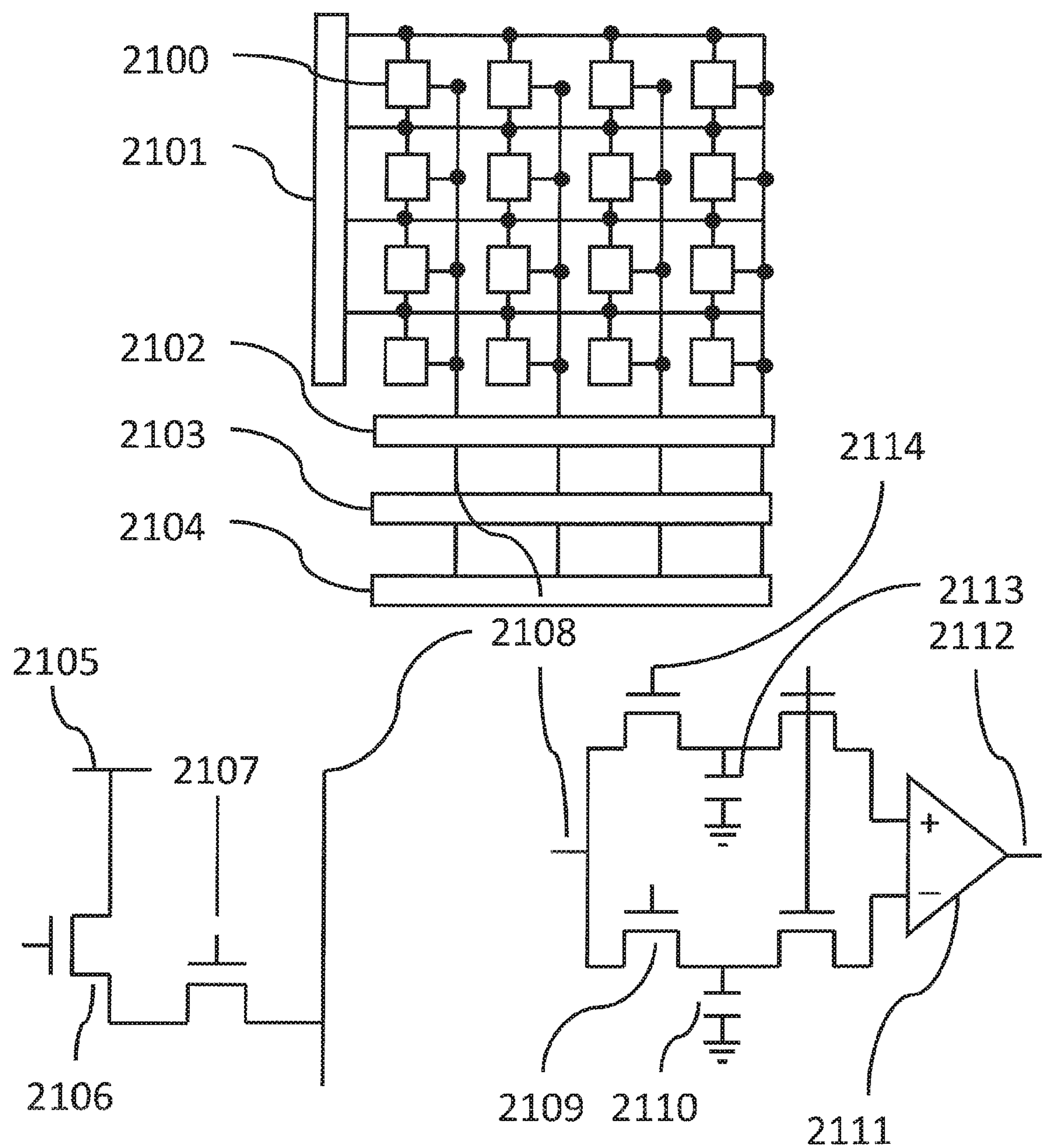
FIG. 21A shows an example of the circuitry of an integrated sensor array of the present disclosure.

FIG. 21A shows an example of an integrated sensor array. The array can have any number of sensors one skilled in the art would recognize, for example, the particular number of sensors is not important, whether the plurality of sensors is minimal or as several/many million. In some cases, each of the individual sensors of the array is individually addressable. An individually addressable sensor can be individually controlled (e.g., have a bias applied to the anode or cathode) and/or individually read (e.g., a signal derived from the sensing electrode). In some cases, a plurality of sensors of the array are addressable as a group. In some instances, a plurality of sensors share a common anode and/or cathode for applying an electrical field across the sensor.

Returning to FIG. 21A, the sensors can be addressed in any suitable way and/or have any suitable integrated circuitry. For example, each single cell of the charge sensor 2100 can be addressed by a vertical access circuit 2101. The array can also have a noise reduction circuit 2102, an analog-to-digital circuit 2103, and a horizontal access circuit 2104. Details within a cell 2100 are shown, including power (e.g., $V_{DD}$ pin) 2105, a source follower amplifier 2106, a select 2107, and data 2108. An example noise reduction circuit 2102 can include a reference select 2109, reference storage 2110, a comparator 2111, analog data out 2112, read storage 2113, and read select 2114.

Figure 21B:
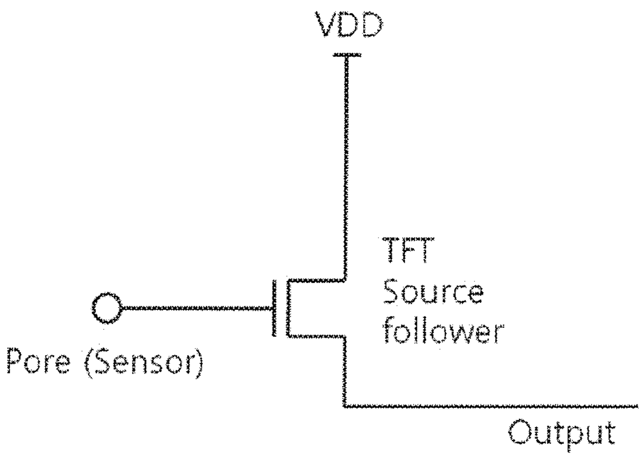
FIGS. 21B-C show examples of additional circuitry useful for an integrated sensor array of the present disclosure.
Figure 21B:
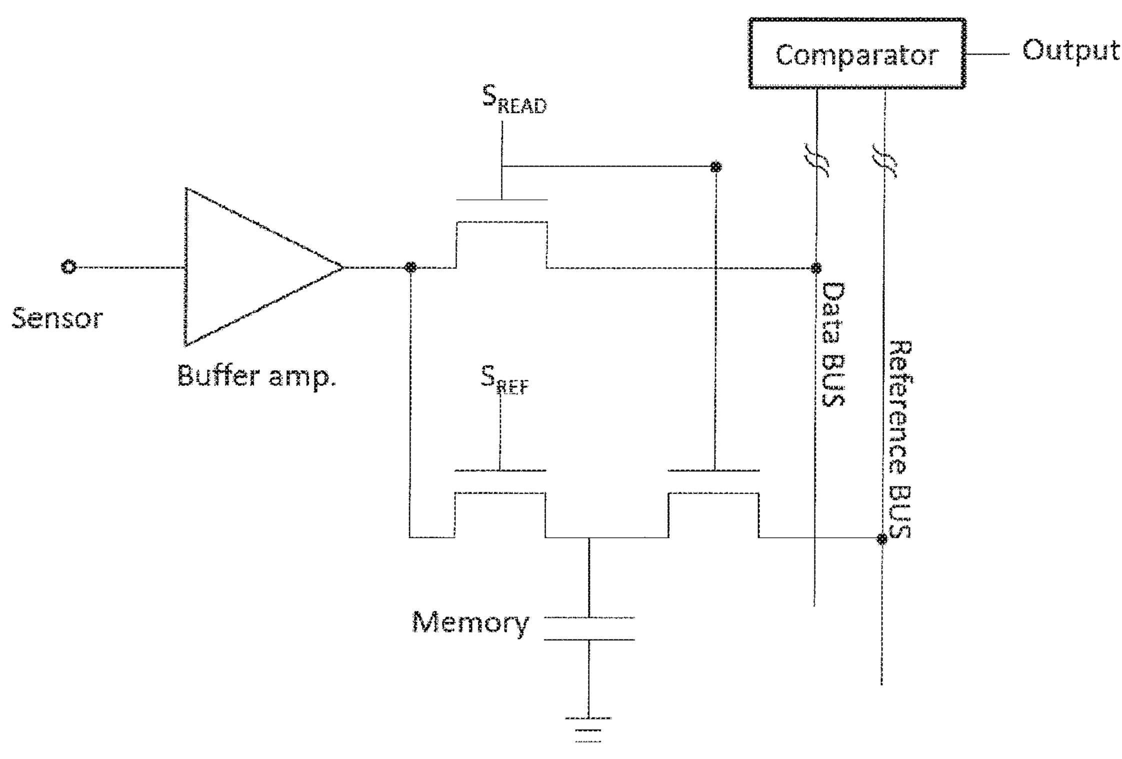
Figure 21C:
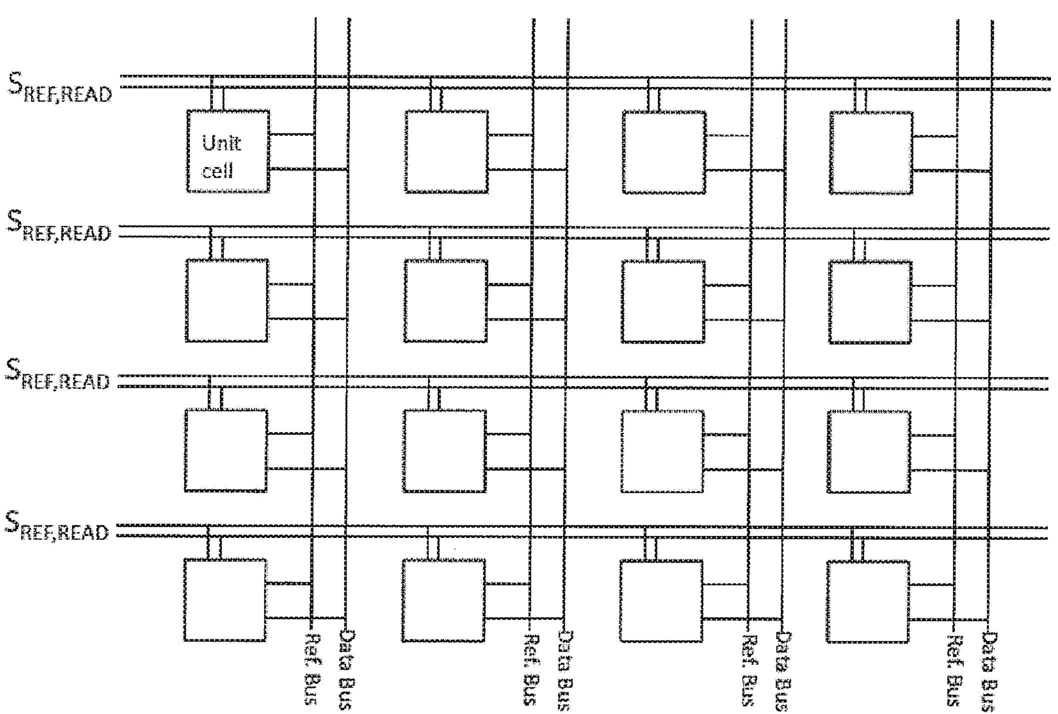

FIG. 21B and FIG. 21C show additional embodiments of sensor circuitry for an integrated sensor array of the present disclosure.

Figure 22:
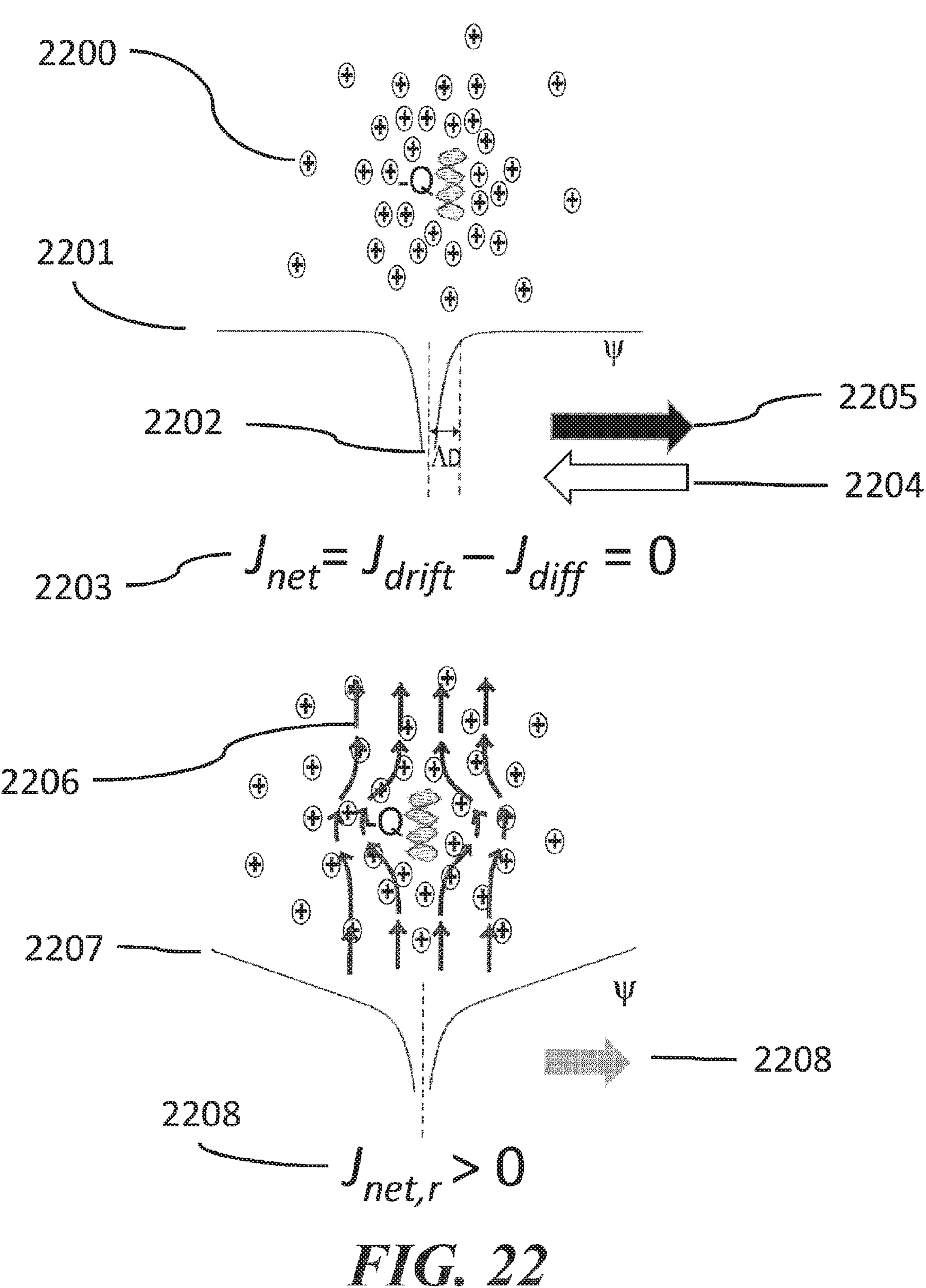
FIG. 22 shows an example of the physics of de-screening in the sensor of the present disclosure.

FIG. 22 illustrates the physics of de-screening. When the system is at equilibrium 2201, the electrostatic potential (Ψ) shows a dramatic change within the Debye length 2202 with counter-ions 2200 effectively shielding the charge (−Q, e.g., DNA). The salt concentration has an effect on the Debye length according to the Debye-Hückel model. For example, the Debye length is about 1 nanometer (nm) for 100 millimolar (mM) potassium chloride (KCl), about 3.4 nm for 10 mM KCl and about 10 nm for 1 mM KC. In contrast, at equilibrium, the net counter-ion current 2203 ($J_{net}$) is approximately zero, where the drift component (Coulombic attraction) of counter-ion current ($J_{drift}$) 2204 effectively balances the diffusion component ($J_{diff}$) 2205. However, in the presence of an external field (non-equilibrium conditions) the counter-ions can flow 2206. The electrostatic potential is in non-equilibrium 2207, where the net counter-ion current is non-zero 2208 (i.e., positive) and the counter-ions flow.

The sensor of the present disclosure can be manufactured using any technique, or combination of techniques, such as photolithography. Table 2, presented below, shows an example of method for making a passive sensor of the present disclosure.

TABLE 2

Example Process for Manufacture of a Passive Sensor

| Step | | Step description | Note |
|---|---|---|---|
| 0 | 0.0 | Photo Alignment Mark | |
| | 0.1 | RCA1 and RCA2 clean | |
| | 0.2 | HMDS Prime | |
| | 0.3 | Resist Coat | 1 μm 3612 resist |
| | 0.4 | Expose Alignment Marks | ASML 80 mJ/$cm^2$ |
| | 0.5 | Develop | |
| 1 | 1.0 | LPCVD Nitride | |
| | 1.1 | Diffusion Clean | |
| | 1.2 | LPCVD Stressed Nitride | 50 nm |
| 2 | 2.0 | Back Window Photo | |
| | 2.1 | RCA1 and RCA2 clean | |
| | 2.2 | HMDS Prime | |
| | 2.3 | Resist Coat | 1 μm 3612 resist |
| | 2.4 | Expose Alignment Marks | ASML 80 mJ/$cm^2$ |
| | 2.5 | Develop | |
| | 2.6 | Nitride RIE to expose bare Si | |
| 3 | 3.0 | Photo Metal LO | |
| | 3.1 | RCA1 | Resist strip |
| | 3.2 | HMDS Prime | |
| | 3.3 | LOL 2000 Deposition | 2k rpm 60 s |
| | 3.4 | Oven bake | 190° C. 10 min |
| | 3.5 | Resist Coat | 1.6 μm 3612 resist |
| | 3.6 | Expose Metal | ASML 120 mJ/$cm^2$ |
| | 3.7 | Develop | |
| 4 | 4.0 | Metal Deposition & LO | |
| | 4.1 | 1 min Ar Sputter clean of surface | |
| | 4.2 | Sputter deposition of 50 nm Pt | |
| | 4.3 | Lift Off in Acetone overnight | |
| 5 | 5.0 | Oxide Deposition | |
| | 5.1 | PECVD Oxide Deposition | 30 nm |
| | 5.2 | ALD Oxide Deposition | 20 nm |
| 6 | 6.0 | Photo Contacts | |
| | 6.1 | PRS1000 Clean | |
| | 6.2 | HMDS Prime | |
| | 6.3 | LOL 2000 Deposition | 2k rpm 60 s |
| | 6.4 | Oven bake | 190° C. 10 min |
| | 6.5 | Resist Coat | 1.6 μm 3612 resist |
| | 6.6 | Expose Pads | ASML 120 mJ/$cm^2$ |
| 7 | 7.0 | Deposit Au and LO | |
| | 7.1 | 1 min Ar Sputter clean of surface | |
| | 7.2 | 10 nm Sputter Dep of Ti | |
| | 7.3 | 200 nm Sputter Dep of Au | |
| | 7.4 | Lift Off in Acetone overnight | |
| 8 | 8.0 | Pore Photo | |
| | 8.1 | PRS1000 Clean | |
| | 8.2 | HMDS Prime | |
| | 8.3 | LOL 2000 Deposition | 2k rpm 60 s |
| | 8.4 | Oven bake | 190° C. 10 min |
| | 8.5 | Resist Coat (Vary thickness for pore size) | 1.6 μm 3612 resist |
| | 8.6 | Expose 1 μm pores | ASML 120 mJ/$cm^2$ |
| | 8.7 | Develop | |
| | 8.8 | Harden Resist | 24 hrs 110° C. |
| y | 9.0 | Pore etch | |
| | 9.1 | Oxide RIE | |
| | 9.2 | Ar Sputter etch of Pt | |
| | 9.3 | Nitride RIE | |
| 10 | 10.0 | Front surface protection | |
| | 10.1 | PRS1000 Clean | |
| | 10.2 | Protek3 Primer Deposition | 1500 rpm 60 s |
| | 10.3 | Oven bake | 120° C. 120 s |
| | 10.4 | Protek3 Deposition | 1000 rpm 60 s |
| | 10.5 | Oven bake | 200° C. 30 min |
| 11 | 11.0 | Through wafer etch | |
| | 11.1 | TMAH etch | 8% TMAH |
| 12 | 12.0 | Dice chips and clean | |
| | 12.1 | Wafer Saw dice chips | |
| | 12.2 | Remove Protek Step1 | ACT-XT1100 27° C. 30 min |
| | 12.3 | Remove Protek Step2 | ACT412 80° C. 30 min |
| | 12.4 | PRS1000 Clean | |

TABLE 2-continued

| Example Process for Manufacture of a Passive Sensor | | | |
|---|---|---|---|
| Step | | Step description | Note |
| 13 | 13.0 | Passivation | |
| | 13.1 | ALD Oxide Deposition | 2.5 nm |

As illustrated, various modules and/or other circuit-based building blocks may be implemented to carry out one or more of the operations and activities described herein and/or shown in the Figures. In such contexts, these modules and/or building blocks represent circuits that carry out one or more of these or related operations/activities. For example, in some embodiments, one or more modules and/blocks are discrete logic circuits or programmable logic circuits configured and arranged for implementing these operations/activities, as in the circuit modules/blocks shown herein. In some cases, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules/blocks include a combination of a CPU hardware-based circuit and a set of instructions in the form of firmware, where the first module/block includes a first CPU hardware circuit with one set of instructions, and the second module/block includes a second CPU hardware circuit with another set of instructions.

The present disclosure provides computer control systems that can be employed to regulate or otherwise control the sensors and methods provided herein. A control system of the present disclosure can be programmed to control process parameters to, for example, sense an analyte.

Figure 23:
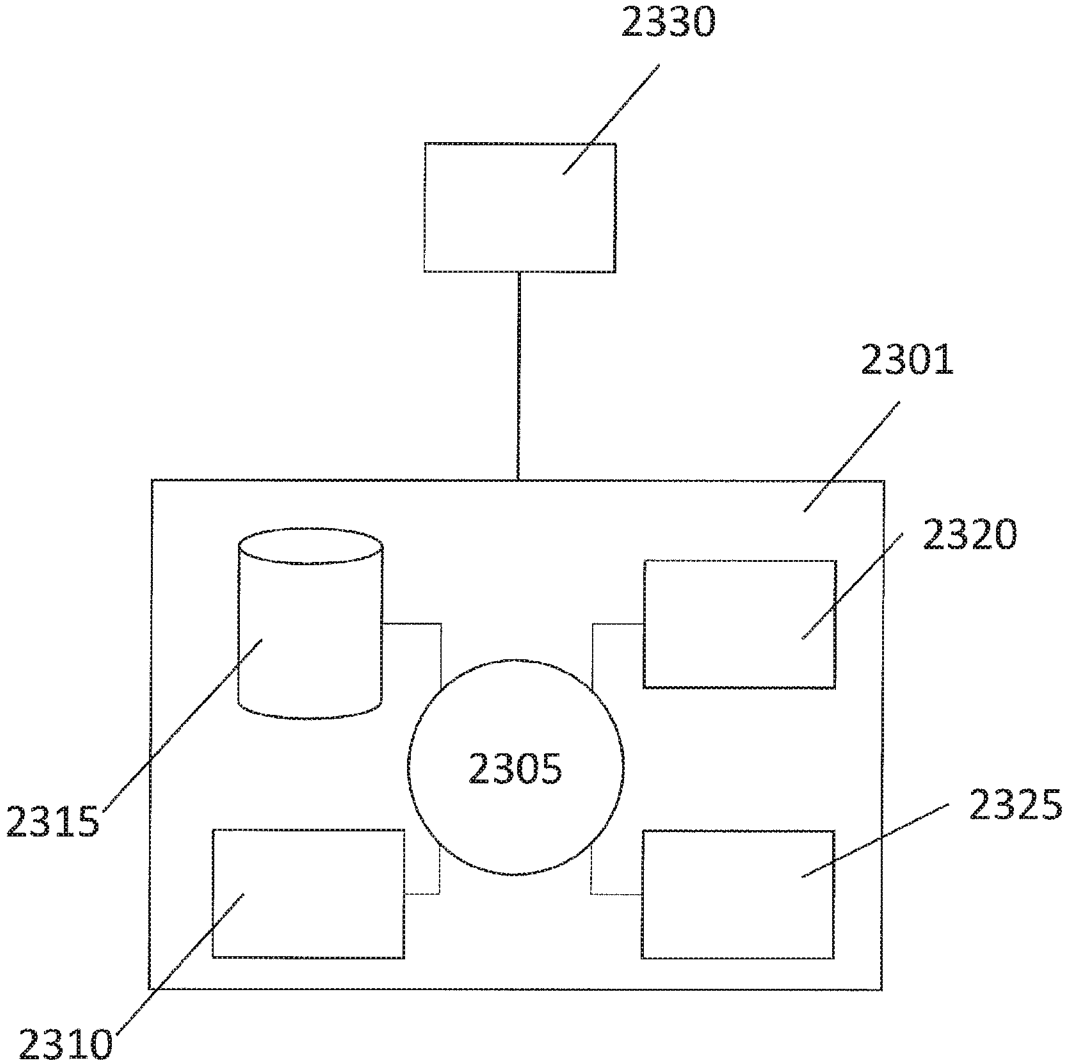
FIG. 23 shows an example of a computer system for operation of the sensor of the present disclosure.

FIG. 23 shows a computer system 2301 that is programmed or otherwise configured to regulate the operation of the sensor. The computer system 2301 can regulate, for example, flow rates, temperatures, pressures, mechanical manipulations, applied voltages or other electrical inputs and/or outputs, and the like.

The computer system 2301 includes a central processing unit (CPU, also "processor" and "computer processor" herein) 2305, which can be a single core or multi core processor, or a plurality of processors for parallel processing. The computer system 2301 also includes memory or memory location 2310 (e.g., random-access memory, read-only memory, flash memory), electronic storage unit 2315 (e.g., hard disk), communication interface 2320 (e.g., network adapter) for communicating with one or more other systems, and peripheral devices 2325, such as cache, other memory, data storage and/or electronic display adapters. The memory 2310, storage unit 2315, interface 2320 and peripheral devices 2325 are in communication with the CPU 2305 through a communication bus, such as a motherboard. The storage unit 2315 can be a data storage unit (or data repository) for storing data.

The CPU 2305 can execute a sequence of machine-readable instructions, which can be embodied in a program or software. The instructions may be stored in a memory location, such as the memory 2310. Examples of operations performed by the CPU 2305 can include fetch, decode, execute, and writeback.

The storage unit 2315 can store files, such as drivers, libraries and saved programs. The storage unit 2315 can store programs generated by users and recorded sessions, as well as output(s) associated with the programs. The storage unit 2315 can store user data, e.g., user preferences and user programs. The computer system 2301 in some cases can include one or more additional data storage units that are external to the computer system 2301, such as located on a remote server that is in communication with the computer system 2301 through an intranet or the Internet.

The computer system 2301 can be in communication with a system 2330, including a device with integrated fluidics and/or process elements. Such process elements can include sensors, flow regulators (e.g., valves), and pumping systems that are configured to direct a fluid.

Methods as described herein can be implemented by way of machine (e.g., computer processor) executable code stored on an electronic storage location of the computer system 2301, such as, on the memory 2310 or electronic storage unit 2315. The machine executable or machine readable code can be provided in the form of software. During use, the code can be executed by the processor 2305. In some cases, the code can be retrieved from the storage unit 2315 and stored on the memory 2310 for ready access by the processor 2305. In some situations, the electronic storage unit 2315 can be precluded, and machine-executable instructions are stored on memory 2310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor (circuit) memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

It should be understood from the foregoing that, while particular implementations have been illustrated and described, various modifications can be made thereto and are contemplated herein. For example, the embodiments described herein can be combined with or modified to yield yet more embodiments of the present invention. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method for detecting a charged analyte, comprising:

(a) providing a fluidic chamber comprising first and second portions and a membrane separate from and between the first and second portions, wherein one of the first and second portions includes an electrolyte, wherein the membrane comprises a pore suitable for (i) flow of the electrolyte between the first and second portions of the fluidic chamber, and (ii) flow of at least one charged analyte tethered in proximity to the pore into the pore;

(b) providing first and second bias electrodes in the first and second portions of the fluidic chamber, respectively;

(c) applying an electric field to the first and second bias electrodes so as to cause the electrolyte to pass through the pore and to pull the at least one charged analyte that is tethered in proximity to the pore into the pore, wherein the electric field has a strength of at least $10^5$ Volts per meter; and (d) measuring a signal indicative of change in charge of the at least one charged analyte upon the at least one charged analyte being pulled into the pore while remaining tethered in proximity to the pore, wherein measuring the signal indicative of the change in charge includes: (i) measurement of a reference charge while the at least one charged analyte is pulled into the pore while remaining tethered in proximity to the pore, (ii) incorporation of a nucleotide that is complimentary to a nucleic acid molecule to be sequenced, (iii) sensing a changed charge after incorporation of the complimentary nucleotide while the at least one charged analyte is pulled into the pore while remaining tethered in proximity to the pore, and (iv) comparing the changed charge to the reference charge, wherein the at least one charged analyte is tethered in proximity to the pore via a covalent bond, wherein the membrane is a solid state membrane, and the at least one charged analyte is tethered via the covalent bond to an exterior surface of the solid state membrane, wherein the membrane and a wall of the pore are surrounded by an electrical double layer (EDL), and wherein the electric field having the strength of at least $10^5$ Volts per meter de-screens the EDL.

2. The method of claim 1, wherein in response to the electric field applied in (c), the at least one charged analyte is directed to a position in proximity to a periphery of the pore.

3. The method of claim 1, wherein the pore is formed in the solid state membrane.

4. The method of claim 1, wherein the at least one charged analyte is tethered concurrently with directing the at least one charged analyte into the pore.

5. The method of claim 1, wherein the electric field applied to the first and second bias electrodes in the first and second portions of the fluidic chamber interacts with the at least one charged analyte to tether the at least one charged analyte in proximity to the pore.

6. The method of claim 1, wherein the signal is measured using a sensing electrode that is located at a distance of at least 2-times a Debye length associated with the at least one charged analyte.

7. The method of claim 1, wherein the signal is measured using a sensing electrode embedded in the membrane.

8. The method of claim 1, wherein a diameter of the pore and a diameter of the charged analyte are each at most 10 nanometers.

9. The method of claim 1, wherein the electric field has the strength sufficient to suppress electrical-charge shielding within the pore.

10. The method of claim 1, wherein the at least one charged analyte is a nucleic acid molecule.

11. The method of claim 1, wherein the electric field generates a non-equilibrium transport condition with respect to the electrolyte.

12. A system for detecting a charged analyte, comprising:

a fluidic chamber comprising first and second portions and a membrane separate from and between the first and second portions, wherein the membrane comprises a pore suitable for (i) flow of an electrolyte between the first and second portions of the fluidic chamber and (ii)

flow of at least one charged analyte tethered in proximity to the pore into the pore;

first and second bias electrodes disposed in the first and second portions of the fluidic chamber, respectively;

a first circuit connected to the first and second bias electrodes and configured to apply an electric field capable of causing the electrolyte to pass through the pore and further causing the at least one charged analyte that is tethered in proximity to the pore to be pulled into the pore, wherein the electric field has a strength of at least $10^5$ Volts per meter; and a second circuit configured to measure a signal indicative of a charge or change in charge of the at least one charged analyte upon the at least one charged analyte being pulled into the pore while remaining tethered in proximity to the pore;

wherein measuring the signal indicative of the change in charge includes: (i) measurement of a reference charge while the at least one charged analyte is pulled into the pore while remaining tethered in proximity to the pore, (ii) incorporation of a nucleotide that is complimentary to a nucleic acid molecule to be sequenced, (iii) sensing a changed charge after incorporation of the complimentary nucleotide while the at least one charged analyte is pulled into the pore while remaining tethered in proximity to the pore, and (iv) comparing the changed charge to the reference charge, wherein the at least one charged analyte is tethered in proximity to the pore via a covalent bond, wherein the membrane is a solid state membrane, and the at least one charged analyte is tethered via the covalent bond to an exterior surface of the solid state membrane, and wherein the membrane and a wall of the pore are surrounded by an electrical double layer (EDL), and wherein the electric field having the strength of at least $10^5$ Volts per meter de-screens the EDL.

13. The system of claim 12, wherein the electric field applied to the first and second bias electrodes disposed in the first and second portions of the fluidic chamber, respectively, is configured to interact with the at least one charged analyte to tether the at least one charged analyte in proximity to the pore.

14. The system of claim 12, wherein the second circuit comprises a sensing electrode for measuring the signal, wherein the sensing electrode is located at a distance of at least 2-times a Debye length associated with the at least one charged analyte.

15. The system of claim 12, wherein a diameter of the pore is at most 10 nanometers.

16. The system of claim 12, wherein the electric field has the strength sufficient to suppress electrical-charge shielding within the pore.

17. The system of claim 12, wherein the second circuit comprises an electrode embedded in the membrane in proximity to the pore.

18. The system of claim 12, further comprising an amplifier capable of amplifying the signal, wherein the amplifier is within 5000 μm from the pore.

19. The system of claim 12, wherein the pore is formed in the solid state membrane.

20. The system of claim 12, wherein a diameter of the pore is 100 to 300 nanometers.

* * * * *